United States Patent
Casillas et al.

(10) Patent No.: US 10,435,391 B2
(45) Date of Patent: Oct. 8, 2019

(54) COMPOUNDS

(71) Applicant: GlaxoSmithKline Intellectual Property Development Limited, Brentford, Middlesex (GB)

(72) Inventors: Linda N. Casillas, Collegeville, PA (US); John David Harling, Stevenage (GB); Afjal Hussain Miah, Stevenage (GB); Mark David Rackham, Stevenage (GB); Ian Edward David Smith, Stevenage (GB)

(73) Assignee: GLAXOSMITHKLINE INTELLECTUAL PROPERTY DEVELOPMENT LIMITED, Brentford, Middlesex (GB)

( * ) Notice: Subject to any disclaimer, the term of this patent is extended or adjusted under 35 U.S.C. 154(b) by 0 days.

(21) Appl. No.: 15/568,025

(22) PCT Filed: Apr. 20, 2016

(86) PCT No.: PCT/US2016/028332
§ 371 (c)(1),
(2) Date: Oct. 20, 2017

(87) PCT Pub. No.: WO2016/172134
PCT Pub. Date: Oct. 27, 2016

(65) Prior Publication Data
US 2018/0134688 A1  May 17, 2018

(30) Foreign Application Priority Data
Apr. 22, 2015 (GB) .................................. 1506872.9

(51) Int. Cl.
| *C07D 403/14* | (2006.01) |
| *A61P 35/00* | (2006.01) |
| *C07D 401/14* | (2006.01) |
| *C07D 417/14* | (2006.01) |
| *C07D 487/04* | (2006.01) |
| *A61P 29/00* | (2006.01) |

(52) U.S. Cl.
CPC ............ *C07D 403/14* (2013.01); *A61P 29/00* (2018.01); *C07D 401/14* (2013.01); *C07D 417/14* (2013.01); *C07D 487/04* (2013.01)

(58) Field of Classification Search
CPC .. C07D 403/14; C07D 401/14; C07D 417/14; C07D 487/04
See application file for complete search history.

(56) References Cited

U.S. PATENT DOCUMENTS

| 9,346,815 | B2 | 5/2016 | Zak et al. |
| 9,771,370 | B2 | 9/2017 | Sherer |
| 9,982,000 | B2 | 5/2018 | Kelley et al. |
| 2006/0128632 | A1 | 6/2006 | Sharma et al. |
| 2010/0273812 | A1 | 10/2010 | Wang et al. |
| 2014/0206688 | A1* | 7/2014 | Bury ..................... C07D 403/12 514/234.5 |
| 2014/0356322 | A1 | 12/2014 | Crews et al. |
| 2016/0310423 | A1 | 10/2016 | Betancort et al. |
| 2018/0118733 | A1* | 5/2018 | Harling .............. A61K 31/4725 |

FOREIGN PATENT DOCUMENTS

| WO | WO 2011/140442 A1 | 11/2011 |
| WO | WO2014/043437 | 3/2014 |
| WO | WO2014128622 | 8/2014 |
| WO | WO2015/160845 | 10/2015 |
| WO | WO2016/172134 | 10/2016 |
| WO | WO2016/172618 | 10/2016 |
| WO | WO 2017/046036 A1 | 3/2017 |

OTHER PUBLICATIONS

Buckley et al. Angew. Chem. Int. Ed. 2014, 53, 2312-2330.*
Toure et al. Angew. Chem. Int. Ed. 2016, 55, 1966-1973.*
Oost et al. J. Med. Chem. 2004, 47, 4417-4426.*
Bondeson, Daniel P. et al, "Catalytic in vivo protein knockdown by small-molecule PROTACs", Nat Chem Biol. Aug. 2015; 11 (8): 611-617.
Peng et al., "Bivalent Smac Mimetics with a Diazabicyclic Core as Highly Potent Antagon ists of XIAP and c1AP 1/2 and Novel Anticancer Agents", Journal of Medicinal Chemistry. vol. 55, (2012), pp. 106-114, XP055233063.
N Ohoka et al: "Cancer cell death induced by novel small molecules degrading the TACC3 protein via the ubiquitin-proteasome pathway", Cell Death and Disease, vol. 5, No. 11, Nov. 6, 2014 (Nov. 6, 2014), p. e1513, XP055281118.
Buckley, et al., Small Molecule Control of Intracellular Protein Levels Through Modulation of the Ubiquitin Proteasome System, Angew Chem Int Ed Engl. 2014, vol. 53(9), pp. 2312-2330.

* cited by examiner

*Primary Examiner* — Irina Neagu
(74) *Attorney, Agent, or Firm* — Nora L. Stein; Fang Qian; Edward R. Gimmi

(57) ABSTRACT

The present invention relates to compounds, compositions, combinations and medicaments containing said compounds and processes for their preparation. The invention also relates to the use of said compounds, combinations, compositions and medicaments, for example as inhibitors of the activity of RIP2 kinase, including degrading RIP2 kinase, the treatment of diseases and conditions mediated by the RIP2 kinase, in particular for the treatment of inflammatory diseases or conditions.

6 Claims, No Drawings

COMPOUNDS

This application is a 371 of International Application No. PCT/US2016/028332, filed 20 Apr. 2016, which claims benefit to Application No. GB 1506872.9 filed 22 Apr. 2015. The entire teachings of the above identified applications are incorporated herein by reference.

FIELD OF THE INVENTION

The present invention relates to compounds, compositions, combinations and medicaments containing said compounds and processes for their preparation. The invention also relates to the use of said compounds, combinations, compositions and medicaments, for example as inhibitors of the activity of RIP2 kinase, including degrading RIP2 kinase, the treatment of diseases and conditions mediated by RIP2 kinase, in particular for the treatment of inflammatory diseases or conditions

BACKGROUND OF THE INVENTION

Receptor interacting protein-2 (RIP2) kinase, which is also referred to as CARD3, RICK, CARDIAK, or RIPK2, is a TKL family serine/threonine protein kinase involved in innate immune signaling. RIP2 kinase is composed of an N-terminal kinase domain and a C-terminal caspase-recruitment domain (CARD) linked via an intermediate (IM) region ((1998) *J Biol. Chem.* 273, 12296-12300; (1998) *Current Biology* 8, 885-889; and (1998) *J Biol Chem.* 273, 16968-16975). The CARD domain of RIP2 kinase mediates interaction with other CARD-containing proteins, such as NODI and NOD2 ((2000) *J Biol Chem.* 275, 27823-27831 and (2001) *EMBO reports* 2, 736-742). NODI and NOD2 are cytoplasmic receptors which play a key role in innate immune surveillance. They recognize both gram positive and gram negative bacterial pathogens and are activated by specific peptidoglycan motifs, diaminopimelic acid (i.e., DAP) and muramyl dipeptide (MDP), respectively ((2007) *J Immunol* 178, 2380-2386).

Following activation, RIP2 kinase associates with NODI or NOD2 and appears to function principally as a molecular scaffold to bring together other kinases (TAKI, IKKα/β/γ) involved in NF-κB and mitogen-activated protein kinase activation ((2006) *Nature Reviews Immunology* 6, 9-20). RIP2 kinase undergoes a K63-linked polyubiquitination on lysine-209 which facilitates TAKI recruitment ((2008) *EMBO Journal* 27, 373-383). This post-translational modification is required for signaling as mutation of this residue prevents NOD 1/2 mediated NF-kB activation. RIP2 kinase also undergoes autophosphorylation on serine-176, and possibly other residues ((2006) *Cellular Signalling* 18, 2223-2229). Studies using kinase dead mutants (K47A) and non-selective small molecule inhibitors have demonstrated that RIP2 kinase activity is important for regulating the stability of RIP2 kinase expression and signaling ((2007) *Biochem J* 404, 179-190 and (2009) *J Bioi. Chem.* 284, 19183-19188).

Dysregulation of RIP2-dependent signaling has been linked to auto inflammatory diseases. Gain-of-function mutations in the NACHT-domain of NOD2 cause Blau Syndrome, early-onset sarcoidosis, a pediatric granulomateous disease characterized by uveitis, dermatitis, and arthritis ((2001) *Nature Genetics* 29, 19-20; (2005) *Journal of Rheumatology* 32, 373-375; (2005) *Current Rheumatology Reports* 7, 427-433; (2005) *Blood* 105, 1195-1197; (2005) *European Journal of Human Genetics* 13, 742-747; (2006) *American Journal of Ophthalmology* 142, 1089-1092; (2006) *Arthritis & Rheumatism* 54, 3337-3344; (2009) *Arthritis & Rheumatism* 60, 1797-1803; and (2010) *Rheumatology* 49, 194-196). Mutations in the LRR-domain of NOD2 have been strongly linked to susceptibility to Crohn's Disease ((2002) *Am. J Hum. Genet.* 70, 845-857; (2004) *European Journal of Human Genetics* 12, 206-212; (2008) *Mucosal Immunology* (2008) 1 (Suppll), 55-59. 1, S5-S9; (2008) *Inflammatory Bowel Diseases* 14, 295-302; (2008) *Experimental Dermatology* 17, 1057-1058; (2008) *British Medical Bulletin* 87, 17-30; (2009) *Inflammatory Bowel Diseases* 15, 1145-1154 and (2009) *Microbes and Infection* 11, 912-918). Mutations in NODI have been associated with asthma ((2005) *Hum. Mol. Genet.* 14, 935-941) and early-onset and extra-intestinal inflammatory bowel disease ((2005) *Hum. Mol. Genet.* 14, 1245-1250). Genetic and functional studies have also suggested a role for RIP2-dependent signaling in a variety of other granulomateous disorders, such as sarcoidosis ((2009) *Journal of Clinical Immunology* 29, 78-89 and (2006) *Sarcoidosis Vasculitis and Diffuse Lung Diseases* 23, 23-29) and Wegner's Granulomatosis ((2009) *Diagnostic Pathology* 4, 23).

A potent, selective, small molecule inhibitor of RIP2 kinase activity would block RIP2-dependent pro-inflammatory signaling and thereby provide a therapeutic benefit in auto inflammatory diseases characterized by increased and/or dysregulated RIP2 kinase activity.

It would be desirable to investigate other approaches to antagonise the RIP2 kinase.

One approach would be to develop selective RIP2 kinases down regulators or degraders that reduce RIP2 expression at either the transcript or protein level.

Several methods are available for the manipulation of protein levels, including proteolysis targeting chimeric molecules (Protacs) which contain a ligand that recognizes the target protein linked to a ligand that binds to a specific E3 ubiquitin ligase. It would be desirable to have a small molecule which can simultaneously bind RIP2 kinase and an E3 ubiquitin ligase and which promotes ubiquitination of RIP2 Kinase and leads to its degradation by the Proteosome. One suitable E3 ubiquitin ligase is the von Hippel-Lindau tumour suppressor (VHL), see for example WO2013/106643.

It would be desirable to identify further ubiquitin ligase binding molecules to incorporate into PROTAC molecules.

Inhibitors of Apoptosis (IAP) have been proposed with limited success, see for example Okuhira et al, Cell Death and Disease, 2014, 5, e1513. IAP inhibitors now known which can be of use in their own right as antitumour agents, see for example L. Bai et al./Pharmacology & Therapeutics 144 (2014) 82-95 Apoptosis is one form of programmed cell-death and is a normal cellular process used by multicellular organisms to eliminate damaged or unwanted cells. Apoptosis is a tightly regulated process and faulty regulation of apoptosis is implicated in many human diseases, including cancer, autoimmune diseases, inflammation, and neurogenesis (Lowe S. W and Lin 2000 Carcinogenesis 21(3), 485-495, Nicholson D. W. 2000, Nature 407 (6805) 810-816, Reed J. C. 2002 Nat Rev Drug Discovery 1(2) 111-121).

IAP inhibitors are disclosed in WO 2014031487 WO 2014047024 which describe linked dimeric compounds. WO 2014055461 describes bivalent compounds and WO 2008128171 describes IAP inhibitors all with a view to treating disorders associated with apoptosis, particularly cancer.

The present inventors have identified IAP compounds which when incorporated into PROTACs targeting RIP2 kinase are capable of promoting target degradation.

SUMMARY OF THE INVENTION

The present invention provides Protac compounds which modulate RIP2 kinase activity including degradation thereof which comprise RIP2 kinase inhibitors having the following substructure:

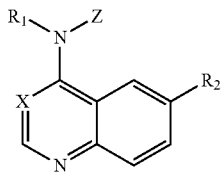

wherein X represents N or —CH.

RIP 2 inhibitors with this substructure are disclosed in WO2014/128622, WO20140/43437, WO 2013/025958, WO 2012/122011, WO 2012/021580 and WO 2011140442. These applications describe suitable substitutions on equivalent positions to Z, $R^1$ and $R^2$ in the RIP2 binding portion depicted.

In a first aspect the present invention provides a compound of formula (I):

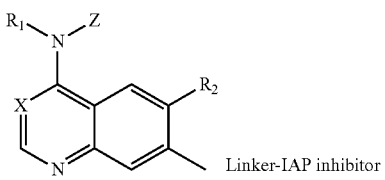

(I)

wherein

X represents N or CH;

L is a linking group comprising a length of 4-20 atoms in shortest length, $R^1$ is H, —SO$_2$(C$_1$-C$_4$)alkyl, —CO(C$_1$-C$_4$)alkyl, or (C$_1$-C$_4$)alkyl;

$R^2$ is —SR$^a$, —SOR$^a$, —SO$_2$R$^a$, —SO$_2$NH$_2$, or —SO$_2$NR$^b$R$^c$, wherein R$^a$ is (C$_1$-C$_6$)alkyl, halo(C$_1$-C$_6$)alkyl, (C$_3$-C$_7$)cycloalkyl, 4-7 membered heterocycloalkyl, aryl, or heteroaryl, wherein:

said (C$_1$-C$_6$)alkyl is optionally substituted by one or two groups each independently selected from the group consisting of cyano, hydroxyl, (C$_1$-C$_6$)alkoxy, (C$_1$-C$_6$)alkoxy(C$_2$-C$_6$)alkoxy, —CO$_2$H, —CO$_2$(C$_1$-C$_4$)alkyl, —SO$_2$(C$_1$-C$_4$)alkyl, (C$_3$-C$_7$)cycloalkyl, phenyl, 5-6 membered heteroaryl, 9-10 membered heteroaryl, 4-7 membered heterocycloalkyl and (phenyl)(C$_1$-C$_4$ alkyl)amino-, wherein said (C$_3$-C$_7$)cycloalkyl, phenyl, (phenyl)(C$_1$-C$_4$ alkyl)amino-, 5-6 membered heteroaryl, 9-10 membered heteroaryl or 4-7 membered heterocycloalkyl is optionally substituted by 1-3 groups each independently selected from the group consisting of halogen, —CF$_3$, hydroxyl, amino, ((C$_1$-C$_4$)alkyl)amino-, ((C$_1$-C$_4$)alkyl)((C$_1$-C$_4$)alkyl)amino-, (C$_1$-C$_4$)alkyl, phenyl(C$_1$-C$_4$)alkyl-, hydroxy(C$_1$-C$_4$)alkyl and (C$_1$-C$_4$)alkoxy, said (C$_3$-C$_7$)cycloalkyl or 4-7 membered heterocycloalkyl is optionally substituted by 1-3 groups each independently selected from the group consisting of halogen, —CF$_3$, hydroxyl, amino, ((C$_1$-C$_4$)alkyl)amino-, ((C$_1$-C$_4$)alkyl)((C$_1$-C$_4$)alkyl)amino-, (C$_1$-C$_4$)alkyl, phenyl(C$_1$-C$_4$)alkyl-, hydroxy(C$_1$-C$_4$)alkyl-, oxo and (C$_1$-C$_4$)alkoxy, and said aryl or heteroaryl is optionally substituted by 1-3 groups each independently selected from the group consisting of halogen, —CF$_3$, hydroxyl, amino, ((C$_1$-C$_4$)alkyl)amino-, ((C$_1$-C$_4$)alkyl)((C$_1$-C$_4$)alkyl)amino-, (C$_1$-C$_4$)alkyl, phenyl(C$_1$-C$_4$)alkyl-, hydroxy(C$_1$-C$_4$)alkyl- and (C$_1$-C$_4$)alkoxy;

R$^b$ is (C$_1$-C$_6$)alkyl or 4-7 membered heterocycloalkyl, wherein:

said (C$_1$-C$_6$)alkyl is optionally substituted by one or two groups each independently selected from the group consisting of hydroxyl, (C$_1$-C$_6$)alkoxy, (C$_1$-C$_6$)alkoxy(C$_2$-C$_6$)alkoxy, —CO$_2$H, —CO$_2$(C$_1$-C$_4$)alkyl, (C$_1$-C$_4$ alkyl)amino-, (C$_1$-C$_4$ alkyl)(C$_1$-C$_4$ alkyl)amino-, 5-6 membered heteroaryl, and 4-7 membered heterocycloalkyl, wherein said 5-6 membered heteroaryl or 4-7 membered heterocycloalkyl is optionally substituted by 1-3 groups each independently selected from the group consisting of halogen, (C$_1$-C$_4$)alkyl, hydroxy(C$_1$-C$_4$)alkyl and (C$_1$-C$_4$)alkoxy, said 4-7 membered heterocycloalkyl is optionally substituted by 1-3 groups each independently selected from the group consisting of hydroxyl, amino, (C$_1$-C$_4$)alkyl, (C$_1$-C$_4$)alkoxycarbonyl-, hydroxy(C$_1$-C$_4$)alkyl-, oxo and (C$_1$-C$_4$)alkoxy, and R$^c$ is H, (C$_1$-C$_4$)alkoxy or (C$_1$-C$_6$)alkyl;

or R$^b$ and R$^c$ taken together with the nitrogen atom to which they are attached form a 3-7 membered heterocycloalkyl group, optionally containing one or two additional ring heteroatoms each independently selected from nitrogen and oxygen, wherein said 3-7 membered heterocycloalkyl is optionally substituted by 1-3 groups each independently selected from the group consisting of (C$_1$-C$_4$)alkyl, hydroxy, —CO$_2$H and —CO(C$_1$-C$_4$)alkyl;

Z is phenyl or aryl(C$_1$-C$_4$)alkyl-, wherein in the phenyl group or the aryl moiety of the aryl(C$_1$-C$_4$)alkyl-group is substituted by $R^4$, $R^5$, $R^6$ and $R^7$, wherein:

$R^4$ is H, halogen, cyano, (C$_1$-C$_4$)alkyl, halo(C$_1$-C$_4$)alkyl, (C$_1$-C$_4$)alkoxy, phenoxy, phenyl(C$_1$-C$_4$)alkoxy, hydroxyl, hydroxy(C$_1$-C$_4$)alkyl-, or aminocarbonyl, wherein the phenyl moiety of said phenoxy or phenyl (C$_1$-C$_4$)alkoxy- is optionally substituted by 1-3 substituents each independently selected from the group consisting of halogen, —CF$_3$, (C$_1$-C$_4$)alkyl and (C$_1$-C$_4$)alkoxy; and each of $R^5$, $R^6$ and $R^7$ is independently selected from the group consisting of H, hydroxyl, halogen, —CF$_3$, hydroxy(C$_1$-C$_4$)alkyl, (C$_1$-C$_4$)alkyl and (C$_1$-C$_4$)alkoxy; or Z is phenyl or pyridyl, substituted by $R^8$, $R^9$ and $R^{10}$, wherein:

$R^8$ and $R^9$ are located on adjacent atoms and taken together with the atoms to which they are attached form a 5-membered ring containing 1, 2 or 3 heteroatoms each independently selected from N, O and S, which 5-membered ring is substituted by $R^{11}$;

wherein one of $R^{10}$ or $R^{11}$ is H, halogen, cyano, (C$_1$-C$_4$) alkyl, halo(C$_1$-C$_4$)alkyl, (C$_1$-C$_4$)alkoxy, phenoxy, phenyl(C$_1$-C$_4$)alkoxy, hydroxyl, hydroxy(C$_1$-C$_4$)alkyl-, or aminocarbonyl, where the phenyl moiety of said phenoxy or phenyl($C_1$-$C_4$)alkoxy is optionally substituted by 1-3 substituents each independently selected from the group consisting of halogen, —$CF_3$, ($C_1$-$C_4$)alkyl and ($C_1$-$C_4$)alkoxy; and the other of $R^{10}$ or $R^{11}$ is H, hydroxyl, halogen, —$CF_3$, hydroxy($C_1$-$C_4$)alkyl, ($C_1$-$C_4$)alkyl or ($C_1$-$C_4$)alkoxy; or Z is pyrazolyl, having the formula:

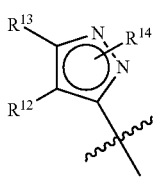

wherein:
$R^{12}$ is H, methyl or hydroxymethyl;
$R^{13}$ is methyl, trifluoromethyl or hydroxymethyl;
$R^{14}$ is H, OH, or ($C_1$-$C_3$)alkyl; or
$R^{12}$ and $R^{13}$, taken together with the atoms to which they are attached, form a 6-membered ring substituted by $R^{15}$ and $R^{16}$, wherein the 6-membered ring optionally contains 1 nitrogen atom;
wherein $R^{15}$ and $R^{16}$ are each independently selected from the group consisting of H, halogen, cyano, ($C_1$-$C_4$) alkyl, halo($C_1$-$C_4$)alkyl, ($C_1$-$C_4$)alkoxy, phenoxy, phenyl($C_1$-$C_4$)alkoxy, hydroxyl, hydroxy($C_1$-$C_4$)alkyl-, and aminocarbonyl, wherein the phenyl moiety of said phenoxy or phenyl($C_1$-$C_4$)alkoxy is optionally substituted by 1-3 substituents each independently selected from the group consisting of halogen, —$CF_3$, ($C_1$-$C_4$) alkyl and ($C_1$-$C_4$)alkoxy;
or a pharmaceutically acceptable salt thereof.

In a further aspect of the present invention, there is provided a compound of formula (I) or a pharmaceutically acceptable salt thereof for use in therapy.

In a further aspect there is provided a compound of formula (I) or a pharmaceutically acceptable salt thereof for use in the treatment of diseases conditions mediated by RIP2 Kinase.

In a further aspect of the present invention, there is provided a pharmaceutical composition comprising a compound of formula (I) or a pharmaceutically acceptable salt thereof and one or more of pharmaceutically acceptable carriers, diluents and excipients.

In a further aspect of the present invention, there is provided a method of treating diseases and conditions mediated by the RIP2 Kinase in a subject comprising administering a therapeutically effective amount of a compound of formula (I) or a pharmaceutically acceptable salt thereof.

In a further aspect of the present invention, there is provided the use of a compound of formula (I), or a pharmaceutically acceptable salt thereof in the manufacture of a medicament for use in treating diseases and conditions mediated by the RIP2 Kinase.

In a further aspect there is provided a combination comprising a compound of formula (I), or a pharmaceutically acceptable salt thereof and at least one further therapeutic agent.

In a further aspect there is provided a combination comprising a compound of formula (I) or a pharmaceutically acceptable salt thereof and at least one further therapeutic agent for use in therapy.

In a further aspect of the present invention, there is provided a pharmaceutical composition comprising a combination comprising a compound of formula (I) or a pharmaceutically acceptable salt thereof and at least one further therapeutic agent and one or more of pharmaceutically acceptable carriers, diluents and excipients.

In a further aspect of the invention there is provided a combination comprising compound of formula (I) or a pharmaceutically acceptable salt thereof and at least one further therapeutic agent for use in treating diseases and conditions mediated by the RIP2 Kinase.

In a further aspect there is provided a method of treating diseases and conditions mediated by the RIP2 Kinase comprising administering to a human in need thereof a therapeutically effective amount of a combination comprising compound of formula (I) or a pharmaceutically acceptable salt thereof, and at least one further therapeutic agent.

In a further aspect there is provided the use of a combination comprising compound of formula (I) or a pharmaceutically acceptable salt thereof and at least one further therapeutic agent in the manufacture of a medicament for treating diseases and conditions mediated by RIP2 Kinase.

In a further aspect there is provided a method of degrading RIP2 kinase comprising administering to a human in need thereof a therapeutically effective amount of a compound of Formula (I) or a pharmaceutically acceptable salt thereof

DETAILED DESCRIPTION OF THE INVENTION

As used herein, "a compound of the invention" includes all solvates, complexes, polymorphs, radiolabelled derivatives, stereoisomers and optical isomers of the compounds of formula (I) and salts thereof.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The compounds of the invention may exist in solid or liquid form. In solid form, compound of the invention may exist in a continuum of solid states ranging from fully amorphous to fully crystalline. The term 'amorphous' refers to a state in which the material lacks long range order at the molecular level and, depending upon the temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compound of formula (I) may exist in solvated and unsolvated forms. As used herein, the term "solvate" refers to a complex of variable stoichiometry formed by a solute (in this invention, a compound of formula (I) or a salt) and a solvent. Such solvents for the purpose of the invention may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice incorporated with water molecules are typically referred to as "hydrates". Hydrates include stoichiometric hydrates as well as compositions containing variable amounts of water. The present invention includes all such solvates.

The compounds of the invention may have the ability to crystallize in more than one form, a characteristic, which is known as polymorphism, and it is understood that such polymorphic forms ("polymorphs") are within the scope of the invention. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

It is also noted that the compounds of formula (I) may form tautomers. It is understood that all tautomers and mixtures of tautomers of the compounds of the present invention are included within the scope of the compounds of the present invention.

The compound of Formula (I) is a Protac targeting RIP Kinase wherein the RIP2 kinase inhibitor is linked via a linker to a IAP binder.

In one embodiment, the present invention provides a Protac targeting RIP2 kinase which is a compound of Formula (II), (III), or (IV):

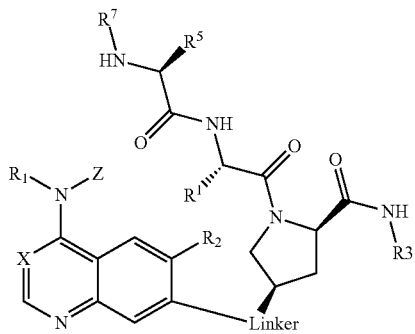

(II)

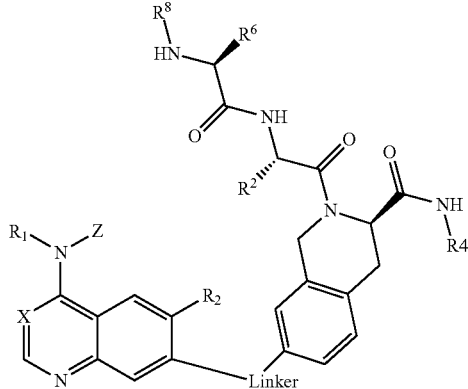

(III)

Substituents in equivalent positions on the IAP binding moiety may be found described in WO 2014/047024 and WO 2014/055461.

In particular, the definitions of $R^1$, Z, X and $R^2$ in the RIP2 inhibitor moiety in the compounds of formula (II) and (III) are as defined in formula (I) above.

The linker is as defined for formula (I) above.

For the IAP binding moiety, in formula (II) and (III)

$R^1$ and $R^2$ are independently optionally substituted alkyl, optionally substituted cycloalkyl, optionally substituted cycloalkylalkyl, optionally substituted arylalkyl, optionally substituted aryl, or $R^1$ and $R^2$ are independently optionally substituted thioalkyl wherein the substituents attached to the S atom of the thioalkyl are optionally substituted alkyl, optionally substituted branched alkyl, optionally substituted heterocyclyl, —(CH2)vCOR$_{20}$, —CH2CHR$_{21}$COR$_{22}$ or —CH$_2$R$_{23}$.

Wherein v-1-3, $R_{10}$ and $R_{22}$ are independently selected from OH, NR$_{24}$R$_{25}$ or OR$_{26}$, $R_{21}$ is NR$_{24}$R$_{25}$, R23 is optionally substituted aryl or optionally substituted heterocyclyl, where the optional substituents include alkyl and halogen, $R_{24}$ is hydrogen or optionally substituted alkyl, $R_{25}$ is hydrogen, optionally substituted alkyl, optionally substituted branched alkyl, optionally substituted arylalkyl, optionally substituted heterocyclyl, —CH2(OCH$_2$CH$_2$O)$_m$CH$_3$, or a polyamine chain, $R_{26}$ is optionally substituted alkyl, w=1-8, Where the optional substituents are OH, halogen or NH$_2$;

$R^3$ and $R^4$ are independently optionally substituted alkyl, optionally substituted cycloalkyl, optionally substituted aryl, optionally substituted arylalkyl, optionally substituted arylalkoxy, optionally substituted heteroaryl, optionally substituted heterocyclyl, optionally substituted heteroarylalkyl or optionally substituted hetercycloalkyl, wherein the substitutents are alkyl, halogen or OH;

$R_5$, $R^6$, $R^7$ and $R^8$ are independently hydrogen, optionally substituted alkyl or optionally substituted cycloalkyl;

$R_9$ is hydrogen, optionally substituted alkyl, optionally substituted cycloalkyl or CO alkyl;

or a pharmaceutically acceptable salt thereof.

(IV)

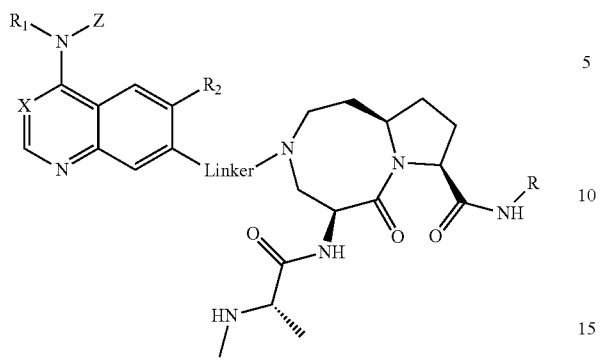

In particular, the definitions of R¹, Z, X and R² in the RIP2 inhibitor moiety in the compounds of formula (IV) are as defined in formula (I) above.

The linker is as defined for formula (I) above.
For the IAP binding moiety, in formula (IV)
R is selected from the group consisting of

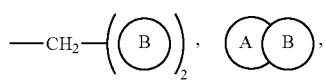

wherein ring A is $C_{4-8}$ aliphatic ring,

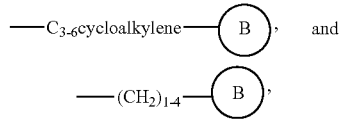

wherein the B ring is aryl or nitrogen atom-containing heteroaryl and the B rings are optionally substituted;
or a pharmaceutically acceptable salt thereof.

In one aspect ring B is phenyl, napthyl, pyridinyl, pyrazinyl or pyrimidinyl.

In one aspect the linker is a straight chain alkyline group of 4-20 carbon atoms wherein one or more carbo atoms one replaced by a group each independently selected from —O—, —NH—, —N(CH₃), —CO—, piperridine, piperazine, pyrimidine, pyridine, phenyl In one aspect in compounds of Formula (I), (II), (III), and (IV), the linker group is a straight chain alkylene group of 4-16 carbon atoms wherein one or more carbon atoms are replaced by a group each independently selected from
—O—, —NH—, —N(CH₃)—, CO,

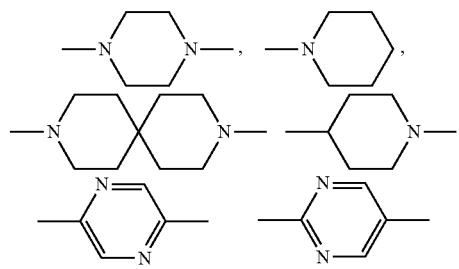

In one aspect the linker is (in the direction RIP2 Kinase inhibitor-IAP inhibitor):
—O(CH₂CH₂O)₃₋₄
—O(Ch₂Ch₂)₄ OCH₂CONH

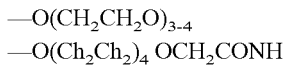

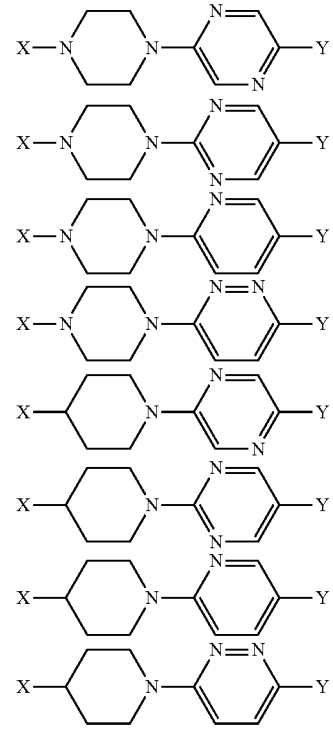

wherein X is —O(CH₂CH₂)₀₋₄,—
and Y is —CONH—, —O— or —CO—.
Examples of linkers include
—(OCH₂CH₂)₄O—
—(OCH₂CH₂)₃O—
—(OCH₂CH₂)₄OCH₂CONH

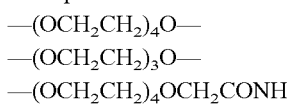

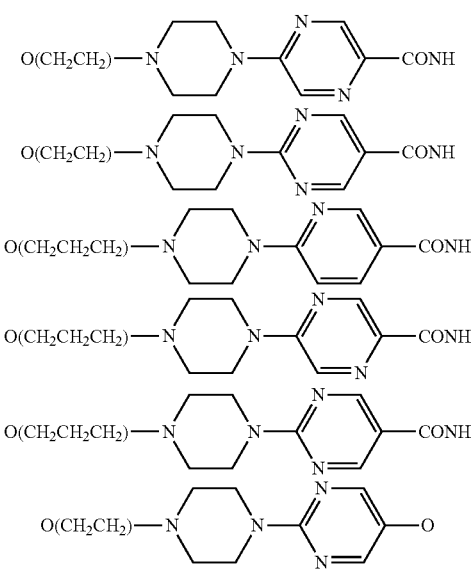

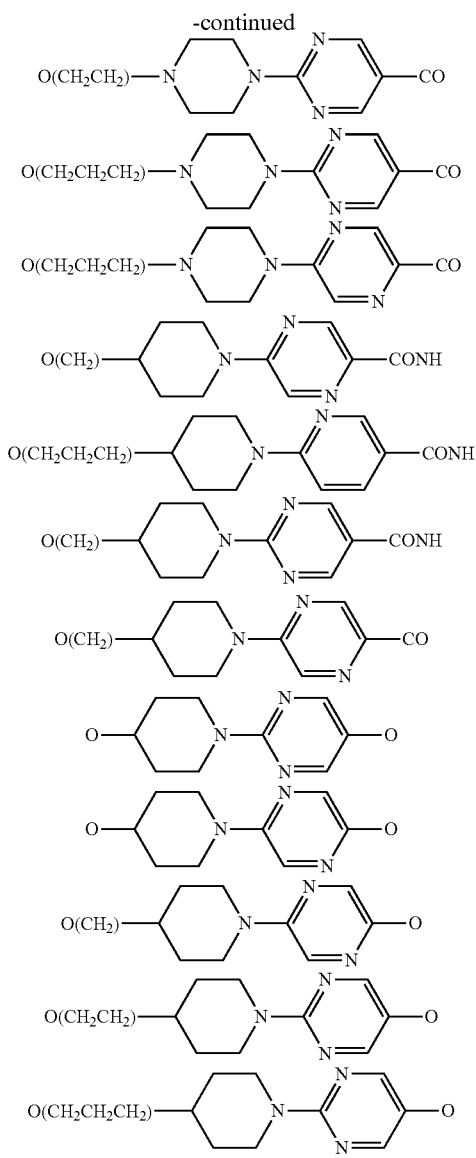

Compounds of Formula (I) include:
- (S)-7-(2-(2-(2-(2-((4-(Benzo[d]thiazol-5-ylamino)-6-(tert-butylsulfonyl)quinolin-7-yl)oxy)ethoxy)ethoxy)ethoxy)-2-((S)-3,3-dimethyl-2-((S)-2-methylamino)propanamido)butanoyl)-N-((R)-1,2,3,4-tetrahydronaphthalen-1-yl)-1,2,3,4-tetrahydroisoquinoline-3-carboxamide,
- (S)-7-(2-(2-(2-(2-((4-(Benzo[d]thiazol-5-ylamino)-6-(tert-butylsulfonyl)quinolin-7-yl)oxy)ethoxy)ethoxy)ethoxy)-2-((S)-3,3-dimethyl-2-((S)-2-(methylamino)propanamido)butanoyl)-N-((S)-1,2,3,4-tetrahydronaphthalen-1-yl)-1,2,3,4-tetrahydroisoquinoline-3-carboxamide,
- (S)-7-(2-(2-(2-(2-((6-(Tert-butylsulfonyl)-4-((4,5-dimethyl-1H-pyrazol-3-yl)amino)quinazolin-7-yl)oxy)ethoxy)ethoxy)ethoxy)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide,
- (2S,4S)-4-(14-((4-(benzo[d]thiazol-5-ylamino)-6-(tert-butylsulfonyl)quinolin-7-yl)oxy)-3,6,9,12-tetraoxatetradecanamido)-1-((S)-3,3-dimethyl-2-((S)-2-(methylamino)propanamido)butanoyl)-N-((R)-3-methylbutan-2-yl)pyrrolidine-2-carboxamide,
- (2S,4S)-4-(14-((4-(benzo[d]thiazol-5-ylamino)-6-(tert-butylsulfonyl)quinolin-7-yl)oxy)-3,6,9,12-tetraoxatetradecanamido)-1-((S)-3,3-dimethyl-2-((S)-2-(methylamino)propanamido)butanoyl)-N-((R)-1,2,3,4-tetrahydronaphthalen-1-yl)pyrrolidine-2-carboxamide,
- (2S,4S)-4-(14-((4-(benzo[d]thiazol-5-ylamino)-6-(tert-butylsulfonyl)quinolin-7-yl)oxy)-3,6,9,12-tetraoxatetradecanamido)-N-((R)-2,3-dihydro-1H-inden-1-yl)-1-((S)-3,3-dimethyl-2-((S)-2-(methylamino)propanamido)butanoyl)pyrrolidine-2-carboxamide,
- (2S,4S)-4-(14-((4-(benzo[d]thiazol-5-ylamino)-6-(tert-butylsulfonyl)quinolin-7-yl)oxy)-3,6,9,12-tetraoxatetradecanamido)-1-((S)-3,3-dimethyl-2-((S)-2-(methylamino)propanamido)butanoyl)-N-((R)-1-phenylpropyl)pyrrolidine-2-carboxamide,
- (2S,4S)-4-(14-((4-(benzo[d]thiazol-5-ylamino)-6-(tert-butylsulfonyl)quinolin-7-yl)oxy)-3,6,9,12-tetraoxatetradecanamido)-N-(2,6-difluorophenyl)-1-((S)-3,3-dimethyl-2-((S)-2-(methylamino)propanamido)butanoyl)pyrrolidine-2-carboxamide,
- (2S,4S)-4-(2-(2-(2-(2-((6-(Tert-butylsulfonyl)-4-((5-fluoro-1H-indazol-3-yl)amino)quinolin-7-yl)oxy)ethoxy)ethoxy)ethoxy)ethoxy)-1-((S)-3,3-dimethyl-2-((S)-2-(methylamino)propanamido)butanoyl)-N-((R)-1,2,3,4-tetrahydronaphthalen-1-yl)pyrrolidine-2-carboxamide,
- (2S,4S)-4-(2-(2-(2-((6-(Tert-butylsulfonyl)-4-((5-fluoro-1H-indazol-3-yl)amino)quinolin-7-yl)oxy)ethoxy)ethoxy)ethoxy)-1-((S)-3,3-dimethyl-2-((S)-2-(methylamino)propanamido)butanoyl)-N-((R)-1,2,3,4-tetrahydronaphthalen-1-yl)pyrrolidine-2-carboxamide,
- 5-(4-(2-((6-(Tert-butylsulfonyl)-4-((4,5-dimethyl-1H-pyrazol-3-yl)amino)quinazolin-7-yl)oxy)ethyl)piperazin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)pyrazine-2-carboxamide,
- 2-(4-(2-((6-(tert-butylsulfonyl)-4-((4,5-dimethyl-1H-pyrazol-3-yl)amino)quinazolin-7-yl)oxy)ethyl)piperazin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)pyrimidine-5-carboxamide
- 5-(4-(((6-(tert-butylsulfonyl)-4-((4,5-dimethyl-1H-pyrazol-3-yl)amino)quinazolin-7-yl)oxy)methyl)piperidin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)pyrazine-2-carboxamide;
- 6-(4-(3-((6-(tert-butylsulfonyl)-4-((4,5-dimethyl-1H-pyrazol-3-yl)amino)quinazolin-7-yl)oxy)propyl)piperidin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)nicotinamide;
- 2-(4-(((6-(tert-butylsulfonyl)-4-((4,5-dimethyl-1H-pyrazol-3-yl)amino)quinazolin-7-yl)oxy)methyl)piperidin-1-yl)-N-((3S,5S)-1-(S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)pyrimidine-5-carboxamide;
- 6-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)nicotinamide;

5-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)pyrazine-2-carboxamide;

2-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)pyrimidine-5-carboxamide;

5-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)pyrazine-2-carboxamide;

(2S,4S)-4-((2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidin-5-yl)oxy)-1-((S)-3,3-dimethyl-2-((S)-2-(methylamino)propanamido)butanoyl)-N-((R)-1,2,3,4-tetrahydronaphthalen-1-yl)pyrrolidine-2-carboxamide, 2-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-5-((2,6-difluorophenyl)carbamoyl)-1-((S)-3,3-dimethyl-2-((S)-2-(methylamino)propanamido)butanoyl)pyrrolidin-3-yl)pyrimidine-5-carboxamide;

2-(4-(2-((6-(tert-butylsulfonyl)-4-((4,5-dimethyl-1H-pyrazol-3-yl)amino)quinazolin-7-yl)oxy)ethyl)piperazin-1-yl)-N-((3S,5S)-1-((S)-2-cyclohexyl-2-((S)-2-(methylamino)propanamido)acetyl)-5-((3-methyl-1-phenyl-1H-pyrazol-5-yl)carbamoyl)pyrrolidin-3-yl)pyrimidine-5-carboxamide;

2-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-1-((S)-2-cyclohexyl-2-((S)-2-(methylamino)propanamido)acetyl)-5-((3-methyl-1-phenyl-1H-pyrazol-5-yl)carbamoyl)pyrrolidin-3-yl)pyrimidine-5-carboxamide;

(S)-7-((6-(4-((6-(Tert-butylsulfonyl)-4-((4,5-dimethyl-1H-pyrazol-3-yl)amino)quinazolin-7-yl)oxy)piperidin-1-yl)pyrimidin-4-yl)oxy)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide;

(S)-7-((6-(4-(((6-(Tert-butylsulfonyl)-4-((4,5-dimethyl-1H-pyrazol-3-yl)amino)quinazolin-7-yl)oxy)methyl)piperidin-1-yl)pyrimidin-4-yl)oxy)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide;

(2S,4S)-4-((2-(4-(((6-(Tert-butylsulfonyl)-4-((4,5-dimethyl-1H-pyrazol-3-yl)amino)quinazolin-7-yl)oxy)methyl)piperidin-1-yl)pyrimidin-5-yl)oxy)-1-((S)-2-cyclohexyl-2-((S)-2-(methylamino)propanamido)acetyl)-N-((R)-1,2,3,4-tetrahydronaphthalen-1-yl)pyrrolidine-2-carboxamide, (2S,4S)-4-((2-(4-((6-(tert-butylsulfonyl)-4-((4,5-dimethyl-1H-pyrazol-3-yl)amino)quinazolin-7-yl)oxy)piperidin-1-yl)pyrimidin-5-yl)oxy)-1-((S)-2-cyclohexyl-2-((S)-2-(methylamino)propanamido)acetyl)-N-((R)-1,2,3,4-tetrahydronaphthalen-1-yl)pyrrolidine-2-carboxamide, (2S,4S)-4-((2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidin-5-yl)oxy)-1-((S)-2-cyclohexyl-2-((S)-2-(methylamino)propanamido)acetyl)-N-((R)-1,2,3,4-tetrahydronaphthalen-1-yl)pyrrolidine-2-carboxamide, (2S,4S)-4-((2-(4-(2-((6-(tert-butylsulfonyl)-4-((4,5-dimethyl-1H-pyrazol-3-yl)amino)quinazolin-7-yl)oxy)ethyl)piperidin-1-yl)pyrimidin-5-yl)oxy)-1-((S)-2-cyclohexyl-2-((S)-2-(methylamino)propanamido)acetyl)-N-((R)-1,2,3,4-tetrahydronaphthalen-1-yl)pyrrolidine-2-carboxamide, (2S,4S)-4-((2-(4-(3-((6-(tert-butylsulfonyl)-4-((4,5-dimethyl-1H-pyrazol-3-yl)amino)quinazolin-7-yl)oxy)propyl)piperidin-1-yl)pyrimidin-5-yl)oxy)-1-((S)-2-cyclohexyl-2-((S)-2-(methylamino)propanamido)acetyl)-N-((R)-1,2,3,4-tetrahydronaphthalen-1-yl)pyrrolidine-2-carboxamide, (2S,4S)-4-((2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidin-5-yl)oxy)-1-((S)-3,3-dimethyl-2-((S)-2-(methylamino)propanamido)butanoyl)-N-((R)-1,2,3,4-tetrahydronaphthalen-1-yl)pyrrolidine-2-carboxamide (2S,4S)-4-((2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidin-5-yl)oxy)-N-(2,6-difluorophenyl)-1-((S)-3,3-dimethyl-2-((S)-2-(methylamino)propanamido)butanoyl)pyrrolidine-2-carboxamide 2-(4-(2-((6-(Tert-butylsulfonyl)-4-((4,5-dimethyl-1H-pyrazol-3-yl)amino)quinazolin-7-yl)oxy)ethyl)piperazin-1-yl)-N-((3S,5S)-5-((2,6-difluorophenyl)carbamoyl)-1-((S)-3,3-dimethyl-2-((S)-2-(methylamino)propanamido)butanoyl)pyrrolidin-3-yl)pyrimidine-5-carboxamide;

5-(4-(3-((6-(Tert-butylsulfonyl)-4-((4,5-dimethyl-1H-pyrazol-3-yl)amino)quinazolin-7-yl)oxy)propylpiperazin-1-yl)-N-((3S,5S)-5-((2,6-difluorophenyl)carbamoyl)-1-((S)-3,3-dimethyl-2-((S)-2-(methylamino)propanamido)butanoyl)pyrrolidin-3-yl)pyrazine-2-carboxamide (S)-1-((S)-2-(1-(2-(4-(2-((6-(Tert-butylsulfonyl)-4-((4,5-dimethyl-1H-pyrazol-3-yl)amino)quinazolin-7-yl)oxy)ethyl)piperazin-1-yl)pyrimidine-5-carbonyl)piperidin-4-yl)-2-((S)-2-(methylamino)propanamido)acetyl)-N-((R)-1,2,3,4-tetrahydronaphthalen-1-yl)pyrrolidine-2-carboxamide;

(S)-1-((S)-2-(1-(2-(4-(3-((6-(tert-butylsulfonyl)-4-((4,5-dimethyl-1H-pyrazol-3-yl)amino)quinazolin-7-yl)oxy)propylpiperazin-1-yl)pyrimidine-5-carbonyl)piperidin-4-yl)-2-((S)-2-(methylamino)propanamido)acetyl)-N-((R)-1,2,3,4-tetrahydronaphthalen-1-yl)pyrrolidine-2-carboxamide;

(5S,8S,10aR)-N-Benzhydryl-3-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)-5-((S)-2-(methylamino)propanamido)-6-oxodecahydropyrrolo[1,2-a][1,5]diazocine-8-carboxamide;

(5S,8S,10aR)-3-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)-5-((S)-2-(methylamino)propanamido)-6-oxo-N-((R)-1,2,3,4-tetrahydronaphthalen-1-yl)decahydropyrrolo[1,2-a][1,5]diazocine-8-carboxamide;

(5S,8S,10aR)-3-(5-(4-(3-((6-(tert-butylsulfonyl)-4-((4,5-dimethyl-1H-pyrazol-3-yl)amino)quinazolin-7-yl)oxy)propyl)piperazin-1-yl)pyrazine-2-carbonyl)-5-((S)-2-(methylamino)propanamido)-6-oxo-N-((R)-1,2,3,4-tetrahydronaphthalen-1-yl)decahydropyrrolo[1,2-a][1,5]diazocine-8-carboxamide;

(5S,8S,10aR)-3-(2-(4-(3-((6-(tert-butylsulfonyl)-4-((4,5-dimethyl-1H-pyrazol-3-yl)amino)quinazolin-7-yl)oxy)propyl)piperazin-1-yl)pyrimidine-5-carbonyl)-5-((S)-2-(methylamino)propanamido)-6-oxo-N-((R)-1,2,3,4-tetrahydronaphthalen-1-yl)decahydropyrrolo[1,2-a][1,5]diazocine-8-carboxamide;

and pharmaceutically acceptable salts thereof

The compounds of Formula (I) may be in the form of a salt.

Typically, the salts of the present invention are pharmaceutically acceptable salts. Salts encompassed within the term "pharmaceutically acceptable salts" refer to non-toxic salts of the compounds of this invention. For a review on suitable salts see Berge et al, J. Pharm. Sci. 1977, 66, 1-19.

Suitable pharmaceutically acceptable salts can include acid addition salts.

A pharmaceutically acceptable acid addition salt can be formed by reaction of a compound of formula (I) with a suitable inorganic or organic acid (such as hydrobromic, hydrochloric, sulfuric, nitric, phosphoric, p-toluenesulfonic, benzenesulfonic, methanesulfonic, ethanesulfonic, naphthalenesulfonic such as 2-naphthalenesulfonic), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, p-toluenesulfonate, benzenesulfonate, methanesulfonate, ethanesulfonate, naphthalenesulfonate (e.g. 2-naphthalenesulfonate) salt.

In one aspect the salt is a hydrochloride salt.

Other non-pharmaceutically acceptable salts, e.g. trifluoroacetates, may be used, for example in the isolation of compounds of the invention, and are included within the scope of this invention.

The invention includes within its scope all possible stoichiometric and non-stoichiometric forms of the compounds of formula (I).

While it is possible that, for use in therapy, the compound of the invention may be administered as the raw chemical, it is possible to present the compound of the invention as the active ingredient as a pharmaceutical composition. Such compositions can be prepared in a manner well known in the pharmaceutical art and comprise at least one active compound. Accordingly, the invention further provides pharmaceutical compositions comprising a compound of the invention and one or more pharmaceutically acceptable excipients. The excipient(s) must be acceptable in the sense of being compatible with the other ingredients of the composition and not deleterious to the recipient thereof. In accordance with another aspect of the invention there is also provided a process for the preparation of a pharmaceutical composition including the agent, or pharmaceutically acceptable salts thereof, with one or more pharmaceutically acceptable excipients. The pharmaceutical composition can be for use in the treatment and/or prophylaxis of any of the conditions described herein.

Generally, the compound of the invention is administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

Pharmaceutical compositions may be presented in unit dose forms containing a predetermined amount of active ingredient per unit dose. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions.

Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert excipient such as ethanol, glycerol, water and the like. Powders are prepared by reducing the compound to a suitable fine size and mixing with a similarly prepared pharmaceutical excipient such as an edible carbohydrate, as, for example, starch or mannitol. Flavouring, preservative, dispersing and colouring agent can also be present.

Capsules are made by preparing a powder mixture, as described above, and filling formed gelatin sheaths. Excipients including glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, excipients including suitable binders, glidants, lubricants, sweetening agents, flavours, disintegrating agents and colouring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, suspensions, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like.

The compounds of the invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories, rectal foams, rectal gels or as enemas.

Dosage forms for nasal or inhaled administration may conveniently be formulated as aerosols, solutions, suspensions drops, gels or dry powders.

Pharmaceutical compositions adapted for vaginal administration may be presented as pessaries, tampons, creams, gels, pastes, foams or spray formulations.

Pharmaceutical compositions adapted for parental administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

In one aspect the pharmaceutical composition is is suitable for oral or rectal administration for non systemic or local delivery to the GI tract, or is formulated for subcutaneous delivery.

A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or more usually in a number (such as two, three, four, five or six) of sub-doses per day such that the total daily dose is the same.

Suitably, the amount of the compound of the invention administered according to the present invention will be an amount selected from 0.01 mg to 1 g per day (calculated as the free or unsalted compound).

The compounds of formula (I) and pharmaceutically acceptable salts thereof may be employed alone or in combination with other therapeutic agents. The compounds of formula (I) and pharmaceutically acceptable salts thereof and the other pharmaceutically active agent(s) may be administered together or separately and, when administered separately, administration may occur simultaneously or sequentially, in any order. by any convenient route in separate or combined pharmaceutical compositions.

The amounts of the compound(s) of formula (I) or pharmaceutically acceptable salt(s) thereof and the other pharmaceutically active agent(s) and the relative timings of administration will be selected in order to achieve the desired combined therapeutic effect. The compounds of the present invention and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the invention is administered first and the other second and visa versa. Such sequential administration may be close in time (e.g. simultaneously) or remote in time. Furthermore, it does not matter if the compounds are administered in the same dosage form, e.g. one compound may be administered topically and the other compound may be administered orally. Suitably, both compounds are administered orally.

The combinations may be presented as a combination kit. By the term "combination kit" "or kit of parts" as used herein is meant the pharmaceutical composition or compositions that are used to administer the combination according to the invention. When both compounds are administered simultaneously, the combination kit can contain both compounds in a single pharmaceutical composition, such as a tablet, or in separate pharmaceutical compositions. When the compounds are not administered simultaneously, the combination kit will contain each compound in separate pharmaceutical compositions either in a single package or in separate pharmaceutical compositions in separate packages.

The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited, For example, one agent may be administered once a day, and the other agent may be administered 2 or 3 times a day, or one agent may be administered once a week, and the other agent may be administered once a day and the like.

It will be clear to a person skilled in the art that, where appropriate, the other therapeutic ingredients(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When the compound of formula (I) is used in combination with a second therapeutic agent active against the same disease, condition or disorder, the dose of each compound may differ from that when the compound is used alone. Appropriate doses will be readily appreciated by those skilled in the art.

In one embodiment the mammal in the methods and uses of the present invention is a human.

The compounds of the invention may be particularly useful for treatment of RIP2 kinase-mediated diseases or disorders, particularly inflammatory disorders.

In one aspect the disease or condition is inflammation. This invention also provides a compound of Formula (I), or a salt thereof, particularly a pharmaceutically acceptable salt thereof, for use in therapy. This invention specifically provides for the use of a compound of Formula (I), or a pharmaceutically acceptable salt thereof, as an active therapeutic substance in the treatment of a RIP2 kinase-mediated disease or disorder, for example the diseases and disorders recited herein; more specifically, for use in the treatment of a disease mediated by inhibition of RIP2 kinase.

The invention also provides for the use of a compound of Formula (I), or a salt thereof, particularly a pharmaceutically acceptable salt thereof, in the manufacture of a medicament for use in the treatment of a RIP2 kinase-mediated disease or disorder, for example the diseases and disorders recited herein.

In a further aspect there is provided a combination comprising a compound of formula (I) or a pharmaceutically acceptable salt thereof and at least one further therapeutic agent useful in the treatment of a disease mediated by inhibition of RIP2 kinase In a further aspect there is provided a combination comprising a compound of formula (I) or a pharmaceutically acceptable salt thereof and at least one further therapeutic agent useful in the treatment of a disease mediated by inhibition of RIP2 kinase for use in therapy.

In a further aspect there is provided a combination comprising a compound of formula (I) or pharmaceutically acceptable salt thereof and at least one one further therapeutic agent useful in the treatment of allergic disease, inflammation or autoimmune disease, for use in the treatment a disease mediated by inhibition of RIP2 kinase.

In a further aspect there is provided the use of a combination comprising a compound of formula (I) or a pharmaceutically acceptable salt thereof and at least one one further therapeutic agent useful in the treatment of allergic disease, inflammation or autoimmune disease in the manufacture of a medicament for the treatment of a disease mediated by inhibition of RIP2 kinase In a further aspect there is provided a method of treating allergic disease, inflammation or autoimmune disease comprising administering to a human in need thereof a therapeutically effective amount of a combination comprising a compound of formula (I) or a pharmaceutically acceptable salt thereof and at least one further therapeutic agent useful in the treatment of a disease mediated by inhibition of RIP2 kinase.

In a further aspect there is provided a pharmaceutical composition comprising a combination comprising a compound of formula (I) or a pharmaceutically acceptable salt thereof and at least one further therapeutic agent useful in the treatment of a disease mediated by inhibition of RIP2 kinase and one or more of pharmaceutically acceptable excipients.

Inflammation represents a group of vascular, cellular and neurological responses to trauma. Inflammation can be characterised as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterised by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self tissues.

The aim of anti-inflammatory therapy is therefore to reduce this inflammation, to inhibit autoimmunity when present and to allow for the physiological process or healing and tissue repair to progress.

The compound of formula (I) may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knew, ankle, and foot, and conditions affecting tissues connecting muscles to bones such as tendons. Examples of musculoskeletal inflammation which may be treated with compounds of formula (I) include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular inflammation refers to inflammation of any structure of the eye, including the eye lids. Examples of ocular inflammation which may be treated with the compounds of formula (I) include blepharitis, blepharochalasis, conjunctivitis, dacryoadenitis, keratitis, keratoconjunctivitis sicca (dry eye), scleritis, trichiasis, and uveitis.

Examples of inflammation of the nervous system which may be treated with the compounds of formula (I) include encephalitis, Guillain-Barre syndrome, meningitis, neuromyotonia, narcolepsy, multiple sclerosis, myelitis and schizophrenia.

Examples of inflammation of the vasculature or lymphatic system which may be treated with the compounds of formula (I) include arthrosclerosis, arthritis, phlebitis, vasculitis, and lymphangitis.

Examples of inflammatory conditions of the digestive system which may be treated with the compounds of formula (I) include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with the compounds of formula (I) include cervicitis, chorioamnionitis, endometritis, epididymitis, omphalitis, oophoritis, orchitis, salpingitis, tubo-ovarian abscess, urethritis, vaginitis, vulvitis, and vulvodynia.

The compound of formula (I) may be used to treat autoimmune conditions having an inflammatory component. Such conditions include acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schönlein purpura, Kawasaki's disease, lupus erythematosus, microscopic colitis, microscopic polyarteritis, mixed connective tissue disease, multiple sclerosis, myasthenia gravis, opsocionus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

The compound of formula (I) may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celliac disease).

Other inflammatory conditions which may be treated with the agents include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosis, psoriasis, chronic obstructive pulmonary disease, and inflammation accompanying infectious conditions (e.g., sepsis).

Treatment of RIP2 kinase-mediated diseases or disorders, or more broadly, treatment of immune mediated diseases including, but not limited to, allergic diseases, autoimmune diseases, prevention of transplant rejection and the like, may be achieved using a compound of this invention as a monotherapy, or in dual or multiple combination therapy, with or include one or more other therapeutic agents, for example selected from NSAIDS, corticosteroids, COX-2 inhibitors, cytokine inhibitors, anti-TNF agents, inhibitors oncostatin M, anti-malarials, immunsuppressive and cytostatics.

This invention also provides a compound of Formula (I), or a salt thereof, particularly a pharmaceutically acceptable salt thereof, for use in therapy. This invention specifically provides for the use of a compound of Formula (I), or a pharmaceutically acceptable salt thereof, as an active therapeutic substance in the treatment of a RIP2 kinase-mediated disease or disorder, for example the diseases and disorders recited herein; more specifically, for use in the treatment of a disease mediated by inhibition of RIP2 kinase.

The invention also provides for the use of a compound of Formula (I), or a salt thereof, particularly a pharmaceutically acceptable salt thereof, in the manufacture of a medicament for use in the treatment of a RIP2 kinase-mediated disease or disorder, for example the diseases and disorders recited herein.

In a further aspect there is provided a combination comprising a compound of formula (I) or a pharmaceutically acceptable salt thereof and at least one further therapeutic agent useful in the treatment of a disease mediated by inhibition of RIP2 kinase In a further aspect there is provided a combination comprising a compound of formula (I) or a pharmaceutically acceptable salt thereof and at least one further therapeutic agent useful in the treatment of a disease mediated by inhibition of RIP2 kinase for use in therapy.

In a further aspect there is provided a combination comprising a compound of formula (I) or pharmaceutically acceptable salt thereof and at least one one further therapeutic agent useful in the treatment of allergic disease, inflammation or autoimmune disease, for use in the treatment a disease mediated by inhibition of RIP2 kinase.

In a further aspect there is provided the use of a combination comprising a compound of formula (I) or a pharmaceutically acceptable salt thereof and at least one one further therapeutic agent useful in the treatment of allergic disease, inflammation or autoimmune disease in the manufacture of a medicament for the treatment of a disease mediated by inhibition of RIP2 kinase In a further aspect there is provided a method of treating allergic disease, inflammation or autoimmune disease comprising administering to a human in need thereof a therapeutically effective amount of a combination comprising a compound of formula (I) or a pharmaceutically acceptable salt thereof and at least one further therapeutic agent useful in the treatment of a disease mediated by inhibition of RIP2 kinase.

In a further aspect there is provided a pharmaceutical composition comprising a combination comprising a compound of formula (I) or a pharmaceutically acceptable salt thereof and at least one further therapeutic agent useful in the treatment of a disease mediated by inhibition of RIP2 kinase and one or more of pharmaceutically acceptable excipients.

General Synthetic Methods

Compounds of general formula (I) may be prepared by methods known in the art of organic synthesis. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, $3^{rd}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I).

In particular, methods for preparing IAP compounds included in the present invention can be found in WO 2014/047024, WO 2014/055461, WO 2014/031487 and WO 2008/128171

Methods for preparing RIP2 inhibitors included in the present invention can be found in WO 2014/128622, WO 2014/043437, WO 2013/025958, WO 2012/122011, WO 2012/021580 and WO 2011/140442.

Experimental

Abbreviations

DCM: dichloromethane.
DIPEA: N, N-diisopropylethylamine.
DMF: N, N-dimethylformamide.
hr.: hour.
HATU: 2-(7-aza-1H-benzotriazole-1-yl)-1,1,3,3-tetramethyluronium hexafluorophosphate.
HPLC: high-performance liquid chromatography.
LCMS: liquid chromatography-mass spectrometry
Min: minutes.
NMP: N-methylpyrrolidone.
NMR: Nuclear magnetic resonance.
RT: retention time.
tBu: tert-butoxide.
TFA: trifluoroacetic acid.
THF: tetrahydrofuran.
LCMS Method A:

Unless specified, Method A was used for analysis.

The analysis was conducted on an Acquity UPLC BEH C18 column (50 mm×2.1 mm internal diameter 1.7 μm packing diameter) at 40° C.

The solvents employed were:

A=0.1% v/v solution of formic acid in water.
B=0.1% v/v solution of formic acid in acetonitrile.

The gradient employed was as follows:

| Time (minutes) | Flow Rate (mL/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

LCMS Method B:

The analysis was conducted on an Acquity UPLC BEH C18 column (50 mm×2.1 mm internal diameter 1.7 μm packing diameter) at 40° C.

The solvents employed were:
A=10 mM ammonium bicarbonate in water adjusted to pH 10 with ammonia solution.
B=acetonitrile.
The gradient employed was as follows:

| Time (minutes) | Flow Rate (mL/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 99 | 1 |

The UV detection was an averaged signal from wavelength of 210 nm to 350 nm and mass spectra were recorded on a mass spectrometer using alternate-scan positive and negative mode electrospray ionization.
LCMS Method C:
The analysis was conducted on an Acquity UPLC CSH C18 column (50 mm×2.1 mm internal diameter 1.7 μm packing diameter) at 40° C.
The solvents employed were:
A=0.1% v/v solution of trifluoroacetic acid in water.
B=0.1% v/v solution of trifluoroacetic acid in acetonitrile.
The gradient employed was as follows:

| Time (minutes) | Flow Rate (mL/min) | % A | % B |
|---|---|---|---|
| 0 | 1 | 95 | 5 |
| 1.5 | 1 | 5 | 95 |
| 1.9 | 1 | 5 | 95 |
| 2.0 | 1 | 95 | 5 |

The UV detection was an averaged signal from wavelength of 210 nm to 350 nm and mass spectra were recorded on a mass spectrometer using alternate-scan positive and negative mode electrospray ionization.

The following illustrates the mobile phases and gradients used when compounds underwent purification by mass-directed autopreparative HPLC.
Mass-Directed Autopreparative HPLC (Formic Acid Modifier)
The HPLC analysis was conducted on a Sunfire C18 column (150 mm×30 mm internal diameter, 5 μm packing diameter) at ambient temperature.
The solvents employed were:
A=0.1% v/v solution of formic acid in water.
B=0.1% v/v solution of formic acid in acetonitrile.
Mass-Directed Autopreparative HPLC (Trifluoroacetic Acid Modifier)
The HPLC analysis was conducted on a Sunfire C18 column (150 mm×30 mm internal diameter, 5 μm packing diameter) at ambient temperature.
The solvents employed were:
A=0.1% v/v solution of trifluoroacetic acid in water.
B=0.1% v/v solution of trifluoroacetic acid in acetonitrile.
Mass-Directed Autopreparative HPLC (Ammonium Bicarbonate Modifier)
The HPLC analysis was conducted on an XBridge C18 column (150 mm×30 mm internal diameter, 5 μm packing diameter) at ambient temperature.
The solvents employed were:
A=10 mM ammonium bicarbonate in water adjusted to pH 10 with ammonia solution.
B=acetonitrile.

For each of the mass-directed autopreparative purifications, irrespective of the modifier used, the gradient employed was dependent upon the retention time of the particular compound undergoing purification as recorded in the analytical LCMS, and was as follows:
For compounds with an analytical LCMS retention time below 0.6 minutes the following gradient was used:

| Time (minutes) | Flow Rate (mL/min) | % A | % B |
|---|---|---|---|
| 0 | 40 | 99 | 1 |
| 1 | 40 | 99 | 1 |
| 10 | 40 | 70 | 30 |
| 11 | 40 | 1 | 99 |
| 15 | 40 | 1 | 99 |

For compounds with an analytical LCMS retention time between 0.6 and 0.9 minutes the following gradient was used:

| Time (minutes) | Flow Rate (mL/min) | % A | % B |
|---|---|---|---|
| 0 | 40 | 85 | 15 |
| 1 | 40 | 85 | 15 |
| 10 | 40 | 45 | 55 |
| 11 | 40 | 1 | 99 |
| 15 | 40 | 1 | 99 |

For compounds with an analytical LCMS retention time between 0.9 and 1.2 minutes the following gradient was used:

| Time (minutes) | Flow Rate (mL/min) | % A | % B |
|---|---|---|---|
| 0 | 40 | 70 | 30 |
| 1 | 40 | 70 | 30 |
| 10 | 40 | 15 | 85 |
| 11 | 40 | 1 | 99 |
| 15 | 40 | 1 | 99 |

For compounds with an analytical LCMS retention time between 1.2 and 1.4 minutes the following gradient was used:

| Time (minutes) | Flow Rate (mL/min) | % A | % B |
|---|---|---|---|
| 0 | 40 | 50 | 50 |
| 1 | 40 | 50 | 50 |
| 10 | 40 | 1 | 99 |
| 11 | 40 | 1 | 99 |
| 15 | 40 | 1 | 99 |

For compounds with an analytical LCMS retention time greater than 1.4 minutes (LCMS method A) or greater than 3.6 minutes (LCMS method B) the following gradient was used:

| Time (minutes) | Flow Rate (mL/min) | % A | % B |
|---|---|---|---|
| 0 | 40 | 20 | 80 |
| 1 | 40 | 20 | 80 |
| 10 | 40 | 1 | 99 |

| Time (minutes) | Flow Rate (mL/min) | % A | % B |
|---|---|---|---|
| 11 | 40 | 1 | 99 |
| 15 | 40 | 1 | 99 |

The UV detection was an averaged signal from wavelength of 210 nm to 350 nm and mass spectra were recorded on a mass spectrometer using alternate-scan positive and negative mode electrospray ionization.

The chemical names were generated using ChemBioDraw Ultra v12 from CambridgeSoft.

(S)-Tert-butyl 7-hydroxy-3-(((R)-1,2,3,4-tetrahydronaphthalen-1-yl)carbamoyl)-3,4-dihydroisoquinoline-2(1H)-carboxylate

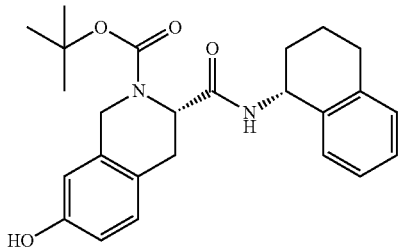 [SMILES: CC(C)(C)OC(=O)N1Cc2cc(O)ccc2C[C@H]1C(=O)N[C@@H]1CCCc2ccccc21]

A mixture of (S)-2-(tert-butoxycarbonyl)-7-hydroxy-1,2,3,4-tetrahydroisoquinoline-3-carboxylic acid (commercially available from, for example, Fluorochem) (1 g, 3.41 mmol) and (R)-1,2,3,4-tetrahydronaphthalen-1-amine (commercially available from, for example, Aldrich) (0.552 g, 3.8 mmol) in DMF (4 mL) was treated with DIPEA (1.8 mL, 10.2 mmol) and then with HATU (1.56 g, 4.1 mmol) and stirred at ambient temperature for 30 minutes. The mixture was treated with dichloromethane (60 mL), saturated aqueous sodium bicarbonate (10 mL) and water (10 mL) and separated through a hydrophobic frit. The organic phase was evaporated to dryness and the product was purified by chromatography on silica using a gradient elution from 0% to 100% ethyl acetate in cyclohexane to afford the title compound (1.18 g, 2.8 mmol, 82% yield). LCMS RT=1.10 min, ES+ve 423.

(S)-7-Hydroxy-N-((R-1,2,3,4-tetrahydronaphthalen-1-yl)-1,2,3,4-tetrahydroisoquinoline-3-carboxamide, Hydrochloride

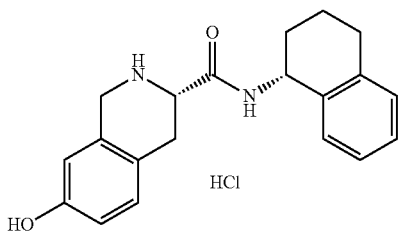 [SMILES: O=C(N[C@@H]1CCCc2ccccc21)[C@@H]1Cc2ccc(O)cc2CN1 ; Cl]

A solution of (S)-tert-butyl 7-hydroxy-3-(((R)-1,2,3,4-tetrahydronaphthalen-1-yl)carbamoyl)-3,4-dihydroisoquinoline-2(1H)-carboxylate (1.18 g, 2.8 mmol) in tetrahydrofuran (10 mL) was treated with hydrochloric acid (4M in 1,4-dioxan) (10 mL, 40 mmol) and the mixture was stood at ambient temperature overnight. The mixture was removed of solvent in vacuo to afford the title compound (943 mg, 2.6 mmol, 94% yield). LCMS RT=0.58 min, ES+ve 323.

Tert-butyl ((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)carbamate

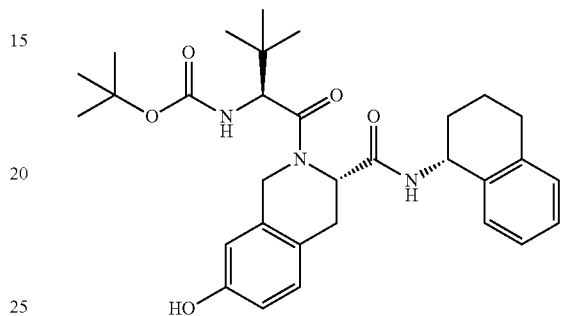

A mixture of (S)-7-hydroxy-N-((R)-1,2,3,4-tetrahydronaphthalen-1-yl)-1,2,3,4-tetrahydroisoquinoline-3-carboxamide, hydrochloride (933 mg, 2.6 mmol) and (S)-2-((tert-butoxycarbonyl)amino)-3,3-dimethylbutanoic acid (631 mg, 2.7 mmol) in DMF (10 mL) was treated with DIPEA (1.82 mL, 10.4 mmol) and then with HATU (1.19 g, 3.12 mmol) and stirred at ambient temperature for 1 hour. The mixture was treated with dichloromethane (80 mL), saturated aqueous sodium bicarbonate (10 mL) and water (10 mL) and separated through a hydrophobic frit. The organic phase was evaporated to dryness and the product was purified by chromatography on silica using a gradient elution from 0% to 100% ethyl acetate in cyclohexane to afford the title compound (923 mg, 1.72 mmol, 66% yield). LCMS RT=1.27 min, ES+ve 536.

(S)-2-((S)-2-Amino-3,3-dimethylbutanoyl)-7-hydroxy-N-((R)-1,2,3,4-tetrahydronaphthalen-1-yl)-1,2,3,4-tetrahydroisoquinoline-3-carboxamide, Hydrochloride

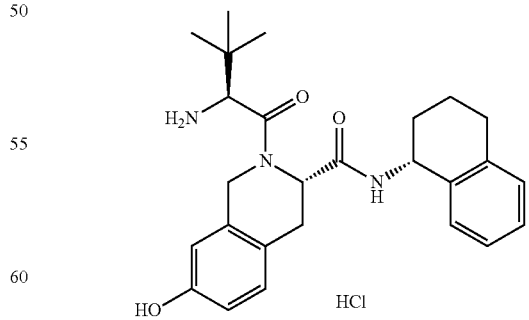

A solution of tert-butyl ((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl) carbamate (915 mg, 1.71 mmol) in tetrahydrofuran (4 mL)

was treated with hydrochloric acid (4M in 1,4-dioxan) (5 mL, 20 mmol) and then stirred at ambient temperature overnight. The mixture was evaporated to dryness to afford the title compound (780 mg, 1.65 mmol, 97% yield). LCMS RT=0.69 min, ES+ve 436.

Tert-butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate

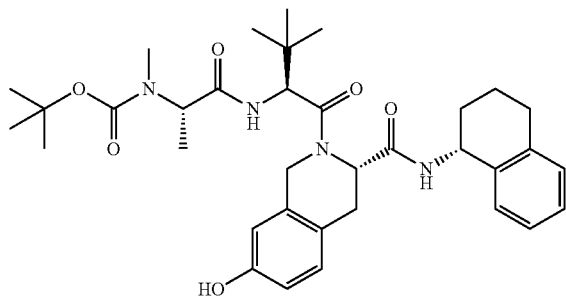 [SMILES: C[C@@H](C(=O)N[C@H](C(=O)N1Cc2cc(O)ccc2C[C@H]1C(=O)N[C@@H]1CCCc2ccccc21)C(C)(C)C)N(C)C(=O)OC(C)(C)C]

A mixture of (S)-2-((S)-2-amino-3,3-dimethylbutanoyl)-7-hydroxy-N-((R)-1,2,3,4-tetrahydronaphthalen-1-yl)-1,2,3,4-tetrahydroisoquinoline-3-carboxamide, hydrochloride (770 mg, 1.63 mmol) and (S)-2-((tert-butoxycarbonyl)(methyl)amino)propanoic acid (332 mg, 1.63 mmol) in DMF (4 mL) was treated with DIPEA (1.14 mL, 6.5 mmol) and then with HATU (744 mg, 2.0 mmol) and stirred at ambient temperature overnight. The product was purified by chromatography on silica using a gradient elution from 0% to 100% ethyl acetate in cyclohexane to afford the title compound (780 mg, 1.26 mmol, 77% yield). LCMS RT=1.29 min, ES+ve 621.

Tert-butyl ((S)-1-(((S)-1-((S)-7-(2-(2-(2-(2-chloroethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate

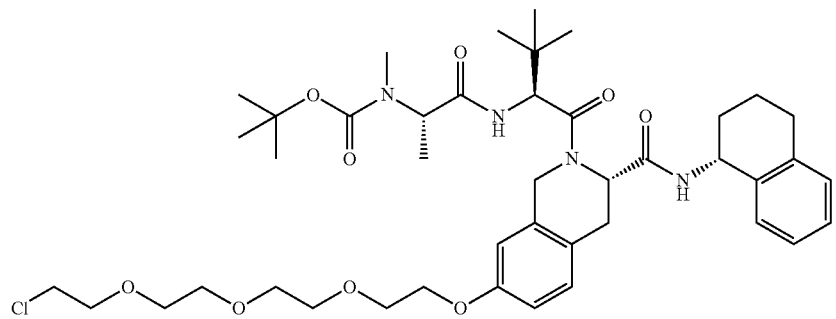 [SMILES: C[C@@H](C(=O)N[C@H](C(=O)N1Cc2cc(OCCOCCOCCOCCCl)ccc2C[C@H]1C(=O)N[C@@H]1CCCc2ccccc21)C(C)(C)C)N(C)C(=O)OC(C)(C)C]

A solution of tert-butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (200 mg, 0.32 mmol) in DMF (4 mL) was treated with 1-chloro-2-(2-(2-(2-chloroethoxy)ethoxy)ethoxy)ethane (commercially available from, for example, Aldrich) (298 mg, 1.3 mmol) and potassium carbonate (134 mg, 1.0 mmol) and heated at 80° C. overnight. The product was subjected directly to purification by mass-directed automated preparative HPLC (formic acid modifier) to afford the title compound (165 mg, 0.20 mmol, 63% yield). LCMS RT=1.44 min, ES+ve 816.

5-(((4-Bromo-3-methoxyphenyl)amino)methylene)-2,2-dimethyl-1,3-dioxane-4,6-dione

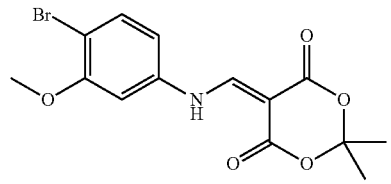

2,2-Dimethyl-1,3-dioxane-4,6-dione (8.5 g, 58 mmol) in trimethyl orthoformate (50 mL, 450 mmol) was refluxed at 105° C. for 1 hr. 4-Bromo-3-methoxyaniline (commercially available from, for example, Aldrich) (10.5 g, 50 mmol) was then added and refluxing was continued for an additional hour. The suspension was filtered, and the solid was washed with methanol and vacuum dried to yield the title compound (17.0 g, 49 mmol, 96% yield). LCMS RT=1.10 min, ES+ve 356,358

6-Bromo-7-methoxyquinolin-4-ol

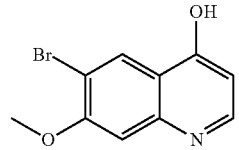

To diphenyl ether (68 mL, 420 mmol) at 230° C. was added 5-({[4-bromo-3-(methyloxy)phenyl]amino}methylidene)-2,2-dimethyl-1,3-dioxane-4,6-dione (15 g, 42 mmol), and the mixture was stirred for 1 hr. The reaction mixture was poured into hexane after being cooled to room temperature. The precipitate was filtered and washed with hexane. The brown solid was dried under vacuum overnight to afford the title compound (10.0 g, 33 mmol, 79% yield). LCMS RT=0.63 min, ES+ve 254,256

6-Bromo-4-chloro-7-methoxyquinoline

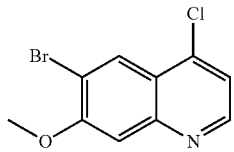

6-Bromo-7-(methyloxy)-4-quinolinol (4.17 g, 16.4 mmol) in phosphorus oxychloride (8 mL, 82 mmol) was stirred at 110° C. for 1 hr. The reaction mixture was cooled and cautiously poured into saturated aqueous sodium carbonate with ice while stirring. The resulting suspension was filtered, the solid was washed with water and vacuum-dried overnight to yield the title compound (4.6 g, 16 mmol, 97% yield). LCMS RT=1.18 min, ES+ve 272,274

6-(Tert-butylthio)-4-chloro-7-methoxyquinoline

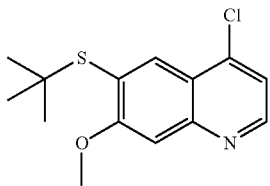 [SMILES: COc1cc2nccc(Cl)c2cc1SC(C)(C)C]

A mixture of 6-bromo-4-chloro-7-methoxyquinoline (50 g, 183 mmol), Pd(PPh₃)₄ (5.30 g, 4.59 mmol), sodium carbonate (48.6 g, 459 mmol) and 1,4-dioxane (895 mL) was purged with nitrogen for 10 minutes. 2-Methyl-2-propanethiol (22.8 mL, 202 mmol) was added and the reaction was heated at 70° C. for 4 d. The reaction was cooled to rt and flushed through a silica gel plug that had been pre-wetted with EtOAc using 100% EtOAc as the eluent. The product-containing fractions were combined and triturated with MeOH to afford the title compound (37.5 g, 128 mmol, 70% yield). LCMS RT=1.31 min, ES+ve 282

6-(Tert-butylsulfonyl)-4-chloro-7-methoxyquinoline

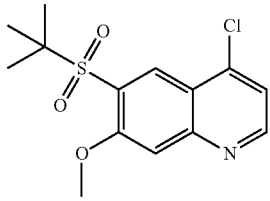 [SMILES: COc1cc2nccc(Cl)c2cc1S(=O)(=O)C(C)(C)C]

(Tert-butylthio)-4-chloro-7-methoxyquinoline (18.5 g, 63 mmol) in ethyl acetate (315 mL) and water (315 mL) was treated with Oxone® (44.6 g, 72.5 mmol) and stirred at rt for 18 hours. The mixture was separated and the aqueous phase was extracted twice with ethyl acetate. The combined organic extracts were concentrated to dryness. The residue was dissolved in a minimal amount of 10% methanol/dichloromethane, loaded onto a 340 g pre-packed silica cartridge and purified via column chromatography (100% ethyl acetate, then 0-20% methanol in ethyl acetate). Product-containing fractions were evaporated to dryness and triturated with EtOAc to yield the title compound (15.2 g, 48 mmol, 77% yield). LCMS RT=0.97 min, ES+ve 314

N-(6-(Tert-butylsulfonyl)-7-methoxyquinolin-4-yl)benzo[d]thiazol-5-amine

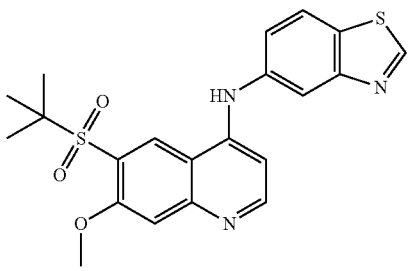 [SMILES: COc1cc2nccc(Nc3ccc4scnc4c3)c2cc1S(=O)(=O)C(C)(C)C]

A mixture of 6-(tert-butylsulfonyl)-4-chloro-7-methoxyquinoline (2 g, 6.4 mmol) and benzo[d]thiazol-5-amine (0.957 g, 6.4 mmol) in ethanol (10 mL) was irradiated by microwave at 150° C. for 15 mins. The cooled reaction mixture was partitioned between ethyl acetate and saturated sodium bicarbonate. The aqueous layer was extracted with EtOAc twice and the combined EtOAc layers were dried over magnesium sulfate, filtered and evaporated to dryness. The residue was purified via flash chromatography (100 g pre-packed silica cartridge) using a gradient elution from 0-75% ethyl acetate/cyclohexane to yield the title compound (2.11 g, 4.9 mmol, 77% yield). LCMS RT=0.58 min, ES+ve 428

4-(Benzo[d]thiazol-5-ylamino)-6-(tert-butylsulfonyl)quinolin-7-ol

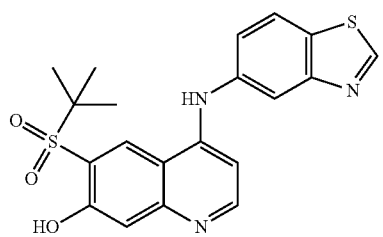 [SMILES: CC(C)(C)S(=O)(=O)c1cc2c(Nc3ccc4scnc4c3)ccnc2cc1O]

To a solution of N-(6-(tert-butylsulfonyl)-7-methoxyquinolin-4-yl)benzo[d]thiazol-5-amine hydrochloride (5.35 g, 11.5 mmol) in DMF (50 mL) was added sodium propane-2-thiolate (5.66 g, 58 mmol). The reaction was then heated to 150° C. for 1 hour. It was cooled to rt and concentrated under vacuum. The residue was treated with ethanol (70 mL) and stirred at 60° C. for 15 minutes, cooled in ice then the yellow precipitated product was filtered off, washed with minimum ethanol and dried under vacuum to afford the title compound (4.55 g, 11 mmol, 95% yield). LCMS RT=0.57 min, ES+ve 414

Tert-butyl 14-((4-(benzo[d]thiazol-5-ylamino)-6-(tert-butylsulfonyl)quinolin-7-yl)oxy)-3,6,9,12-tetraoxatetradecan-1-oate

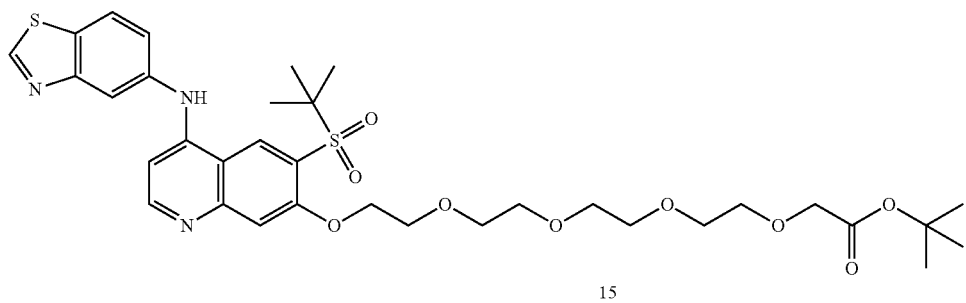

A solution of tert-butyl 14-(tosyloxy)-3,6,9,12-tetraoxatetradecan-1-oate (1.35 g, 2.9 mmol) in DMF (2.5 mL) was added to a stirred solution of 4-(benzo[d]thiazol-5-ylamino)-6-(tert-butylsulfonyl)quinolin-7-ol (802 mg, 1.94 mmol) and caesium carbonate (948 mg, 2.91 mmol) in DMF (2.5 mL). The reaction mixture was stirred at 50° C. for 16 hours. The reaction mixture was then partitioned between EtOAc (150 mL) and water (150 mL). The organic layer was separated, washed with water (50 mL), brine (50 mL), dried using a hydrophobic frit and concentrated under reduced pressure. The sample was purified using a C18-silica column (120 g) using a gradient elution from 5-95% acetonitrile in water with 0.1% formic acid to afford the title compound. LCMS RT=0.80 min, ES+ve 704.

14-((4-(Benzo[d]thiazol-5-yl)amino)-6-(tert-butylsulfonyl)quinolin-7-yl)oxy)-3,6,9,12-tetraoxatetradecan-1-oic acid

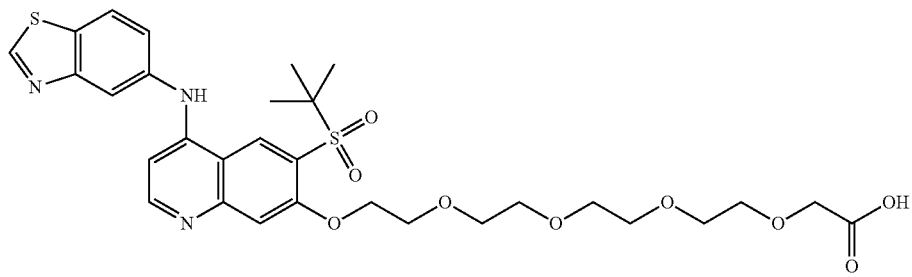 [SMILES: CC(C)(C)S(=O)(=O)c1cc2c(Nc3ccc4scnc4c3)ccnc2cc1OCCOCCOCCOCCOCC(=O)O]

Trifluoroacetic acid (0.49 mL, 6.4 mmol) was added to a solution of tert-butyl 14-((4-(benzo[d]thiazol-5-ylamino)-6-(tert-butylsulfonyl)quinolin-7-yl)oxy)-3,6,9,12-tetraoxatetradecan-1-oate (90 mg, 0.13 mmol) in THF (1 mL) and stirred for 6 hours. The reaction mixture was diluted with DCM (20 mL) and concentrated under reduced pressure three times and then repeated using toluene as the solvent to afford the title compound (78 mg, 0.12 mmol, 94% yield). LCMS RT=0.62 min, ES+ve 648.

(2S,4S)-1-Tert-butyl 2-methyl 4-(14-((4-(benzo[d]thiazol-5-ylamino)-6-(tert-butylsulfonyl)quinolin-7-yl)oxy)-3,6,9,12-tetraoxatetradecanamido)pyrrolidine-1,2-dicarboxylate

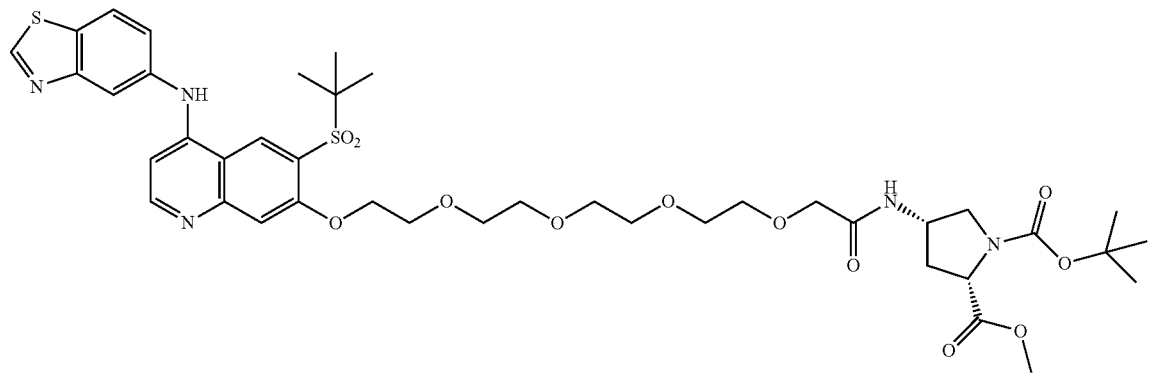 [SMILES: COC(=O)[C@@H]1C[C@H](NC(=O)COCCOCCOCCOCCOc2cc3nccc(Nc4ccc5scnc5c4)c3cc2S(=O)(=O)C(C)(C)C)CN1C(=O)OC(C)(C)C]

HATU (678 mg, 1.78 mmol) was added to a mixture of 14-((4-(benzo[d]thiazol-5-ylamino)-6-(tert-butylsulfonyl)quinolin-7-yl)oxy)-3,6,9,12-tetraoxatetradecan-1-oic acid (1.05 g, 1.62 mmol), (2S,4S)-1-tert-butyl 2-methyl 4-aminopyrrolidine-1,2-dicarboxylate, hydrochloride (592 mg, 2.1 mmol), DIPEA (0.85 mL, 4.9 mmol), and DMF (10 mL). The reaction was stirred at ambient temperature for 30 min. The reaction mixture was then diluted with water (50 mL) and extracted using ethyl acetate (2×50 mL). The organic solution was then washed once with 50% brine solution (50 mL) and once with brine (50 mL). The solution was then concentrated under reduced pressure and purified using a 120 g C-18/silica column using a gradient of 10-95% acetonitrile in water with 0.1% formic acid modifier to afford the title compound (759 mg, 0.87 mmol, 54% yield). LCMS RT=0.79 min, ES+ve 874.

(2S,4S)-Methyl 4-(14-((4-(benzo[d]thiazol-5-ylamino)-6-(tert-butylsulfonyl)quinolin-7-yl)oxy)-3,6,9,12-tetraoxatetradecanamido)pyrrolidine-2-carboxylate, Hydrochloride

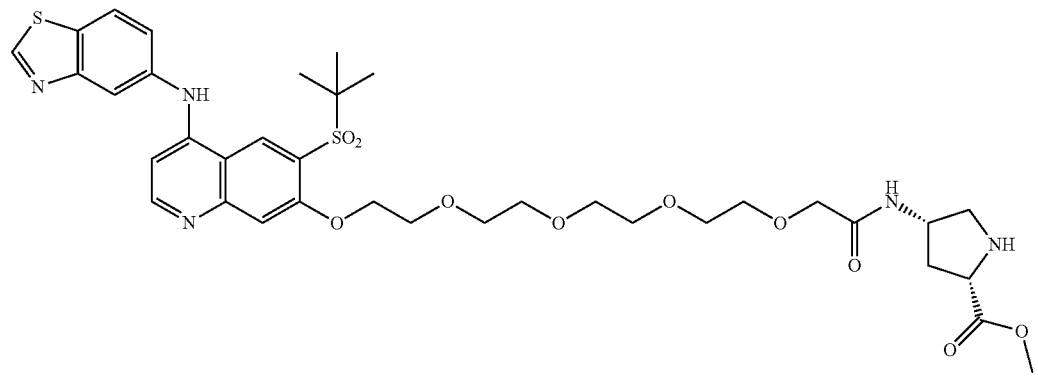 [SMILES: COC(=O)[C@@H]1C[C@H](NC(=O)COCCOCCOCCOCCOc2cc3nccc(Nc4ccc5scnc5c4)c3cc2S(=O)(=O)C(C)(C)C)CN1]

Hydrochloric acid (4M in dioxane) (0.65 mL, 2.6 mmol) was added to (2S,4S)-1-tert-butyl 2-methyl 4-(14-((4-(benzo[d]thiazol-5-ylamino)-6-(tert-butylsulfonyl)quinolin-7-yl)oxy)-3,6,9,12-tetraoxatetradecanamido)pyrrolidine-1,2-dicarboxylate (76 mg, 0.087 mmol) in DCM (0.5 mL), and the mixture was stirred at room temperature for 45 min. The solvent was removed under reduced pressure, and the residue was re-evaporated with DCM (3×20 mL) followed by toluene (20 mL) to afford the title product (72 mg, 0.089 mmol, 100% yield). LCMS RT=0.49 min, ES+ve 774.

(2S,4S)-methyl 4-(14-((4-(benzo[d]thiazol-5-ylamino)-6-(tert-butylsulfonyl)quinolin-7-yl)oxy)-3,6,9,12-tetraoxatetradecanamido)-1-((S)-2-((S)-2-((tert-butoxycarbonyl)(methyl)amino)propanamido)-3,3-dimethylbutanoyl)pyrrolidine-2-carboxylate

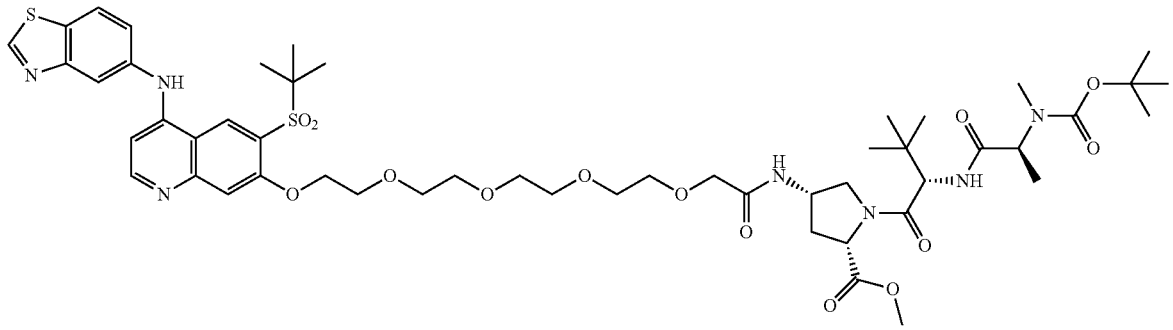 [SMILES: COC(=O)[C@@H]1C[C@H](NC(=O)COCCOCCOCCOCCOc2cc3nccc(Nc4ccc5scnc5c4)c3cc2S(=O)(=O)C(C)(C)C)CN1C(=O)[C@@H](NC(=O)[C@H](C)N(C)C(=O)OC(C)(C)C)C(C)(C)C]

HATU (351 mg, 0.92 mmol) was added to a mixture of (2S,4S)-methyl 4-(14-((4-(benzo[d]thiazol-5-ylamino)-6-(tert-butylsulfonyl)quinolin-7-yl)oxy)-3,6,9,12-tetraoxatetradecanamido)pyrrolidine-2-carboxylate (650 mg, 0.84 mmol), (S)-2-((S)-2-((tert-butoxycarbonyl)(methyl)amino)propanamido)-3,3-dimethylbutanoic acid (345 mg, 1.1 mmol), DIPEA (0.44 mL, 2.5 mmol), and DMF (10 mL). The reaction mixture was stirred at ambient temperature for 3 hr. The mixture was diluted with water (50 mL) and the product extracted using ethyl acetate (2×50 mL). This organic fraction was washed first with 50% brine solution (75 mL) and then with brine (75 mL). The solution was passed through a hydrophobic frit and concentrated under reduced pressure. The sample was purified using a 120 g C18-Silica column using a gradient elution from 10-95% acetonitrile in water and 0.1% formic acid modifier to afford the title compound (517 mg, 0.48 mmol, 57% yield). LCMS RT=0.89 min, ES+ve 537.

(2S,4S)-4-(14-((4-(Benzo[d]thiazol-5-ylamino)-6-(tert-butylsulfonyl)quinolin-7-yl)oxy)-3,6,9,12-tetraoxatetradecanamido)-1-((S)-2-((S)-2-((tert-butoxycarbonyl)(methyl)amino)propanamido)-3,3-dimethylbutanoyl)pyrrolidine-2-carboxylic Acid

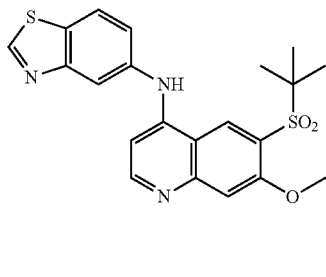
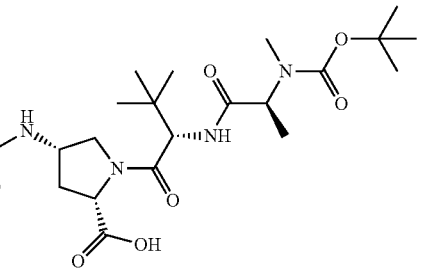

To a solution of (2S,4S)-methyl 4-(14-((4-(benzo[d]thiazol-5-ylamino)-6-(tert-butylsulfonyl)quinolin-7-yl)oxy)-3,6,9,12-tetraoxatetradecanamido)-1-((S)-2-((S)-2-((tert-butoxycarbonyl)(methyl)amino)propanamido)-3,3-dimethylbutanoyl)pyrrolidine-2-carboxylate (517 mg, 0.48 mmol) in THF (2.5 mL) was added 2M aqueous sodium hydroxide (2.4 mL, 4.8 mmol). The reaction mixture was stirred at ambient temperature for 1.5 h. The pH of the solution was adjusted to about 2 using 0.1 M hydrochloric acid solution. The mixture was then partitioned between ethyl acetate (50 mL) and water (50 mL). The aqueous layer was washed once with a further portion of ethyl acetate (50 mL), the two organic fractions were then combined and washed first with 50% brine solution (75 mL) and then with brine (75 mL). The organic solution was passed through a hydrophobic frit and concentrated under reduced pressure to afford the title compound (503 mg, 0.48 mmol, 99% yield). LCMS RT=0.93 min, ES+ve 1059.

Tert-butyl ((S)-1-(((S)-1-((2S,4S)-4-(14-((4-(benzo[d]thiazol-5-ylamino)-6-(tert-butylsulfonyl)quinolin-7-yl)oxy)-3,6,9,12-tetraoxatetradecanamido)-2-(((R)-3-methylbutan-2-yl)carbamoyl)pyrrolidin-1-yl)-3,3-dimethyl-1-oxobutan-2-yl)amino)-1-oxopropan-2-yl)(methyl)carbamate

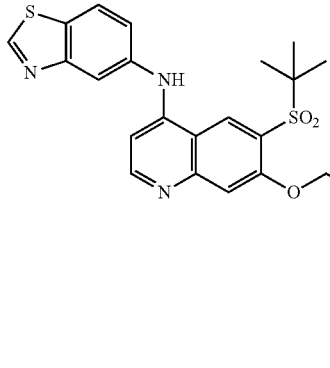
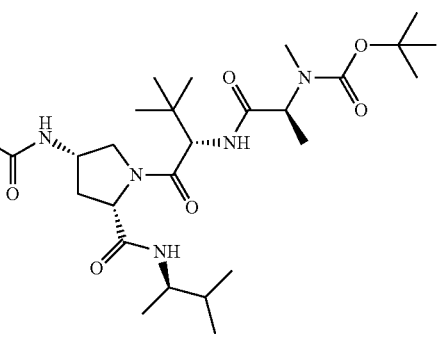

HATU (17.4 mg, 0.046 mmol) was added to a mixture of (2S,4S)-4-(14-((4-(benzo[d]thiazol-5-ylamino)-6-(tert-butylsulfonyl)quinolin-7-yl)oxy)-3,6,9,12-tetraoxatetradecanamido)-1-((S)-2-((S)-2-((tert-butoxycarbonyl)(methyl)amino)propanamido)-3,3-dimethylbutanoyl)pyrrolidine-2-carboxylic acid (44 mg, 0.042 mmol), (R)-3-methylbutan-2-amine (6.3 µl, 0.054 mmol), DIPEA (0.022 mL, 0.13 mmol), in DMF (1 mL). The reaction mixture was stirred at ambient temperature for 18 hr then directly loaded onto a 30 g C18-Silica column and purified using a gradient from 10-95% acetonitrile in water with a 0.1% formic acid modifier to afford the title compound (20.4 mg, 0.018 mmol, 44% yield). LCMS RT=1.33 min, ES+ve 1127.

The following compounds were prepared by a method analogous to that for tert-butyl ((S)-1-(((S)-1-((2S,4S)-4-(14-((4-(benzo[d]thiazol-5-ylamino)-6-(tert-butylsulfonyl)quinolin-7-yl)oxy)-3,6,9,12-tetraoxatetradecanamido)-2-(((R)-3-methylbutan-2-yl)carbamoyl)pyrrolidin-1-yl)-3,3-dimethyl-1-oxobutan-2-yl)amino)-1-oxopropan-2-yl)(methyl)carbamate:

| Compound Name/Structure | Yield | LCMS RT | ES + ve |
|---|---|---|---|
| Tert-butyl ((S)-1-(((S)-1-((2S,4S)-4-(14-((4-(benzo[d]thiazol-5-ylamino)-6-(tert-butylsulfonyl)quinolin-7-yl)oxy)-3,6,9,12-tetraoxatetradecanamido)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate | 49% | Method B 1.38 mins | 594 (M + 2H)2+ |

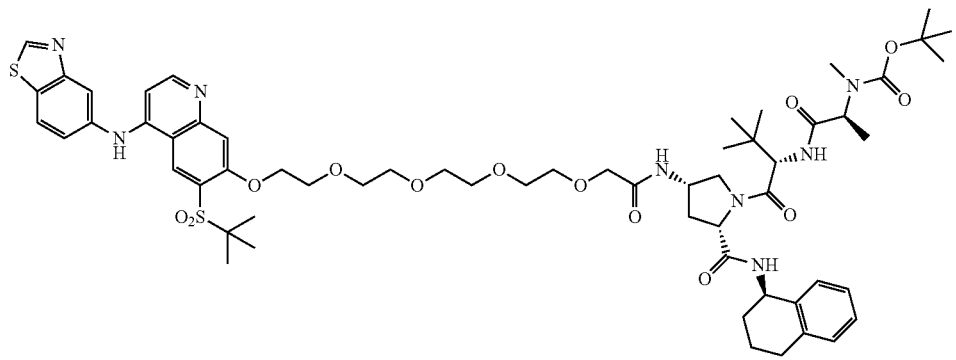 [SMILES: C[C@@H](C(=O)N[C@H](C(=O)N1C[C@@H](NC(=O)COCCOCCOCCOCCOc2cc3nccc(Nc4ccc5scnc5c4)c3cc2S(=O)(=O)C(C)(C)C)C[C@H]1C(=O)N[C@@H]1CCCc2ccccc21)C(C)(C)C)N(C)C(=O)OC(C)(C)C]

| Tert-butyl ((S)-1-(((S)-1-((2S,4S)-4-(14-((4-(benzo[d]thiazol-5-ylamino)-6-(tert-butylsulfonyl)quinolin-7-yl)oxy)-3,6,9,12-tetraoxatetradecanamido)-2-(((R)-2,3-dihydro-1H-inden-1-yl)carbamoyl)pyrrolidin-1-yl)-3,3-dimethyl-1-oxobutan-2-yl)amino)-1-oxopropan-2-yl)(methyl)carbamate | 36% | Method B 1.33 mins | 1173 |

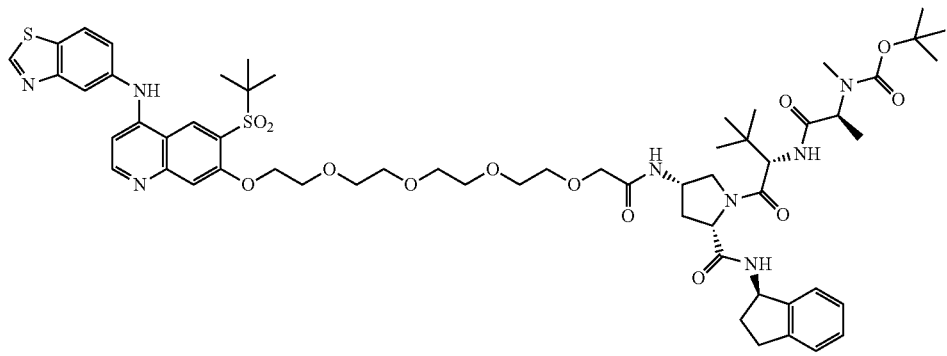 [SMILES: C[C@@H](C(=O)N[C@H](C(=O)N1C[C@@H](NC(=O)COCCOCCOCCOCCOc2cc3nccc(Nc4ccc5scnc5c4)c3cc2S(=O)(=O)C(C)(C)C)C[C@H]1C(=O)N[C@@H]1CCc2ccccc21)C(C)(C)C)N(C)C(=O)OC(C)(C)C]

| Tert-butyl ((S)-1-(((S)-1-((2S,4S)-4-(14-((4-(benzo[d]thiazol-5-ylamino)-6-(tert-butylsulfonyl)quinolin-7-yl)oxy)-3,6,9,12-tetraoxatetradecanamido)-2-(((R)-1-phenylpropyl)carbamoyl)pyrrolidin-1-yl)-3,3-dimethyl-1-oxobutan-2-yl)amino)-1-oxopropan-2-yl)(methyl)carbamate | 40% | Method B 1.34 mins | 1175 |

| Compound Name/Structure | Yield | LCMS RT | ES + ve |
|---|---|---|---|

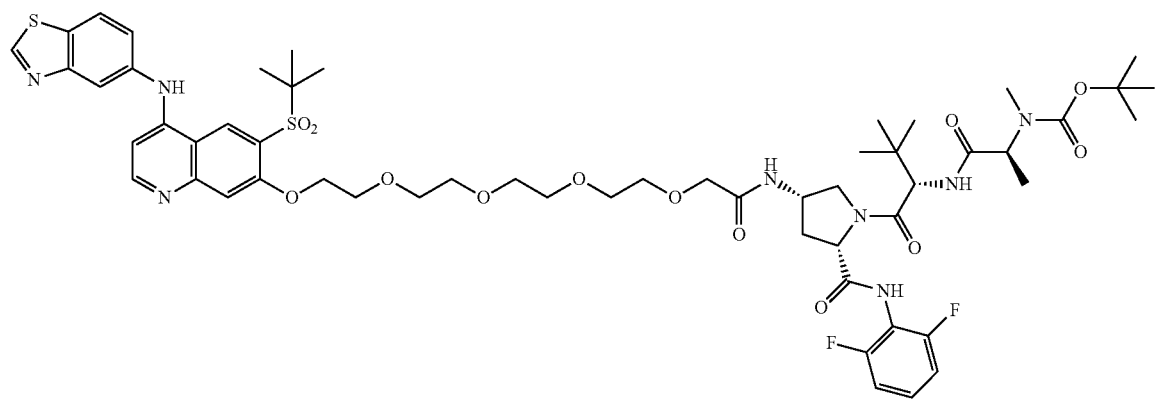 [SMILES: C[C@@H](C(=O)N[C@H](C(=O)N1C[C@@H](NC(=O)COCCOCCOCCOCCOc2cc3nccc(Nc4ccc5scnc5c4)c3cc2S(=O)(=O)C(C)(C)C)C[C@H]1C(=O)Nc1c(F)cccc1F)C(C)(C)C)N(C)C(=O)OC(C)(C)C]

Tert-butyl ((S)-1-(((S)-1-((2S,4S)-4-(14-((4-(benzo[d]thiazol-5-ylamino)-6-(tert-butylsulfonyl)quinolin-7-yl)oxy)-3,6,9,12-tetraoxatetradecanamido)-2-((2,6-difluorophenyl)carbamoyl)pyrrolidin-1-yl)-3,3-dimethyl-1-oxobutan-2-yl)amino)-1-oxopropan-2-yl)(methyl)carbamate To a solution of (2S,4S)-4-(14-((4-(benzo[d]thiazol-5-ylamino)-6-(tert-butylsulfonyl)quinolin-7-yl)oxy)-3,6,9,12-tetraoxatetradecanamido)-1-((S)-2-((S)-2-((tert-butoxycarbonyl)(methyl)amino)propanamido)-3,3-dimethylbutanoyl)pyrrolidine-2-carboxylic acid (50 mg, 0.047 mmol) and 2,6-difluoroaniline (6.1 μl, 0.057 mmol) in pyridine (5 mL) at 0° C. was added phosphoryl trichloride (7 μl, 0.071 mmol). The reaction was warmed to rt and stirred for 2 h. The mixture was evaporated to dryness, water (30 mL) was added and the resulting mixture was extracted with EtOAc (2×30 mL). The combined organic layer was washed with water (50 mL), brine (50 mL), passed through a hydrophobic frit and concentrated under vacuum. The crude material was purified using mass directed auto-preparative HPLC to afford the title compound (27 mg, 0.023 mmol, 49% yield). LCMS RT=1.26 min, ES+ve 1169.

6-(Tert-butylsulfonyl)-N-(5-fluoro-1H-indazol-3-yl)-7-methoxyquinolin-4-amine

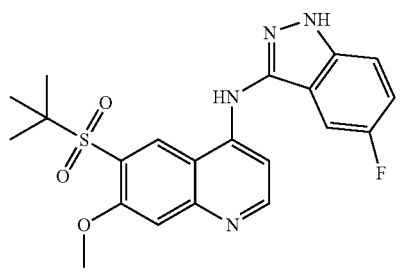 [SMILES: COc1cc2nccc(Nc3n[nH]c4ccc(F)cc34)c2cc1S(=O)(=O)C(C)(C)C]

A mixture of 6-(tert-butylsulfonyl)-4-chloro-7-methoxyquinoline (200 mg, 0.64 mmol) and 5-fluoro-1H-indazol-3-amine (106 mg, 0.70 mmol) was taken up in ethanol (3 mL) and 3 drops of conc HCl were added. The reaction mixture was stirred at rt overnight, then concentrated and the residue was purified by flash chromatography (gradient elution from 0-10% MeOH (with 1% NH4OH) in DCM). Concentration

6-(Tert-butylsulfonyl)-4-((5-fluoro-1H-indazol-3-yl)amino)quinolin-7-ol

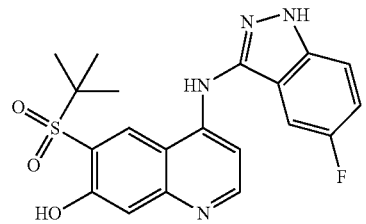 [SMILES: CC(C)(C)S(=O)(=O)c1cc2c(Nc3n[nH]c4ccc(F)cc34)ccnc2cc1O]

To a solution of 6-(tert-butylsulfonyl)-N-(5-fluoro-1H-indazol-3-yl)-7-methoxyquinolin-4-amine (2 g, 4.7 mmol) in DMF (30 mL) was added sodium 2-methylpropane-2-thiolate (2.62 g, 23.3 mmol). The reaction was then heated to 150° C. for 1 hour. It was then cooled to rt and concentrated under vacuum. The residue was purified by flash chromatography (0→15% MeOH with 1% NH$_4$OH in DCM). Desired fractions were combined and concentrated to afford 6-(tert-butylsulfonyl)-4-((5-fluoro-1H-indazol-3-yl)amino)quinolin-7-ol (1.22 g, 2.9 mmol, 63 yield). LCMS RT=0.61 min, ES+ve 415.

6-(Tert-butylsulfonyl)-7-(2-(2-(2-(2-chloroethoxy)ethoxy)ethoxy)ethoxy)-N-(5-fluoro-1H-indazol-3-yl)quinolin-4-amine

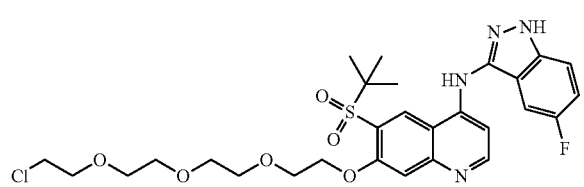 [SMILES: CC(C)(C)S(=O)(=O)c1cc2c(Nc3n[nH]c4ccc(F)cc34)ccnc2cc1OCCOCCOCCOCCCl]

To a solution of 6-(tert-butylsulfonyl)-4-((5-fluoro-1H-indazol-3-yl)amino)quinolin-7-ol (100 mg, 0.24 mmol) in N-methyl-2-pyrrolidone (NMP) (1.0 mL) was added 1-chloro-2-(2-(2-(2-chloroethoxy)ethoxy)ethoxy)ethane (167 mg, 0.72 mmol), sodium iodide (3.6 mg, 0.024 mmol) and potassium carbonate (100 mg, 0.72 mmol) and the reaction mixture was sealed and stirred at 95° C. in a Biotage microwave for 1 hour. The product was purified by flash chromatography (30 g pre-packed C-18 SNAP cartridge using a gradient from 30%-85% acetonitrile (with 0.1% ammonia) in water (10 mM ammonium bicarbonate)). Desired fractions were combined and concentrated to afford the title compound (90 mg, 0.15 mmol, 62% yield). LCMS Method B RT=1.08 min, ES+ve 609.

(S)-Methyl 2-((S)-2-((tert-butoxycarbonyl)(methyl)amino)propanamido)-3,3-dimethylbutanoate

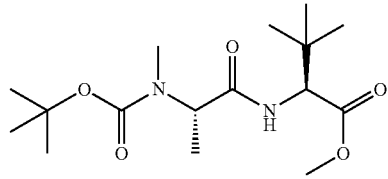 [SMILES: COC(=O)[C@@H](NC(=O)[C@H](C)N(C)C(=O)OC(C)(C)C)C(C)(C)C]

A mixture of (S)-2-((tert-butoxycarbonyl)(methyl)amino)propanoic acid (2.8 g, 13.8 mmol) and (S)-methyl 2-amino-3,3-dimethylbutanoate, hydrochloride (2.52 g, 13.9 mmol) in THF (160 mL) was treated with 1-ethyl-3-(3-dimethyl-aminopropyl)carbodiimide (5.28 g, 27.6 mmol) and HOBt (2.38 g, 15.6 mmol). The mixture was stirred at ambient temperature for 18 hours and then treated with water (50 mL) and ethyl acetate (75 mL). The organic phase was washed with 1M HCl (70 mL×2), saturated sodium bicarbonate (100 mL) and brine (50 mL), dried over magnesium sulfate, filtered and evaporated to dryness to afford the title compound (4.11 g, 12.4 mmol, 90% yield). LCMS RT=1.13 min, ES+ve 331.

(S)-2-((S)-2-(Tert-butoxycarbonyl)(methyl)amino)propanamido)-3,3-dimethylbutanoic Acid

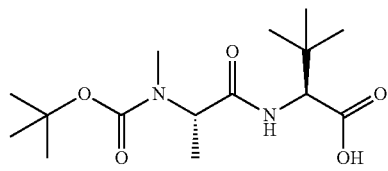 [SMILES: C[C@@H](C(=O)N[C@H](C(=O)O)C(C)(C)C)N(C)C(=O)OC(C)(C)C]

A solution of (S)-methyl 2-((S)-2-((tert-butoxycarbonyl)(methyl)amino)propanamido)-3,3-dimethylbutanoate (4.11 g, 12.4 mmol) in a mixture of THF (40 mL), methanol (20 mL) and water (40 mL) was treated with a solution of lithium hydroxide (1.19 g, 50 mmol) in water (30 mL) and then stirred at ambient temperature for 18 hours. The mixture was treated with 1M HCl (150 mL) and extracted with ethyl acetate (3×50 mL), washed with brine (80 mL), dried over magnesium sulfate and evaporated to dryness to afford the title compound (3.32 g, 10.5 mmol, 84% yield). LCMS RT=0.98 min, ES+ve 317.

(2S,4S)-1-Tert-butyl 2-methyl 4-((1-phenyl-2,5,8,11-tetraoxatridecan-13-yl)oxy)pyrrolidine-1,2-dicarboxylate

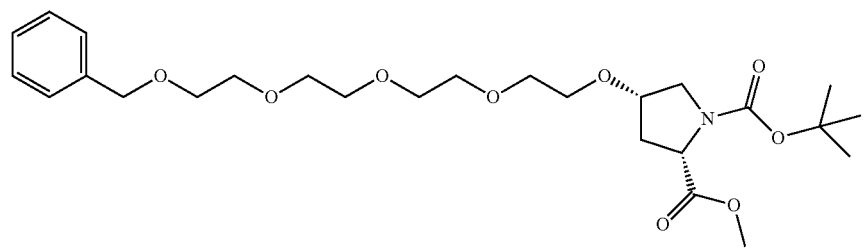 [SMILES: COC(=O)[C@@H]1C[C@H](OCCOCCOCCOCCOCc2ccccc2)CN1C(=O)OC(C)(C)C]

(2S,4S)-1-Tert-butyl 2-methyl 4-hydroxypyrrolidine-1,2-dicarboxylate (0.8 g, 3.26 mmol) was dissolved in anhydrous THF (20 mL) under nitrogen. The solution was cooled to −10° C. before sodium hydride (60% w/w in mineral oil) (0.196 g, 4.9 mmol) was added and the reaction mixture left to stir for 15 minutes. A solution of 1-phenyl-2,5,8,11-tetraoxatridecan-13-yl 4-methylbenzenesulfonate (1.29 g, 2.9 mmol) in THF (5 mL) was then added to the reaction mixture dropwise over a period of five minutes. The reaction mixture was allowed to warm to 0° C. and stirred for 4 hours, then stirred at rt for a further 48 hours. The solution was re-cooled to 0° C. and cautiously quenched using saturated aqueous ammonium chloride (50 mL). The product was then extracted using ethyl acetate (2×50 mL) and washed with brine (80 mL), dried (MgSO4), filtered and evaporated to dryness. The product was purified by chromatography on silica using a gradient elution from 0%-100% ethyl acetate in cyclohexane to afford the title compound (1.41 g, 2.8 mmol, 84% yield). LCMS RT=1.17 min, ES+ve 512.

(2S,4S)-Methyl 4-((1-phenyl-2,5,8,11-tetraoxatridecan-13-yl)oxy)pyrrolidine-2-carboxylate, Hydrochloride

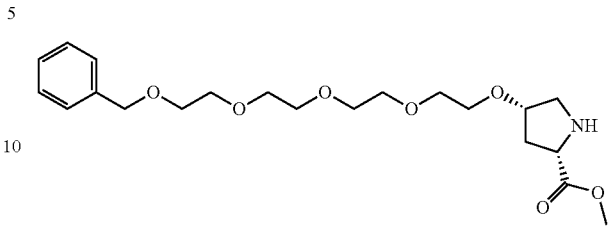

A solution of (2S,4S)-1-tert-butyl 2-methyl 4-(2-(2-(2-(benzyloxy)ethoxy)ethoxy)ethoxy)pyrrolidine-1,2-dicarboxylate (580 mg, 1.24 mmol) in methanol (1 mL) was treated with hydrochloric acid (4M in dioxane) (4 mL, 16 mmol) and the mixture was stirred at ambient temperature for 1 hour. The mixture was evaporated to dryness to afford the title compound (1.22 g, 2.7 mmol, 99% yield). LCMS RT=0.59 min, ES+ve 412.

(2S,4S)-Methyl 1-((S)-2-((S)-2-((tert-butoxycarbonyl)methyl)amino)propanamido)-3,3-dimethylbutanoyl)-4-((1-phenyl-2,5,8,11-tetraoxatridecan-13-yl)oxy)pyrrolidine-2-carboxylate

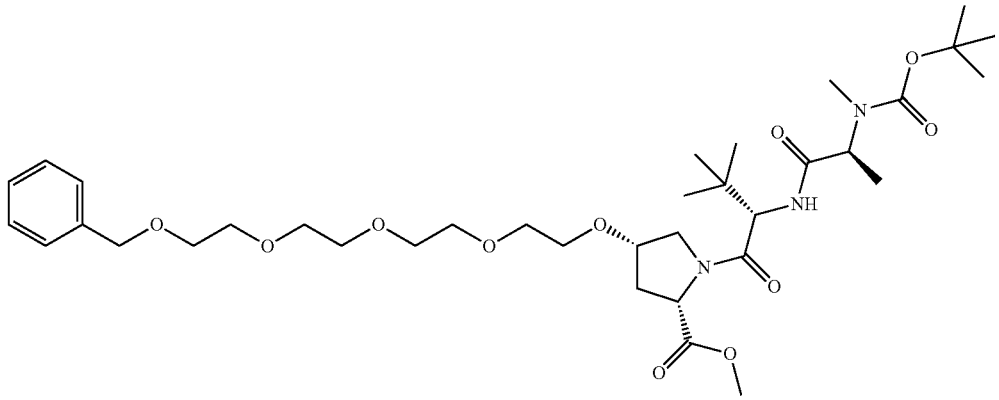 [SMILES: COC(=O)[C@@H]1C[C@H](OCCOCCOCCOCCOCc2ccccc2)CN1C(=O)[C@@H](NC(=O)[C@H](C)N(C)C(=O)OC(C)(C)C)C(C)(C)C]

A mixture of (2S,4S)-methyl 4-((1-phenyl-2,5,8,11-tetraoxatridecan-13-yl)oxy)pyrrolidine-2-carboxylate, hydrochloride (1.3 g, 2.9 mmol) and (S)-2-((S)-2-((tertbutoxycarbonyl)(methyl)amino)propanamido)-3,3-dimethylbutanoic acid (1.102 g, 3.5 mmol) in DMF (10 mL) was treated with DIPEA (2 mL, 11.6 mmol), then with HATU (1.324 g, 3.5 mmol) and then stirred at ambient temperature for 24 hours. The mixture was treated with dichloromethane (40 mL) and saturated aqueous sodium bicarbonate (20 mL) and separated. The organic phase was evaporated to dryness and the product was purified by chromatography on silica using a gradient elution from 0%-50% ethyl acetate in dichloromethane to afford the title compound (1.34 g, 1.9 mmol, 65% yield). LCMS RT=1.28 min, ES+ve 710.

(2S,4S)-1-((S)-2-((S)-2-((Tert-butoxycarbonyl)(methyl)amino)propanamido)-3,3-dimethylbutanoyl)-4-((1-phenyl-2,5,8,11-tetraoxatridecan-13-yl)oxy)pyrrolidine-2-carboxylic Acid

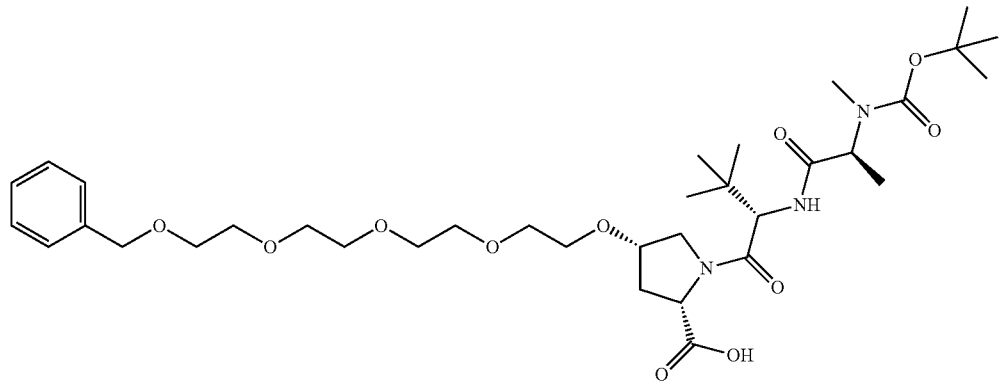 [SMILES: C[C@@H](C(=O)N[C@H](C(=O)N1C[C@@H](OCCOCCOCCOCCOCc2ccccc2)C[C@H]1C(=O)O)C(C)(C)C)N(C)C(=O)OC(C)(C)C]

A solution of (2S,4S)-methyl 1-((S)-2-((S)-2-((tert-butoxycarbonyl)(methyl)amino)propanamido)-3,3-dimethylbutanoyl)-4-((1-phenyl-2,5,8,11-tetraoxatridecan-13-yl)oxy)pyrrolidine-2-carboxylate (400 mg, 0.56 mmol) in THF (10 mL), methanol (5 mL) and water (15 mL) was treated with lithium hydroxide (27 mg, 1.13 mmol) and stirred at rt for 4 hours. The mixture was treated with ethyl acetate (50 mL) and 1M aqueous HCl (20 mL). The organic phase was washed with brine (20 mL), dried (MgSO$_4$), filtered and evaporated to dryness to afford the title compound (288 mg, 0.41 mmol, 74% yield). LCMS RT=1.18 min, ES+ve 696.

Tert-butyl ((S)-1-(((S)-3,3-dimethyl-1-oxo-1-((2S,4S)-4-((1-phenyl-2,5,8,11-tetraoxatridecan-13-yl)oxy)-2-(((R)-1,2,3,4-tetrahydronaphthalen-1-yl)carbamoyl)pyrrolidin-1-yl)butan-2-yl)amino)-1-oxopropan-2-yl)(methyl)carbamate

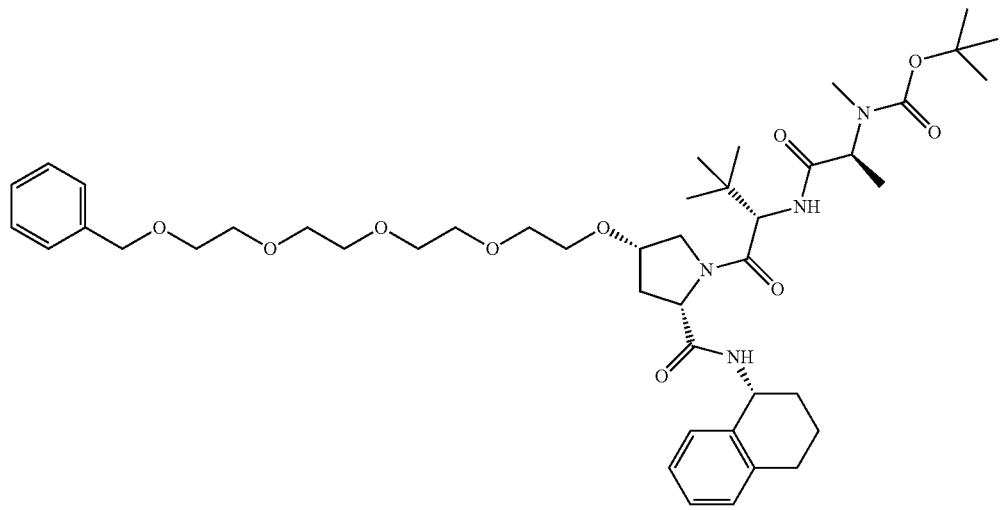 [SMILES: C[C@@H](C(=O)N[C@H](C(=O)N1C[C@@H](OCCOCCOCCOCCOCc2ccccc2)C[C@H]1C(=O)N[C@@H]1CCCc2ccccc21)C(C)(C)C)N(C)C(=O)OC(C)(C)C]

A mixture of (2S,4S)-1-((S)-2-((S)-2-((tert-butoxycarbonyl)(methyl)amino)propanamido)-3,3-dimethylbutanoyl)-4-((1-phenyl-2,5,8,11-tetraoxatridecan-13-yl)oxy)pyrrolidine-2-carboxylic acid (370 mg, 0.53 mmol) and (R)-1,2,3,4-tetrahydronaphthalen-1-amine (86 mg, 0.59 mmol) in DMF (5 mL) was treated with DIPEA (0.37 mL, 2.13 mmol), then with HATU (243 mg, 0.64 mmol) and then stirred at ambient temperature for 1 hour. The mixture was partitioned between dichloromethane (10 mL) and saturated aqueous sodium bicarbonate (10 mL). The organic phase was evaporated to dryness and the product was purified by chromatography on silica using a gradient elution from 0%-5% methanol in ethyl acetate to afford the title compound (375 mg, 0.46 mmol, 85% yield). LCMS RT=1.43 min, ES+ve 825.

Tert-butyl ((S)-1-(((S)-1-((2S,4S)-4-(2-(2-(2-(2-hydroxyethoxy)ethoxy)ethoxy)ethoxy)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate

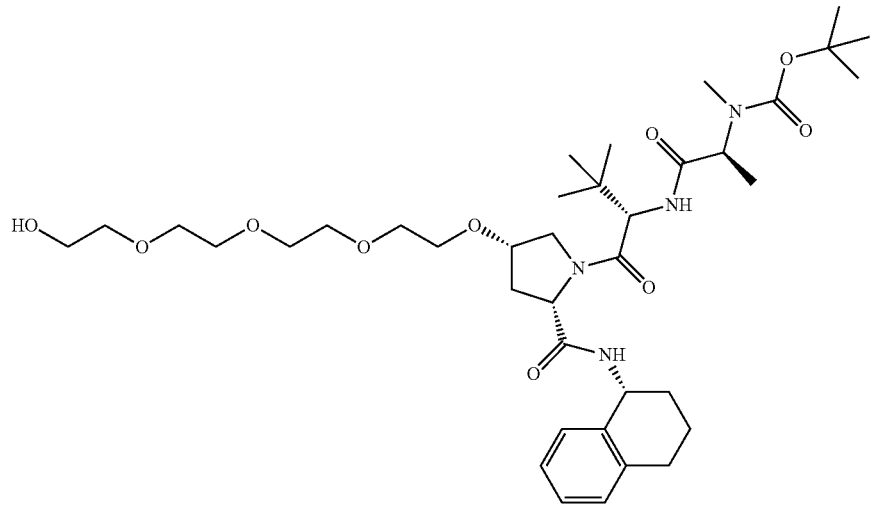 [SMILES: C[C@@H](C(=O)N[C@H](C(=O)N1C[C@@H](OCCOCCOCCOCCO)C[C@H]1C(=O)N[C@@H]1CCCc2ccccc21)C(C)(C)C)N(C)C(=O)OC(C)(C)C]

A solution of tert-butyl ((S)-1-(((S)-3,3-dimethyl-1-oxo-1-((2S,4S)-4-((1-phenyl-2,5,8,11-tetraoxatridecan-13-yl)oxy)-2-(((R)-1,2,3,4-tetrahydronaphthalen-1-yl)carbamoyl)pyrrolidin-1-yl)butan-2-yl)amino)-1-oxopropan-2-yl)(methyl)carbamate (410 mg, 0.50 mmol) in ethanol (10 mL) was added in an inert atmosphere to 10% palladium on carbon (degussa type, 100 mg) and then stirred in an atmosphere of hydrogen for 2 hours. The mixture was filtered through celite and evaporated to dryness to afford the title compound (314 mg, 0.43 mmol, 86% yield). LCMS RT=1.17 min, ES+ve 735.

2-(2-(2-(2-(((3S,5S)-1-((S)-2-((S)-2-((Tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)oxy)ethoxy)ethoxy)ethoxy)ethyl methanesulfonate

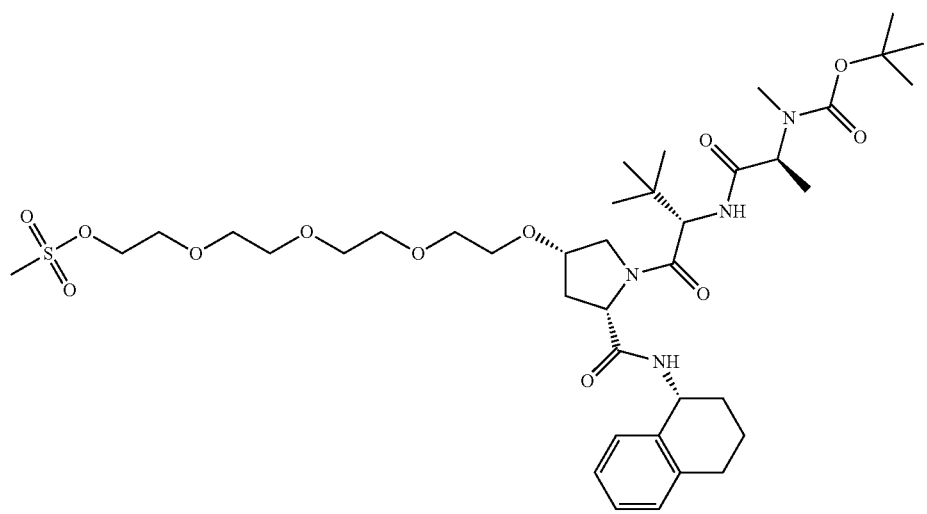 [SMILES: C[C@@H](C(=O)N[C@H](C(=O)N1C[C@@H](OCCOCCOCCOCCOS(C)(=O)=O)C[C@H]1C(=O)N[C@@H]1CCCc2ccccc21)C(C)(C)C)N(C)C(=O)OC(C)(C)C]

An ice-cooled solution of tert-butyl ((S)-1-(((S)-1-((2S, 4S)-4-(2-(2-(2-(2-hydroxyethoxy)ethoxy)ethoxy)ethoxy)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (300 mg, 0.41 mmol) in dichloromethane (10 mL) was treated with DIPEA (0.107 mL, 0.61 mmol) and then with methanesulfonyl chloride (0.038 mL, 0.49 mmol) and the mixture was stirred for 30 minutes at 0° C. and at rt for a further 30 minutes. The mixture was then treated with dichloromethane (10 mL) and saturated aqueous sodium bicarbonate (20 mL) and separated. The organic fraction was evaporated to dryness to afford the title compound (315 mg, 0.39 mmol, 95% yield). LCMS RT=1.25 min, ES+ve 813.

Tert-butyl ((S)-1-(((S)-1-((2S,4S)-4-(2-(2-(2-(2-((6-(tert-butylsulfonyl)-4-((5-fluoro-1H-indazol-3-yl)amino)quinolin-7-yl)oxy)ethoxy)ethoxy)ethoxy)ethoxy)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate

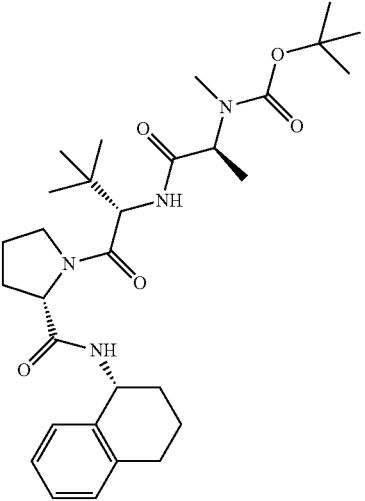

A mixture of 6-(tert-butylsulfonyl)-4-((5-fluoro-1H-indazol-3-yl)amino)quinolin-7-ol (61.3 mg, 0.148 mmol), potassium carbonate (51 mg, 0.37 mmol) and sodium iodide (18.4 mg, 0.12 mmol) was treated with a solution of 2-(2-(2-(2-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)ethoxy)ethoxy)ethoxy)ethyl methanesulfonate (100 mg, 0.12 mmol) in DMF (2 mL) and the mixture was heated at 80° C. for 4 hours. The cooled mixture was filtered and subjected directly to purification by mass-directed automated preparative HPLC (formic acid modifier) to afford the title compound (46 mg, 0.04 mmol, 33% yield). LCMS RT=1.04 min, ES+ve 516 ([M+2H]$^{2+}$).

Tert-butyl 14-((6-(tert-butylsulfonyl)-4-((3,4-dimethyl-1H-pyrazol-5-yl)amino)quinazolin-7-yl)oxy)-3,6,9,12-tetraoxatetradecan-1-oate

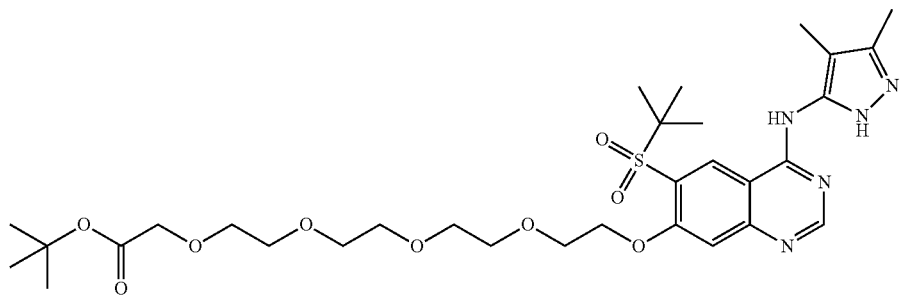 [SMILES: Cc1n[nH]c(Nc2ncnc3cc(OCCOCCOCCOCCOCC(=O)OC(C)(C)C)c(S(=O)(=O)C(C)(C)C)cc23)c1C]

To a solution of 6-(tert-butylsulfonyl)-4-((4,5-dimethyl-1H-pyrazol-3-yl)amino)quinazolin-7-ol (140 mg, 0.37 mmol, obtained as described in WO 2014/128622) in DMF (2 mL) was added tert-butyl 14-(tosyloxy)-3,6,9,12-tetraoxatetradecan-1-oate (259 mg, 0.56 mmol, prepared as described in Nature Chemical Biology, 2015, 11, p 611), potassium carbonate (155 mg, 1.1 mmol) and sodium iodide (56 mg, 0.37 mmol) and reaction stirred at 80° C. for 2 hours. The product was subjected directly to purification by mass-directed automated preparative HPLC (formic acid modifier) to afford the title compound (35 mg, 0.046 mmol, 12% yield). LCMS RT=0.83 min, ES+ve 666.

2-((6-(Tert-butylsulfonyl)-4-((3,4-dimethyl-1H-pyrazol-5-yl)amino)quinazolin-7-yl)oxy)ethanol

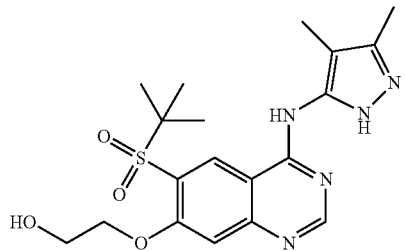 [SMILES: Cc1n[nH]c(Nc2ncnc3cc(OCCO)c(S(=O)(=O)C(C)(C)C)cc23)c1C]

To a solution of 6-(tert-butylsulfonyl)-N-(4,5-dimethyl-1H-pyrazol-3-yl)-7-fluoroquinazolin-4-amine (250 mg, 0.66 mmol, obtained as described in WO 2014/128622) in ethylene glycol (923 µl, 16.6 mmol) was added sodium hydride (79 mg, 3.3 mmol) and the reaction mixture was sealed stirred at 100° C. for 105 minutes in a Biotage microwave. The mixture was cooled to room temperature and subjected directly to purification by flash chromatography (60 g pre-packed C-18 SNAP cartridge: 5% to 30% acetonitrile (0.1% formic acid) in water (0.1% formic acid)). Desired fractions were combined and concentrated to afford the title compound (200 mg, 0.48 mmol, 72% yield). LCMS RT=0.54 min, ES+ve 420.

6-(Tert-butylsulfonyl)-7-(2-((2-chloropyrimidin-5-yl)oxy)ethoxy)-N-(3,4-dimethyl-1H-pyrazol-5-yl)quinazolin-4-amine

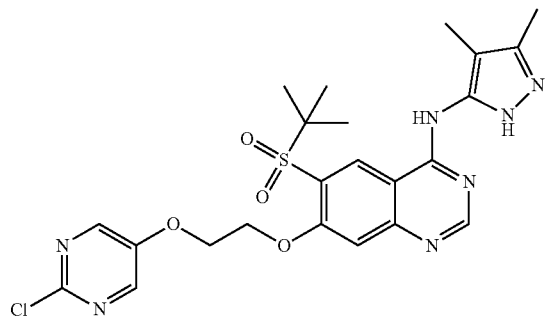 [SMILES: Cc1n[nH]c(Nc2ncnc3cc(OCCOc4cnc(Cl)nc4)c(S(=O)(=O)C(C)(C)C)cc23)c1C]

To a solution of 2-((6-(tert-butylsulfonyl)-4-((4,5-dimethyl-1H-pyrazol-3-yl)amino)quinazolin-7-yl)oxy)ethanol (247 mg, 0.59 mmol) in THF (5 mL) was added 2-chloropyrimidin-5-ol (85 mg, 0.65 mmol), triphenylphosphine (232 mg, 0.88 mmol) and DIAD (0.172 mL, 0.88 mmol) and the reaction mixture was stirred at rt under an atmosphere of nitrogen for 42 hours. The reaction mixture was concentrated, and the residue subjected directly to purification by flash chromatography (60 g pre-packed C-18 SNAP cartridge: 5% to 30% acetonitrile (0.1% formic acid) in water (0.1% formic acid)). Desired fractions were combined and concentrated to afford the title compound (167 mg, 0.31 mmol, 53% yield). LCMS RT=0.73 min, ES+ve 532.

6-(Tert-butylsulfonyl)-N-(3,4-dimethyl-1H-pyrazol-5-yl)-7-(piperidin-4-yloxy)quinazolin-4-amine

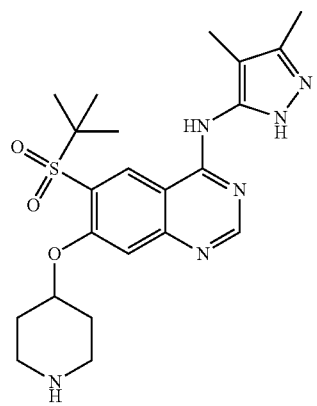 [SMILES: Cc1n[nH]c(Nc2ncnc3cc(OC4CCNCC4)c(S(=O)(=O)C(C)(C)C)cc23)c1C]

Under nitrogen, a mixture of 6-(tert-butylsulfonyl)-N-(4,5-dimethyl-1H-pyrazol-3-yl)-7-fluoroquinazolin-4-amine (300 mg, 0.795 mmol, obtained as described in WO 2014/128622) and piperidin-4-ol (402 mg, 4.0 mmol) in dioxane (5 mL) and NMP (1.5 mL) was treated with sodium hydride (60% in mineral oil, 57 mg, 2.4 mmol) and stirred for 10 minutes. The mixture was then heated at 80° C. for 4 hours and cooled, treated with acetic acid (0.5 mL) and concentrated to about 1.5 mL. The product was subjected to purification by mass-directed automated preparative HPLC (ammonium bicarbonate modifier) to afford the title compound (270 mg, 0.59 mmol, 74% yield). LCMS RT=0.46 min, ES+ve 459.

6-(Tert-butylsulfonyl)-N-(3,4-dimethyl-M-pyrazol-5-yl)-7-(piperidin-4-ylmethoxy)quinazolin-4-amine

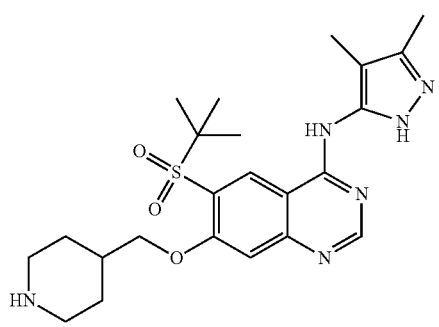 [SMILES: Cc1n[nH]c(Nc2ncnc3cc(OCC4CCNCC4)c(S(=O)(=O)C(C)(C)C)cc23)c1C]

Under nitrogen, a mixture of 6-(tert-butylsulfonyl)-N-(4,5-dimethyl-1H-pyrazol-3-yl)-7-fluoroquinazolin-4-amine (300 mg, 0.795 mmol, obtained as described in WO 2014/128622) and piperidin-4-ylmethanol (275 mg, 2.39 mmol)

in 1,4-dioxane (5 mL) and NMP (1.5 mL) was treated with sodium hydride (191 mg, 4.8 mmol) and stirred for 10 minutes. The mixture was then heated at 80° C. for 4 hours and cooled. The mixture was treated with acetic acid (0.5 mL) and evaporated down to about 1.5 mL. The product was subjected to purification by mass-directed automated preparative HPLC (ammonium bicarbonate modifier) to afford the title compound (298 mg, 0.63 mmol, 79% yield). LCMS RT=0.44 min, ES+ve 473.

Tert-butyl 4-(2-((6-(tert-butylsulfonyl)-4-((3,4-dimethyl-1H-pyrazol-5-yl)amino)quinazolin-7-yl)oxy)ethyl)piperazine-1-carboxylate

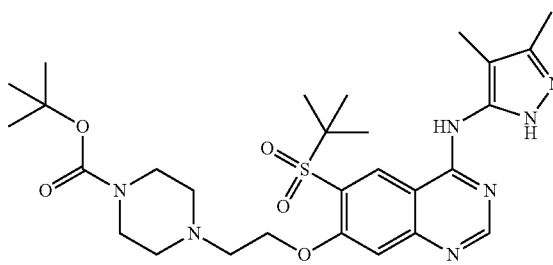

An ice-cooled suspension of sodium hydride (60% w/w in mineral oil, 1.59 g, 40 mmol) in 1,4-dioxane (15 mL) was treated dropwise with a solution of tert-butyl 4-(2-hydroxyethyl)piperazine-1-carboxylate (9.15 g, 40 mmol) in 1,4-dioxane (20 mL). The mixture was stirred for 20 mins and then treated with 6-(tert-butylsulfonyl)-N-(4,5-dimethyl-1H-pyrazol-3-yl)-7-fluoroquinazolin-4-amine (3 g, 8.0 mmol). The reaction mixture was stirred for 30 mins and then heated to 100° C. and stirred vigorously for a further hour. The mixture was then cooled and acidified to pH 7 with aqueous HCl (2M) and then partitioned between water and ethyl acetate. The aqueous layer was extracted with ethyl acetate (2×40 mL). The combined organic layer was washed with water (40 mL), brine (40 mL) and then dried over magnesium sulfate, filtered, concentrated in vacuo, and the residue subjected directly to purification by flash chromatography (100 g pre-packed silica cartridge: 0-50% methanol in tert-butyl methyl ether). Desired fractions were combined and concentrated to afford the title compound (1.31 g, 2.2 mmol, 27% yield). LCMS Method B RT=1.04 min, ES+ve 588.

6-(Tert-butylsulfonyl)-N-(3,4-dimethyl-1H-pyrazol-5-yl)-7-(2-(piperazin-1-yl)ethoxy)quinazolin-4-amine

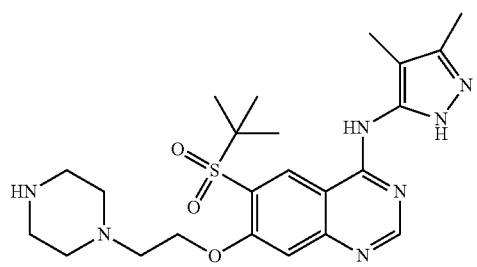 [SMILES: Cc1n[nH]c(Nc2ncnc3cc(OCCN4CCNCC4)c(S(=O)(=O)C(C)(C)C)cc23)c1C]

To a solution of tert-butyl 4-(2-((6-(tert-butylsulfonyl)-4-((4,5-dimethyl-1H-pyrazol-3-yl)amino)quinazolin-7-yl)oxy)ethyl)piperazine-1-carboxylate (1.3 g, 2.2 mmol) in THF (5 mL) and methanol (10 mL) under nitrogen was added HCl (4M in dioxan) (5 mL, 20 mmol). The mixture was stirred at room temperature for 6 hours then filtered under vacuum to afford the title compound (1.25 g, 2.10 mmol, 95% yield). LCMS Method B RT=0.74 min, ES+ve 488.

Methyl 6-(4-(2-((6-(tert-butylsulfonyl)-4-((3,4-dimethyl-1H-pyrazol-5-yl)amino)quinazolin-7-yl)oxy)ethyl)piperazin-1-yl)nicotinate

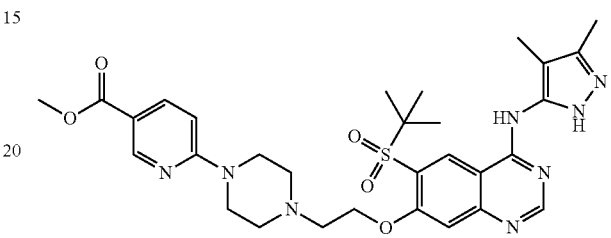

To a solution of 6-(tert-butylsulfonyl)-N-(4,5-dimethyl-1H-pyrazol-3-yl)-7-(2-(piperazin-1-yl)ethoxy)quinazolin-4-amine, 3Hydrochloride (400 mg, 0.67 mmol) in NMP (2 mL) was added DIPEA (0.585 mL, 3.4 mmol) and methyl 6-chloronicotinate (138 mg, 0.80 mmol), then sealed and heated at 120° C. by in a Biotage microwave for 3 hours. The product was directly purified by flash chromatography (60 g pre-packed C-18 SNAP cartridge: 30-85% acetonitrile (0.1% ammonia) in water (10 mM ammonium formate)). Desired fractions were combined and concentrated to afford the title compound (261 mg, 0.42 mmol, 63% yield). LCMS Method B RT=1.00 min, ES+ve 623.

6-(4-(2-((6-(Tert-butylsulfonyl)-4-((3,4-dimethyl-1H-pyrazol-5-yl)amino)quinazolin-7-yl)oxy)ethyl)piperazin-1-yl)nicotinic Acid

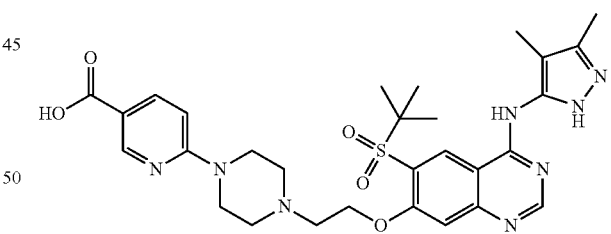

To a solution of methyl 6-(4-(2-((6-(tert-butylsulfonyl)-4-((4,5-dimethyl-1H-pyrazol-3-yl)amino)quinazolin-7-yl)oxy)ethyl)piperazin-1-yl)nicotinate (261 mg, 0.42 mmol) in methanol (2 mL) was added lithium hydroxide (1M solution in water, 2.24 mL) and the reaction mixture was stirred at 40° C. for 25 hours. The mixture was neutralised with HCl (4M in dioxane, 1 mL, 4 mmol) and evaporated to dryness to afford the title compound, which was used without further purification (291 mg, 0.41 mmol, 97% yield). LCMS RT=0.52 min, ES+ve 609.

The following compounds were prepared by a method sequence analogous to that for 6-(4-(2-((6-(tert-butylsulfonyl)-4-((3,4-dimethyl-1H-pyrazol-5-yl)amino)quinazolin-7-yl)oxy)ethyl)piperazin-1-yl)nicotinic acid:

| Compound Name/Structure | Yield | LCMS RT | ES + ve |
|---|---|---|---|
| Tert-butyl 4-(2-((6-(tert-butylsulfonyl)-4-((3,4-dimethyl-1H-pyrazol-5-yl)amino)quinazolin-7-yl)oxy)ethyl)piperidine-1-carboxylate | 52% | Method B 1.17 mins | 587 |
| 6-(Tert-butylsulfonyl)-N-(3,4-dimethyl-1H-pyrazol-5-yl)-7-(2-(piperidin-4-yl)ethoxy)quinazolin-4-amine | 85% | Method B 0.95 mins | 487 |
| Methyl 6-(4-(2-((6-(tert-butylsulfonyl)-4-((3,4-dimethyl-1H-pyrazol-5-yl)amino)quinazolin-7-yl)oxy)ethyl)piperidin-1-yl)nicotinate | 35% | Method B 1.14 mins | 622 |
| 6-(4-(2-((6-(Tert-butylsulfonyl)-4-((3,4-dimethyl-1H-pyrazol-5-yl)amino)quinazolin-7-yl)oxy)ethyl)piperidin-1-yl)nicotinic acid | 99% | Method A 0.66 mins | 608 |
| Tert-butyl 4-(3-((6-(tert-butylsulfonyl)-4-((3,4-dimethyl-1H-pyrazol-5-yl)amino)quinazolin-7-yl)oxy)propyl)piperazine-1-carboxylate | 17% | Method B 1.06 mins | 602 |

| Compound Name/Structure | Yield | LCMS RT | ES + ve |
|---|---|---|---|
| 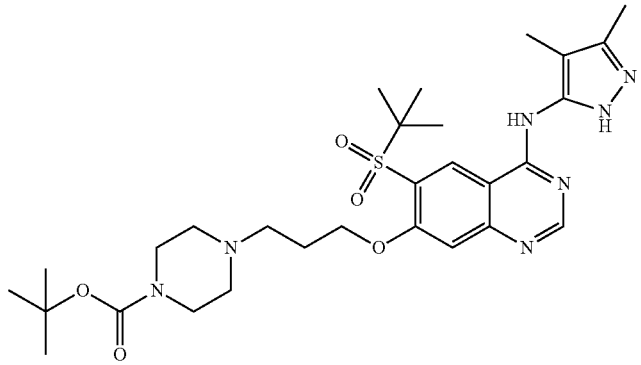 [SMILES: Cc1n[nH]c(Nc2ncnc3cc(OCCCN4CCN(C(=O)OC(C)(C)C)CC4)c(S(=O)(=O)C(C)(C)C)cc23)c1C] 6-(Tert-butylsulfonyl)-N-(3,4-dimethyl-1H-pyrazol-5-yl)-7-(3 (piperazin-1-yl)propoxy)quinazolin-4-amine | 98% | Method B 0.84 mins | 502 |
| 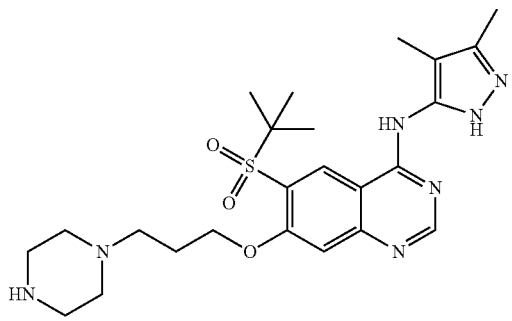 [SMILES: Cc1n[nH]c(Nc2ncnc3cc(OCCCN4CCNCC4)c(S(=O)(=O)C(C)(C)C)cc23)c1C] Methyl 6-(4-(3-((6-(tert-butylsulfonyl)-4-((3,4-dimethyl-1H-pyrazol-5-yl)amino)quinazolin-7-yl)oxy)propyl)piperazin-1-yl)nicotinate | 49.9% | Method B 1.02 mins | 637 |
| 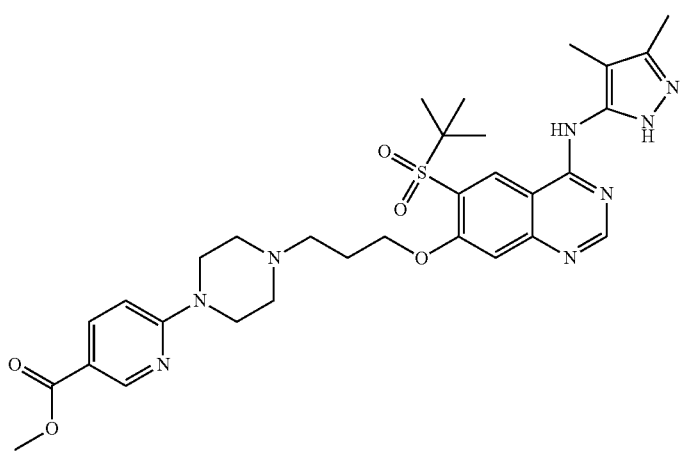 [SMILES: COC(=O)c1ccc(N2CCN(CCCOc3cc4ncnc(Nc5[nH]nc(C)c5C)c4cc3S(=O)(=O)C(C)(C)C)CC2)nc1] 6-(4-(3-((6-(Tert-butylsulfonyl)-4-((3,4-dimethyl-1H-pyrazol-5-yl)amino)quinazolin-7-yl)oxy)propyl)piperazin-1-yl)nicotinic acid | 99% | Method A 0.49 mins | 623 |

| Compound Name/Structure | Yield | LCMS RT | ES + ve |
|---|---|---|---|
| 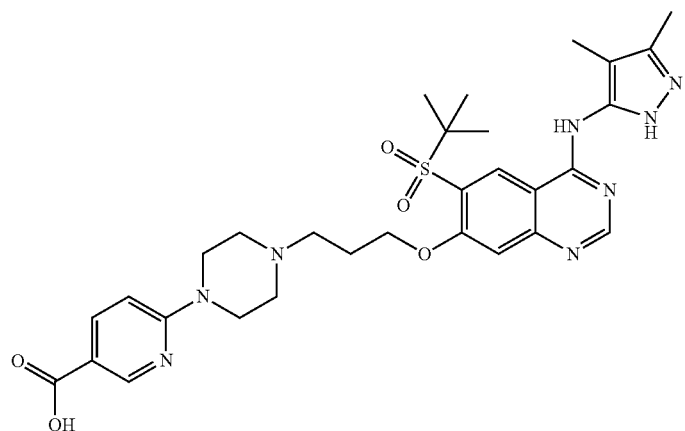 | | | |
| Tert-butyl 4-(3-((6-(tert-butylsulfonyl)-4-((3,4-dimethyl-1H-pyrazol-5-yl)amino)quinazolin-7-yl)oxy)propyl)piperidine-1-carboxylate | 58% | Method A 1.03 mins | 601 |
| 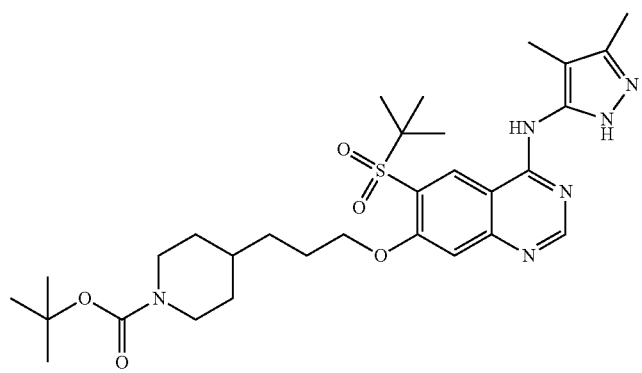 [SMILES: Cc1n[nH]c(Nc2ncnc3cc(OCCCC4CCN(C(=O)OC(C)(C)C)CC4)c(S(=O)(=O)C(C)(C)C)cc23)c1C] | | | |
| 6-(Tert-butylsulfonyl)-N-(3,4-dimethyl-1H-pyrazol-5-yl)-7-(3-(piperidin-4-yl)propoxy)quinazolin-4-amine | 99% | Method A 0.47 mins | 501 |
| 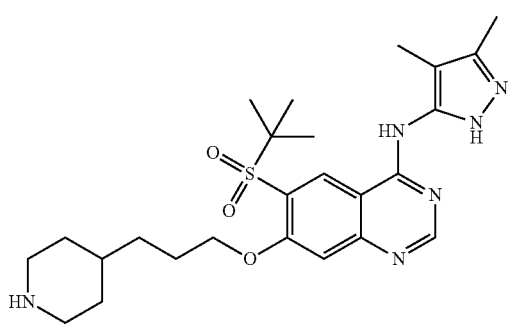 | | | |
| Methyl 6-(4-(3-((6-(tert-butylsulfonyl)-4-((3,4-dimethyl-1H-pyrazol-5-yl)amino)quinazolin-7-yl)oxy)propyl)piperidin-1-yl)nicotinate | 66% | Method B 1.19 mins | 636 |

| Compound Name/Structure | Yield | LCMS RT | ES + ve |
|---|---|---|---|
| 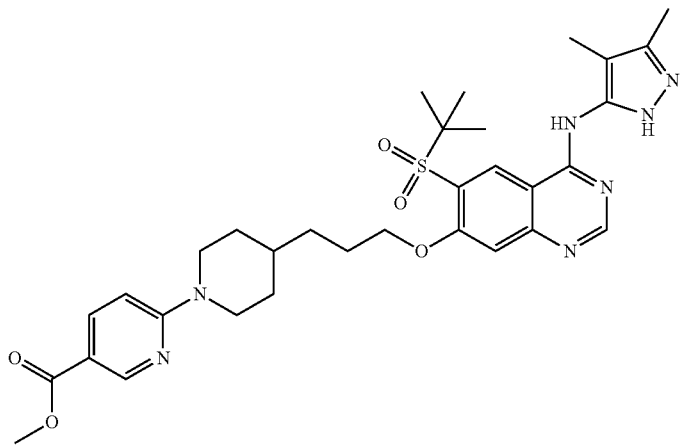 [SMILES: COC(=O)c1ccc(N2CCC(CCCOc3cc4ncnc(Nc5[nH]nc(C)c5C)c4cc3S(=O)(=O)C(C)(C)C)CC2)nc1]  6-(4-(3-((6-(Tert-butylsulfonyl)-4-((3,4-dimethyl-1H-pyrazol-5-yl)amino)quinazolin-7-yl)oxy)propyl)piperidin-1-yl)nicotinic acid | 96% | Method A 0.70 mins | 622 |
| 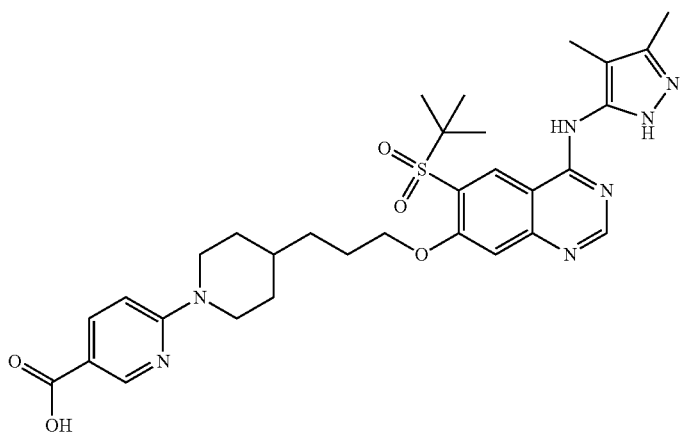  Methyl 2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidine-5-carboxylate | 71% | Method A 0.60 mins | 624 |
| 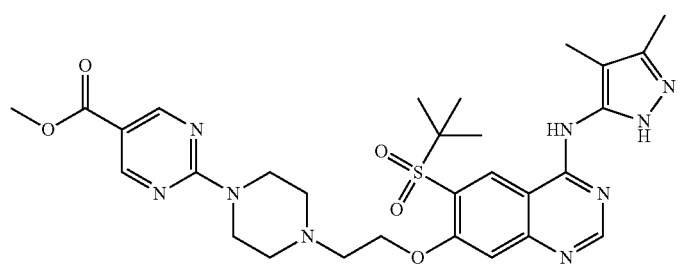 [SMILES: COC(=O)c1cnc(N2CCN(CCOc3cc4ncnc(Nc5[nH]nc(C)c5C)c4cc3S(=O)(=O)C(C)(C)C)CC2)nc1]  2-(4-(2-((6-(Tert-butylsulfonyl)-4-((4,5-dimethyl-1H-pyrazol-3-yl)amino)quinazolin-7-yl)oxy)ethyl)piperazin-1-yl)pyrimidine-5-carboxylic acid, 3 Hydrochloride | 98% | Method A 0.52 mins | 610.2 |

| Compound Name/Structure | Yield | LCMS RT | ES + ve |
|---|---|---|---|
| 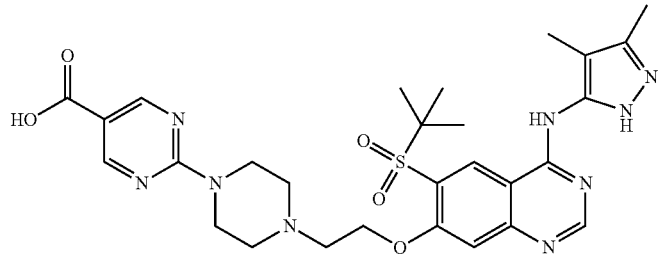<br>Methyl 2-(4-(3-((6-(tert-butylsulfonyl)-4-((4,5-dimethyl-1H-pyrazol-3-yl)amino)quinazolin-7-yl)oxy)propyl)piperidin-1-yl)pyrimidine-5-carboxylate | 43% | Method A<br>0.97 mins | 637 |
| 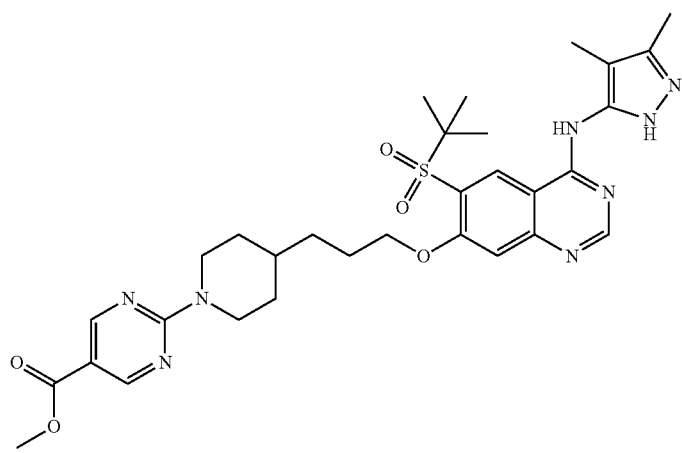 [SMILES: COC(=O)c1cnc(N2CCC(CCCOc3cc4ncnc(Nc5[nH]nc(C)c5C)c4cc3S(=O)(=O)C(C)(C)C)CC2)nc1]<br>2-(4-(3-((6-(Tert-butylsulfonyl)-4-((4,5-dimethyl-1H-pyrazol-3-yl)amino)quinazolin-7-yl)oxy)propyl)piperidin-1-yl)pyrimidine-5-carboxylic acid | 100% | Method A<br>0.85 mins | 623 |
| 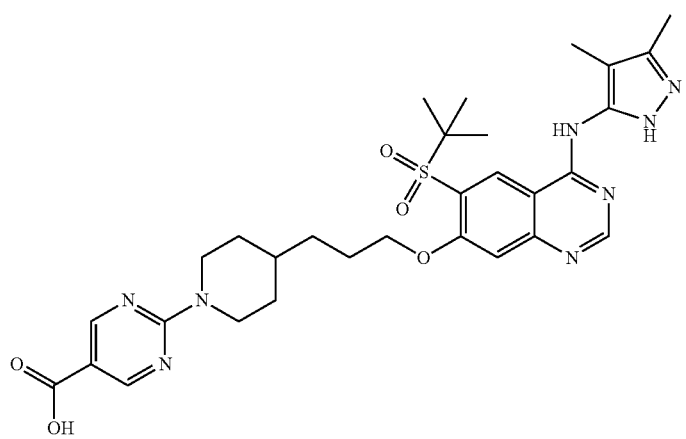 [SMILES: Cc1n[nH]c(Nc2ncnc3cc(OCCCC4CCN(c5ncc(C(=O)O)cn5)CC4)c(S(=O)(=O)C(C)(C)C)cc23)c1C]<br>Methyl 5-(4-(2-((6-(tert-butylsulfonyl)-4-((4,5-dimethyl-1H-pyrazol-3-yl)amino)quinazolin-7-yl)oxy)ethyl)piperazin-1-yl)pyrazine-2-carboxylate | 58% | Method B<br>0.92 mins | 624 |

| Compound Name/Structure | Yield | LCMS RT | ES + ve |
|---|---|---|---|
| 5-(4-(2-((6-(Tert-butylsulfonyl)-4-((4,5-dimethyl-1H-pyrazol-3-yl)amino)quinazolin-7-yl)oxy)ethyl)piperazin-1-yl)pyrazine-2-carboxylic acid | 44% | Method B 0.67 mins | 610 |

Tert-butyl 4-((2-chloropyrimidin-5-yl)oxy)piperidine-1-carboxylate

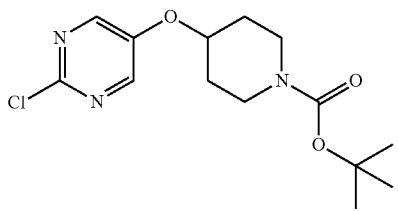 [SMILES: CC(C)(C)OC(=O)N1CCC(Oc2cnc(Cl)nc2)CC1]

To a solution of tert-butyl 4-hydroxypiperidine-1-carboxylate (561 mg, 2.8 mmol) in THF (5 mL) was added 2-chloropyrimidin-5-ol (200 mg, 1.53 mmol), triphenylphosphine (548 mg, 2.09 mmol) and DIAD (0.406 mL, 2.09 mmol) and the reaction mixture was stirred at 20° C. under nitrogen for 72 h. The reaction mixture was concentrated in vacuo, and the residue was subjected directly to purification by flash chromatography (60 g pre-packed C-18 SNAP cartridge using a gradien elution from 35-90% acetonitrile (0.1% formic acid) in water (0.1% formic acid)). Desired fractions were combined and concentrated to afford the title compound (430 mg, 1.1 mmol, 77% yield). LCMS RT=1.12 min, ES+ve 258 (M+H-tBu).

Tert-butyl 4-((2-(4-(((6-(tert-butylsulfonyl)-4-((3,4-dimethyl-1H-pyrazol-5-yl)amino)quinazolin-7-yl)oxy)methyl)piperidin-1-yl)pyrimidin-5-yl)oxy)piperidine-1-carboxylate

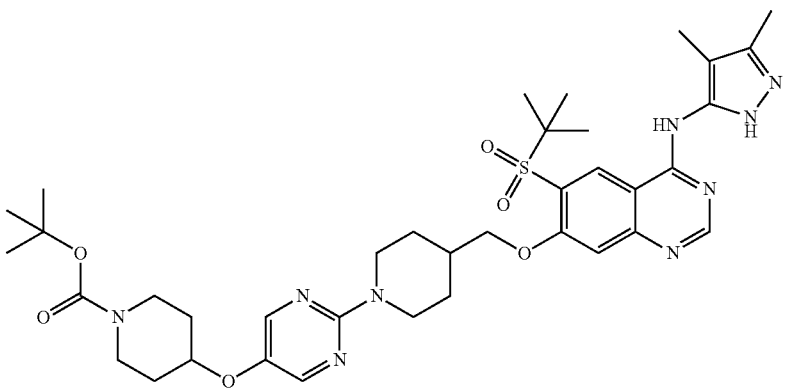 [SMILES: Cc1n[nH]c(Nc2ncnc3cc(OCC4CCN(c5ncc(OC6CCN(C(=O)OC(C)(C)C)CC6)cn5)CC4)c(S(=O)(=O)C(C)(C)C)cc23)c1C]

To a solution of tert-butyl 4-((2-chloropyrimidin-5-yl)oxy)piperidine-1-carboxylate (259 mg, 0.83 mmol) in NMP (2 mL) was added DIPEA (0.6 mL, 3.4 mmol) and 6-(tert-butylsulfonyl)-N-(4,5-dimethyl-1H-pyrazol-3-yl)-7-(piperidin-4-ylmethoxy)quinazolin-4-amine, 3Hydrochloride (400 mg, 0.69 mmol) and the reaction mixture was stirred at 140° C. under an atmosphere of nitrogen for 42 h. The residue was subjected directly to purification by flash chromatography (60 g pre-packed C-18 SNAP cartridge using a gradient elution from 50-95% acetonitrile (0.1% ammonia) in water (10 mM ammonium bicarbonate)). Desired fractions were combined and concentrated to afford the title compound (240 mg, 0.32 mmol, 47% yield). LCMS RT=1.09 min, ES+ve 750.

6-(Tert-butylsulfonyl)-N-(3,4-dimethyl-1H-pyrazol-5-yl)-7-((1-(5-(piperidin-4-yloxy)pyrimidin-2-yl)piperidin-4-yl)methoxy)quinazolin-4-amine

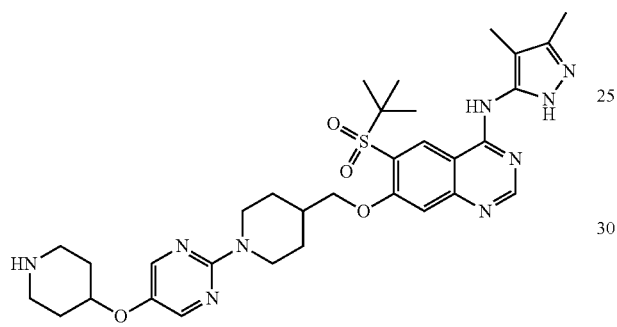

To tert-butyl 4-((2-(4-(((6-(tert-butylsulfonyl)-4-((4,5-dimethyl-1H-pyrazol-3-yl)amino)quinazolin-7-yl)oxy)methyl)piperidin-1-yl)pyrimidin-5-yl)oxy)piperidine-1-carboxylate (240 mg, 0.32 mmol) in DCM (2.0 mL) was added TFA (1.23 mL, 16 mmol) and the reaction mixture was stirred at rt under nitrogen for 30 minutes. The mixture was evaporated to dryness to afford the title compound (350 mg, 0.32 mmol, 99% yield). LCMS RT=0.57 min, ES+ve 650.

Tert-butyl ((S)-1-(((S)-1-((S)-7-(2-(2-(2-((4-(benzo[d]thiazol-5-ylamino)-6-(tert-butylsulfonyl)quinolin-7-yl)oxy)ethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate

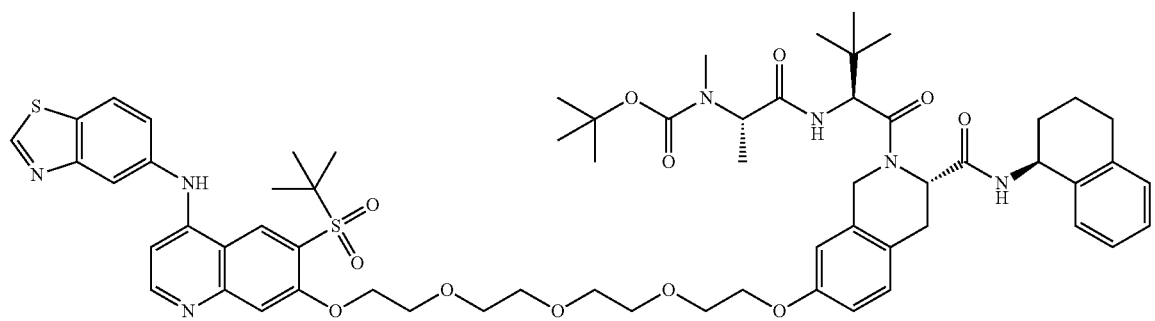 [SMILES: C[C@@H](C(=O)N[C@H](C(=O)N1Cc2cc(OCCOCCOCCOCCOc3cc4nccc(Nc5ccc6scnc6c5)c4cc3S(=O)(=O)C(C)(C)C)ccc2C[C@H]1C(=O)N[C@H]1CCCc2ccccc21)C(C)(C)C)N(C)C(=O)OC(C)(C)C]

A mixture of 4-(benzo[d]thiazol-5-ylamino)-6-(tert-butyl-sulfonyl)quinolin-7-ol (61 mg, 0.15 mmol), tert-butyl ((S)-1-(((S)-1-((S)-7-(2-(2-(2-(2-chloroethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (80 mg, 0.098 mmol) and potassium carbonate (41 mg, 0.29 mmol) in DMF (1.5 mL) was heated at 105° C. for 8 hours. The crude product was subjected directly to purification by mass-directed automated preparative HPLC (formic acid modifier) to afford the title compound (78 mg, 0.065 mmol, 67% yield). LCMS RT=1.11 min, ES+ve 1193.

Tert-butyl ((S)-1-(((S)-1-((S)-7-(2-(2-(2-(2-((6-(tert-butylsulfonyl)-4-((4,5-dimethyl-1H-pyrazol-3-yl)amino)quinazolin-7-yl)oxy)ethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate

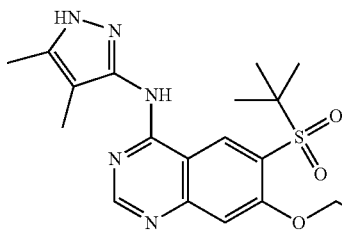
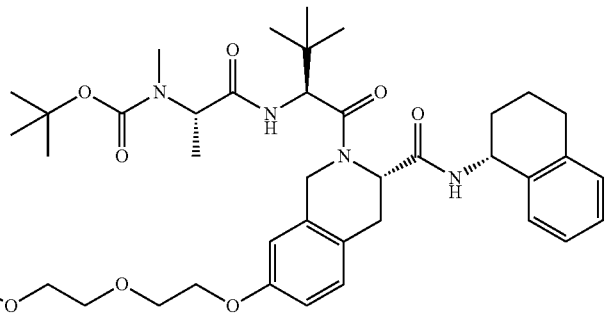

A mixture of tert-butyl ((S)-1-(((S)-1-((S)-7-(2-(2-(2-(2-chloroethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (800 mg, 0.98 mmol), 6-(tert-butylsulfonyl)-4-((4,5-dimethyl-1H-pyrazol-3-yl)amino)quinazolin-7-ol (442 mg, 1.18 mmol), potassium carbonate (41 mg, 0.29 mmol) and sodium iodide (147 mg, 0.98 mmol) in DMF (1.5 mL) was heated at 105° C. for 8 hours. The cooled product mixture was filtered and subjected directly to purification by mass-directed automated preparative HPLC (formic acid modifier) to afford the title compound (355 mg, 0.31 mmol, 31% yield) LCMS RT=1.21 min, ES+ve 1154.

Tert-butyl ((S)-1-(((S)-1-((S)-7-((6-chloropyrimidin-4-yl)oxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate

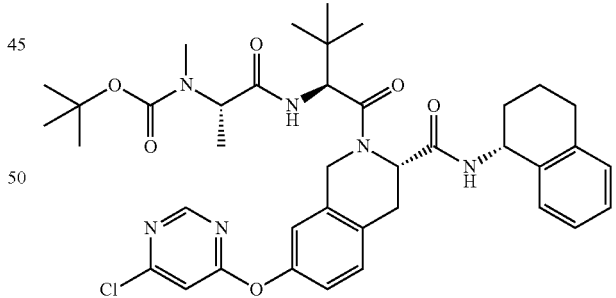

A solution of tert-butyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (300 mg, 0.48 mmol) in DMF (7 mL) was treated with 4,6-dichloropyrimidine (76 mg, 0.51 mmol) and potassium carbonate (147 mg, 1.06 mmol) and then stirred at rt overnight. The mixture was treated with dichloromethane (30 mL) and water (10 mL). The organic phase was evaporated to dryness and the product was purified by chromatography on silica using a gradient elution from 0% to 100% ethyl acetate in cyclohexane to afford the title compound (302 mg, 0.41 mmol, 85% yield). LCMS RT=1.46 min, ES+ve 733.

Tert-butyl ((S)-1-(((S)-1-((S)-7-((6-(4-(((6-(tert-butylsulfonyl)-4-((4,5-dimethyl-1H-pyrazol-3-yl)amino)quinazolin-7-yl)oxy)piperidin-1-yl)pyrimidin-4-yl)oxy)-3-(((R)-1,2,3,4-tetrahydronaphthalen-1-yl))carbamoyl)-3,4-dihydroisoquinolin-2(1H)-yl)-3,3-dimethyl-1-oxobutan-2-yl)amino)-1-oxopropan-2-yl)(methyl)carbamate

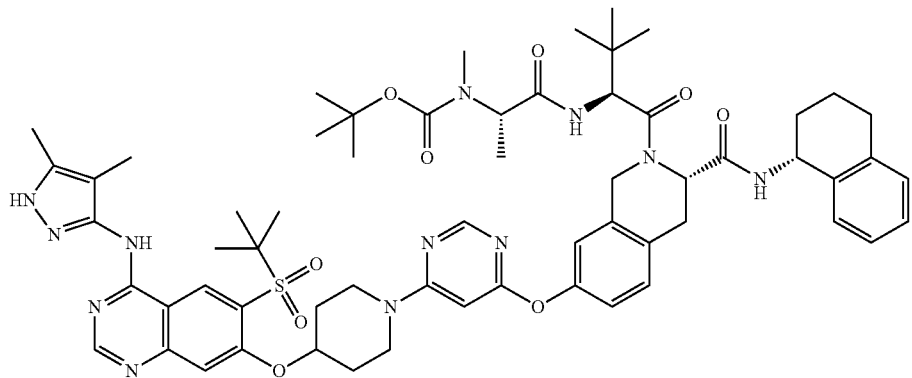 [SMILES: Cc1[nH]nc(Nc2ncnc3cc(OC4CCN(c5cc(Oc6ccc7c(c6)CN(C(=O)[C@@H](NC(=O)[C@H](C)N(C)C(=O)OC(C)(C)C)C(C)(C)C)[C@H](C(=O)N[C@@H]6CCCc8ccccc86)C7)ncn5)CC4)c(S(=O)(=O)C(C)(C)C)cc23)c1C]

A mixture of 6-(tert-butylsulfonyl)-N-(4,5-dimethyl-1H-pyrazol-3-yl)-7-(piperidin-4-yloxy)quinazolin-4-amine (69 mg, 0.15 mmol) and tert-butyl ((S)-1-(((S)-1-((S)-7-((6-chloropyrimidin-4-yl)oxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (100 mg, 0.14 mmol) in DMF (2 mL) was treated with sodium bicarbonate (46 mg, 0.55 mmol) and stirred overnight at 100° C. The product was subjected directly to purification by mass-directed automated preparative HPLC (ammonium bicarbonate modifier) to afford the title compound (92 mg, 0.08 mmol, 58% yield. LCMS RT=1.25 min, ES+ve 578 ([M+2H]$^{2+}$).

Tert-butyl ((S)-1-(((S)-1-((S)-7-((6-(4-(((6-(tert-butylsulfonyl)-4-((4,5-dimethyl-1H-pyrazol-3-yl)amino)quinazolin-7-yl)oxy)methyl)piperidin-1-yl)pyrimidin-4-yl)oxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate

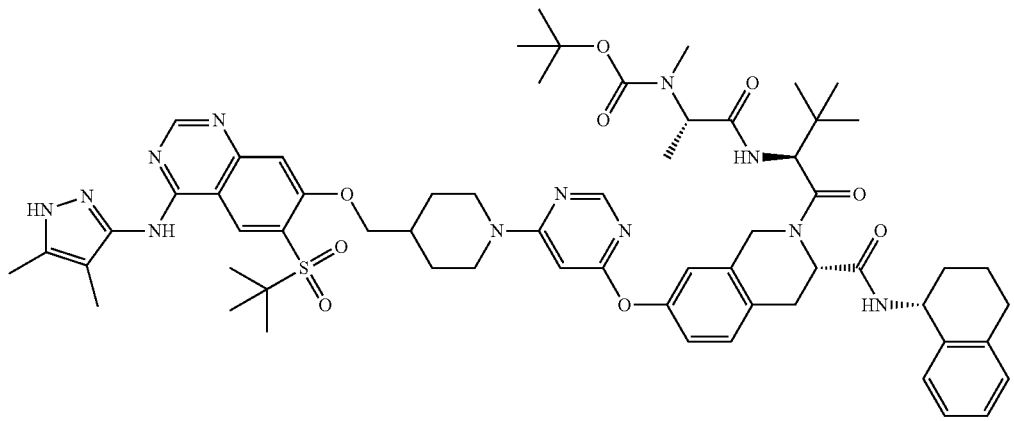 [SMILES: Cc1[nH]nc(Nc2ncnc3cc(OCC4CCN(c5cc(Oc6ccc7c(c6)CN(C(=O)[C@@H](NC(=O)[C@H](C)N(C)C(=O)OC(C)(C)C)C(C)(C)C)[C@H](C(=O)N[C@@H]6CCCc8ccccc86)C7)ncn5)CC4)c(S(=O)(=O)C(C)(C)C)cc23)c1C]

The title compound was prepared in a method analogous to that for tert-butyl ((S)-1-(((S)-1-((S)-7-((6-(4-(((6-(tert-butylsulfonyl)-4-((4,5-dimethyl-1H-pyrazol-3-yl)amino)quinazolin-7-yl)oxy)piperidin-1-yl)pyrimidin-4-yl)oxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate. 42% yield. LCMS RT=1.25 min, ES+ve 585 ([M+2H]$^{2+}$).

Tert-butyl ((S)-1-(((S)-2-((2S,4S)-4-((2-chloropyrimidin-5-yl)oxy)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate

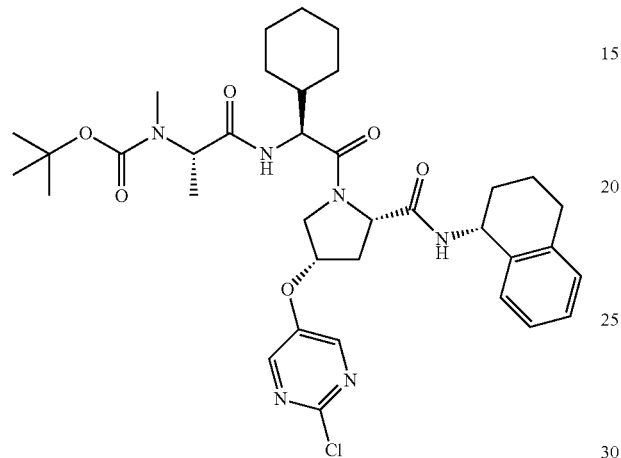

Under an atmosphere of nitrogen, an ice-cooled solution of a mixture of tert-butyl ((S)-1-(((S)-1-cyclohexyl-2-((2S,4R)-4-hydroxy-2-(((R)-1,2,3,4-tetrahydronaphthalen-1-yl)carbamoyl)pyrrolidin-1-yl)-2-oxoethyl)amino)-1-oxopropan-2-yl)(methyl)carbamate (600 mg, 1.0 mmol), 2-chloropyrimidin-5-ol (161 mg, 1.2 mmol) and triphenylphosphine (404 mg, 1.5 mmol) in tetrahydrofuran (15 mL) was treated dropwise over 1 minute with DIAD (0.3 mL, 1.5 mmol). The mixture was then stirred at room temperature for 6 hours and subsequently treated with dichloromethane (40 mL) and water (10 mL). The organic phase was evaporated to dryness and the product was purified by chromatography on silica using a gradient elution from 0-100% ethyl acetate in cyclohexane followed by 0-5% methanol in ethyl acetate to afford the title compound (525 mg, 0.75 mmol, 73% yield). LCMS RT=1.38 min, ES+ve 697.

Tert-butyl (M-1-(((S)-2-((2S,4S)-4-((2-(4-(((6-(tert-butylsulfonyl)-4-((4,5-dimethyl-1H-pyrazol-3-yl)amino)quinazolin-7-yl)oxy)methyl)piperidin-1-yl)pyrimidin-5-yl)oxy)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate

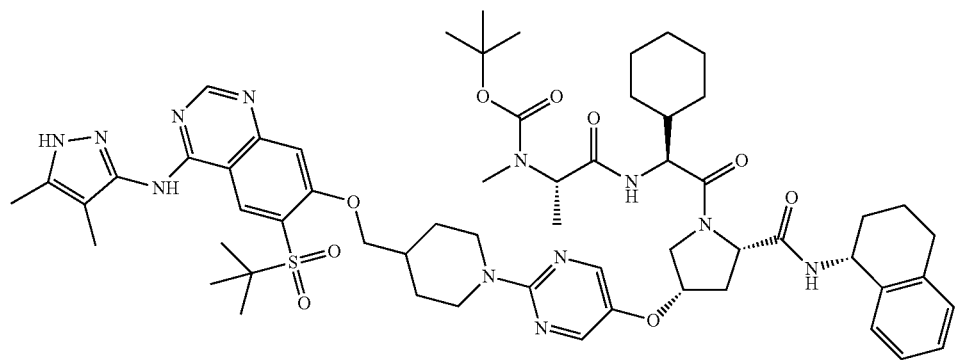 [SMILES: Cc1[nH]nc(Nc2ncnc3cc(OCC4CCN(c5ncc(O[C@H]6C[C@@H](C(=O)N[C@@H]7CCCc8ccccc87)N(C(=O)[C@@H](NC(=O)[C@H](C)N(C)C(=O)OC(C)(C)C)C7CCCCC7)C6)cn5)CC4)c(S(=O)(=O)C(C)(C)C)cc23)c1C]

To a solution of 6-(tert-butylsulfonyl)-N-(4,5-dimethyl-1H-pyrazol-3-yl)-7-(piperidin-4-ylmethoxy)quinazolin-4-amine (41 mg, 0.086 mmol) in N-methyl-2-pyrrolidone (1 mL) was added tert-butyl ((S)-1-(((S)-2-((2S,4S)-4-((2-chloropyrimidin-5-yl)oxy)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate (60 mg, 0.086 mmol) and sodium bicarbonate (29 mg, 0.34 mmol). The reaction mixture was heated to 100° C. for 18 hours then the product was subjected directly to purification by mass-directed automated preparative HPLC (formic acid modifier) to afford the title compound (43 mg, 0.04 mmol, 44% yield). LCMS RT=1.27 min, ES+ve 567 ([M+2H]$^{2+}$).

The following compounds were prepared in a method analogous to that for tert-butyl ((S)-1-(((S)-2-((2S,4S)-4-((2-(4-(((6-(tert-butylsulfonyl)-4-((4,5-dimethyl-1H-pyrazol-3-yl)amino)quinazolin-7-yl)oxy)methyl)piperidin-1-yl)pyrimidin-5-yl)oxy)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate:

| Compound Name/Structure | Yield | LCMS RT | ES +ve |
|---|---|---|---|
| Tert-butyl ((S)-1-(((S)-2-((2S,4S)-4-((2-(4-(((6-(tert-butylsulfonyl)-4-((4,5-dimethyl-1H-pyrazol-3-yl)amino)quinazolin-7-yl)oxy)piperidin-1-yl)pyrimidin-5-yl)oxy)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate 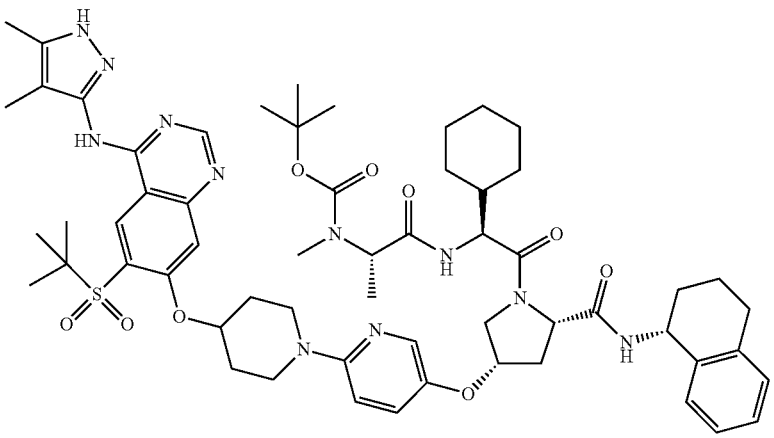 [SMILES: Cc1[nH]nc(Nc2ncnc3cc(OC4CCN(c5ccc(O[C@H]6C[C@@H](C(=O)N[C@@H]7CCCc8ccccc87)N(C(=O)[C@@H](NC(=O)[C@H](C)N(C)C(=O)OC(C)(C)C)C7CCCCC7)C6)cn5)CC4)c(S(=O)(=O)C(C)(C)C)cc23)c1C] | 59% | Method B 1.44 min | 1119.4 |
| Tert-butyl ((S)-1-(((S)-2-((2S,4S)-4-((2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidin-5-yl)oxy)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate | 40% | Method A 1.01 min | 574.9 [M + 2H]$^{2+}$ |
| Tert-butyl((S)-1-(((S)-2-((2S,4S)-4-((2-(4-(2-((6-(tert-butylsulfonyl)-4-((4,5-dimethyl-1H-pyrazol-3-yl)amino)quinazolin-7-yl)oxy)ethyl)piperidin-1-yl)pyrimidin-5-yl)oxy)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate 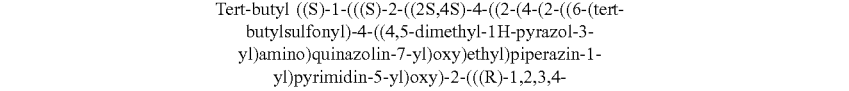 | 39% | Method A 1.29 min | 574.4 [M + 2H]$^{2+}$ |

-continued

| Compound Name/Structure | Yield | LCMS RT | ES +ve |
|---|---|---|---|
| 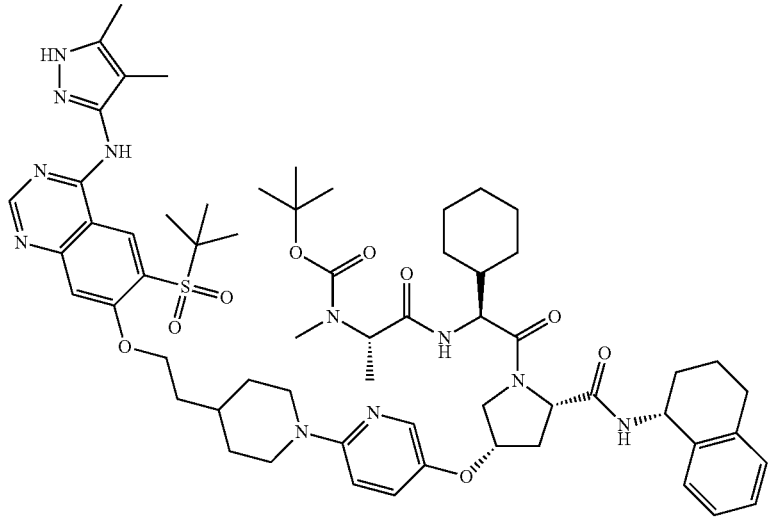 [SMILES: Cc1[nH]nc(Nc2ncnc3cc(OCCC4CCN(c5ccc(O[C@H]6C[C@@H](C(=O)N[C@@H]7CCCc8ccccc87)N(C(=O)[C@@H](NC(=O)[C@H](C)N(C)C(=O)OC(C)(C)C)C7CCCCC7)C6)cn5)CC4)c(S(=O)(=O)C(C)(C)C)cc23)c1C]<br>Tert-butyl ((S)-1-(((S)-2-((2S,4S)-4-((2-(4-(3-((6-(tert-butylsulfonyl)-4-((4,5-dimethyl-1H-pyrazol-3-yl)amino)quinazolin-7-yl)oxy)propyl)piperidin-1-yl)pyrimidin-5-yl)oxy)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate | 41% | Method A 1.33 min | 581.4 [M + 2H]²⁺ |
| 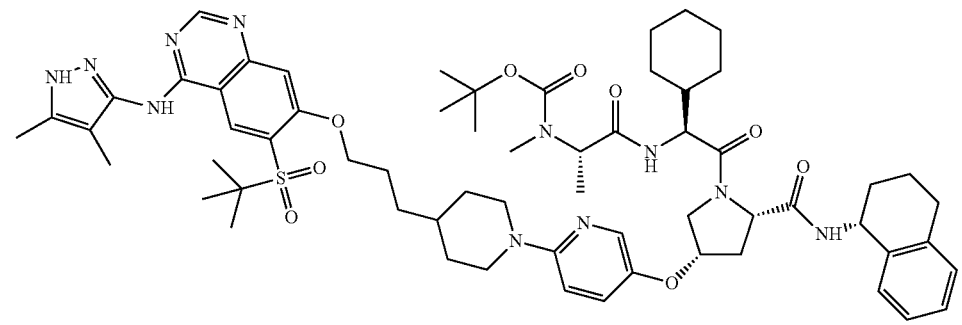 [SMILES: Cc1[nH]nc(Nc2ncnc3cc(OCCCC4CCN(c5ccc(O[C@H]6C[C@@H](C(=O)N[C@@H]7CCCc8ccccc87)N(C(=O)[C@@H](NC(=O)[C@H](C)N(C)C(=O)OC(C)(C)C)C7CCCCC7)C6)cn5)CC4)c(S(=O)(=O)C(C)(C)C)cc23)c1C]<br>Tert-butyl ((S)-1-(((S)-1-((2S,4S)-4-((2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidin-5-yl)oxy)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate | 39% | Method B 1.34 min | 1122.4 |
| 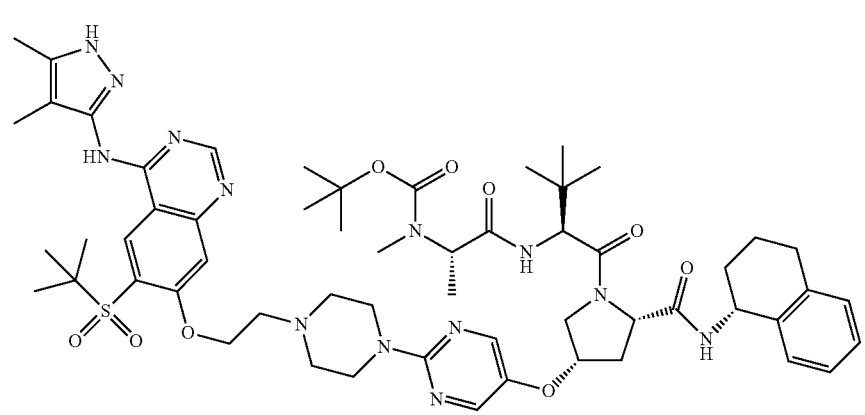 [SMILES: Cc1[nH]nc(Nc2ncnc3cc(OCCN4CCN(c5ncc(O[C@H]6C[C@@H](C(=O)N[C@@H]7CCCc8ccccc87)N(C(=O)[C@@H](NC(=O)[C@H](C)N(C)C(=O)OC(C)(C)C)C(C)(C)C)C6)cn5)CC4)c(S(=O)(=O)C(C)(C)C)cc23)c1C] | | | |

| Compound Name/Structure | Yield | LCMS RT | ES +ve |
|---|---|---|---|
| Tert-butyl ((S)-1-(((S)-1-((2S,4S)-4-((2-(4-(2-((6-tert-butylsulfonyl)-4-((4,5-dimethyl-1H-pyrazol-3-yl)amino)quinazolin-7-yl)oxy)ethyl)piperazin-1-yl)pyrimidin-5-yl)oxy)-2-((2,6-difluorophenyl)carbamoyl)pyrrolidin-1-yl)-3,3-dimethyl-1-oxobutan-2-yl)amino)-1-oxopropan-2-yl)(methyl)carbamate | 43% | Method B 1.26 min | 1104.3 |

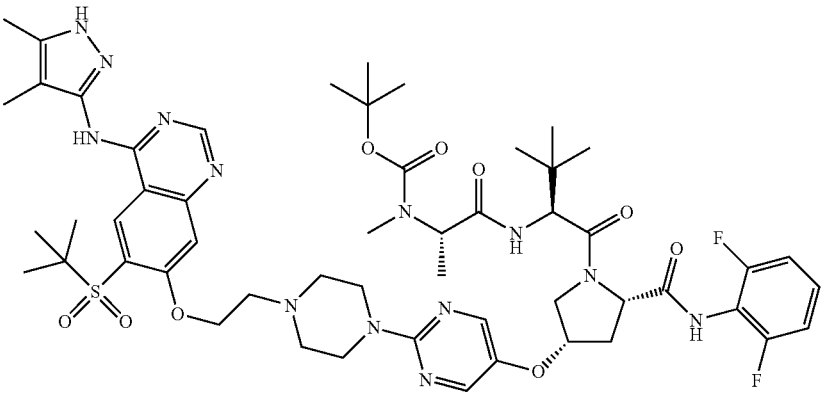 [SMILES: Cc1[nH]nc(Nc2ncnc3cc(OCCN4CCN(c5ncc(O[C@H]6C[C@@H](C(=O)Nc7c(F)cccc7F)N(C(=O)[C@@H](NC(=O)[C@H](C)N(C)C(=O)OC(C)(C)C)C(C)(C)C)C6)cn5)CC4)c(S(=O)(=O)C(C)(C)C)cc23)c1C]

6-(Tert-butylsulfonyl)-7-(2-(2-chloroethoxy)ethoxy)-N-(4,5-dimethyl-1H-pyrazol-3-yl)quinazolin-4-amine

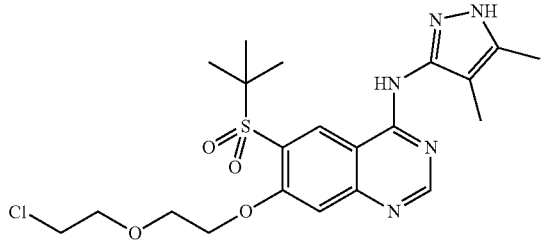 [SMILES: Cc1[nH]nc(Nc2ncnc3cc(OCCOCCCl)c(S(=O)(=O)C(C)(C)C)cc23)c1C]

To a solution of 6-(tert-butylsulfonyl)-4-((4,5-dimethyl-1H-pyrazol-3-yl)amino)quinazolin-7-ol (50 mg, 0.13 mmol, obtained as described in WO 2014/128622) in DMSO (0.8 mL) was added 1-chloro-2-(2-chloroethoxy)ethane (38.1 mg, 0.266 mmol), sodium iodide (2.0 mg, 0.013 mmol) and potassium carbonate (55 mg, 0.40 mmol) and the reaction mixture was sealed and stirred at 80° C. in a Biotage microwave for 3 h. The product was subjected directly to purification by mass-directed automated preparative HPLC (formic acid modifier) to afford the title compound (27 mg, 0.06 mmol, 42% yield). LCMS RT=0.72 min, ES+ve 482.

Tert-butyl ((S)-1-(((S)-2-((2S,4S)-4-(5-(4-(2-((6-(tert-butylsulfonyl)-4-((4,5-dimethyl-1H-pyrazol-3-yl)amino)quinazolin-7-yl)oxy)ethyl)piperazin-1-yl)pyrazine-2-carboxamido)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate

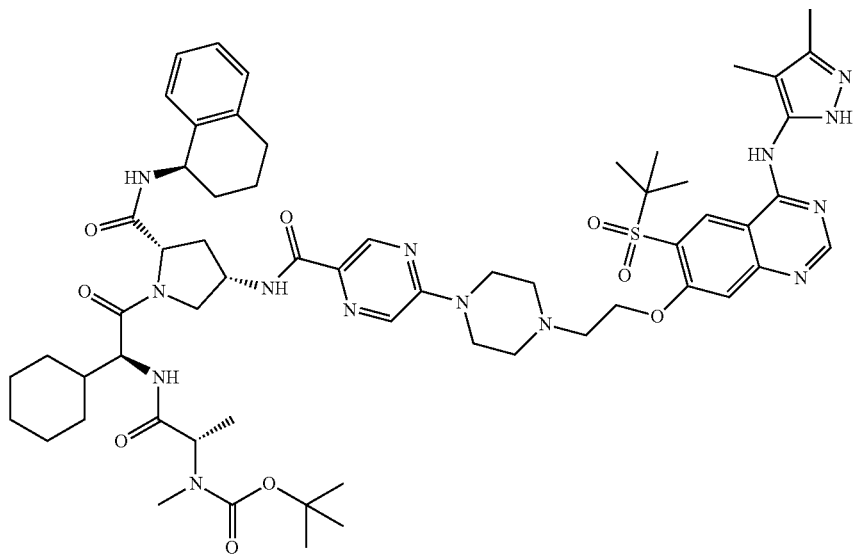 [SMILES: Cc1n[nH]c(Nc2ncnc3cc(OCCN4CCN(c5cnc(C(=O)N[C@H]6C[C@@H](C(=O)N[C@@H]7CCCc8ccccc87)N(C(=O)[C@@H](NC(=O)[C@H](C)N(C)C(=O)OC(C)(C)C)C7CCCCC7)C6)cn5)CC4)c(S(=O)(=O)C(C)(C)C)cc23)c1C]

HATU (92 mg, 0.241 mmol) was added to a mixture of DIPEA (0.1 mL, 0.57 mmol), 5-(4-(2-(((6-(tert-butylsulfonyl)-4-((4,5-dimethyl-1H-pyrazol-3-yl)amino)quinazolin-7-yl)oxy)ethyl)piperazin-1-yl)pyrazine-2-carboxylic acid (70 mg, 0.115 mmol) and tert-butyl ((S)-1-(((S)-2-((2S,4S)-4-amino-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate (78 mg, 0.13 mmol, obtained as described in WO 2014090709 A1) in DMF (0.55 mL). The reaction mixture was stirred at ambient temperature for 1.5 h. The product was subjected directly to purification by mass-directed automated preparative HPLC (formic acid modifier) to afford the title compound (74 mg, 0.06 mmol, 55% yield). LCMS Method B RT=1.32 min, ES+ve 1175.

The following compounds were prepared in a method analogous to that for tert-butyl ((S)-1-(((S)-2-((2S,4S)-4-(5-(4-(2-(((6-(tert-butylsulfonyl)-4-((4,5-dimethyl-1H-pyrazol-3-yl)amino)quinazolin-7-yl)oxy)ethyl)piperazin-1-yl)pyrazine-2-carboxamido)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate:

| Compound Name/Structure | Yield | LCMS RT | ES +ve |
|---|---|---|---|
| Tert-butyl ((S)-1-(((S)-2-((2S,4S)-4-(2-(4-(2-(((6-(tert-butylsulfonyl)-4-((4,5-dimethyl-1H-pyrazol-3-yl)amino)quinazolin-7-yl)oxy)ethyl)piperazin-1-yl)pyrimidine-5-carboxamido)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate 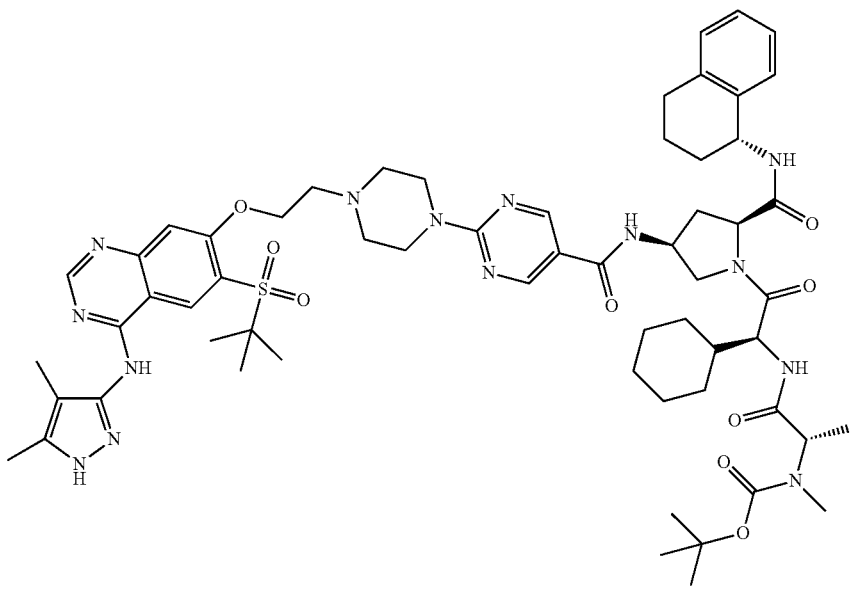 [SMILES: Cc1[nH]nc(Nc2ncnc3cc(OCCN4CCN(c5ncc(C(=O)N[C@H]6C[C@@H](C(=O)N[C@@H]7CCCc8ccccc87)N(C(=O)[C@@H](NC(=O)[C@H](C)N(C)C(=O)OC(C)(C)C)C7CCCCC7)C6)cn5)CC4)c(S(=O)(=O)C(C)(C)C)cc23)c1C] | 8% | Method B 1.34 min | 1175.36 |
| Tert-butyl ((S)-1-(((S)-2-((2S,4S)-4-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carboxamido)-2-(((R)-1,2,3,4-Tetrahydronaphthalen-1-yl)carbamoyl)pyrrolidin-1-yl)-1-cyclohexyl-2-oxoethyl)amino)-1-oxopropan-2-yl)(methyl)carbamate | 98% | Method B 1.39 min | 1160.3 |

| Compound Name/Structure | Yield | LCMS RT | ES +ve |
|---|---|---|---|
| 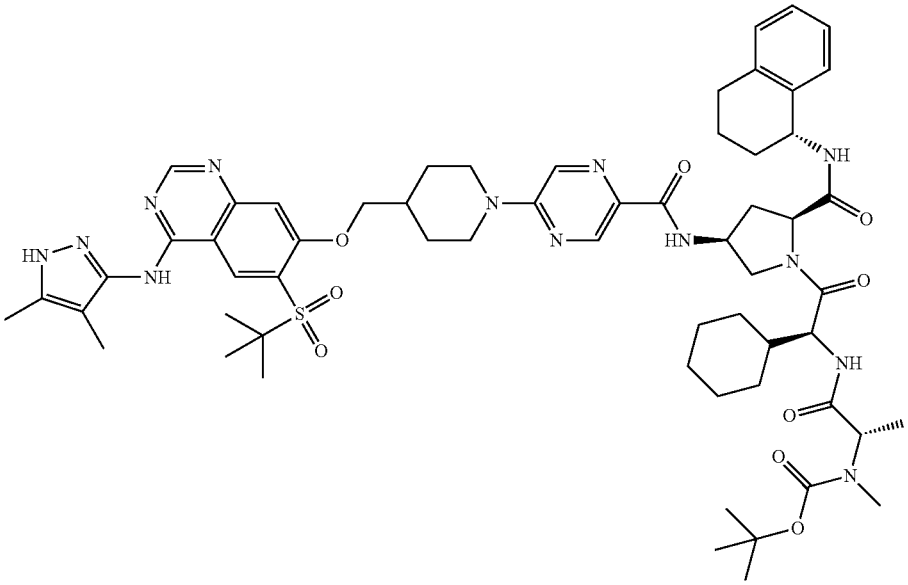 [SMILES: Cc1[nH]nc(Nc2ncnc3cc(OCC4CCN(c5cnc(C(=O)N[C@H]6C[C@@H](C(=O)N[C@@H]7CCCc8ccccc87)N(C(=O)[C@@H](NC(=O)[C@H](C)N(C)C(=O)OC(C)(C)C)C7CCCCC7)C6)cn5)CC4)c(S(=O)(=O)C(C)(C)C)cc23)c1C]<br>Tert-butyl ((S)-1-(((S)-2-((2S,4S)-4-(6-(4-(3-((6-(tert-butylsulfonyl)-4-((4,5-dimethyl-1H-pyrazol-3-yl)amino)quinazolin-7-yl)oxy)propyl)piperidin-1-yl)nicotinamido)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate | 97% | Method B 1.47 min | 1188.69 |
| 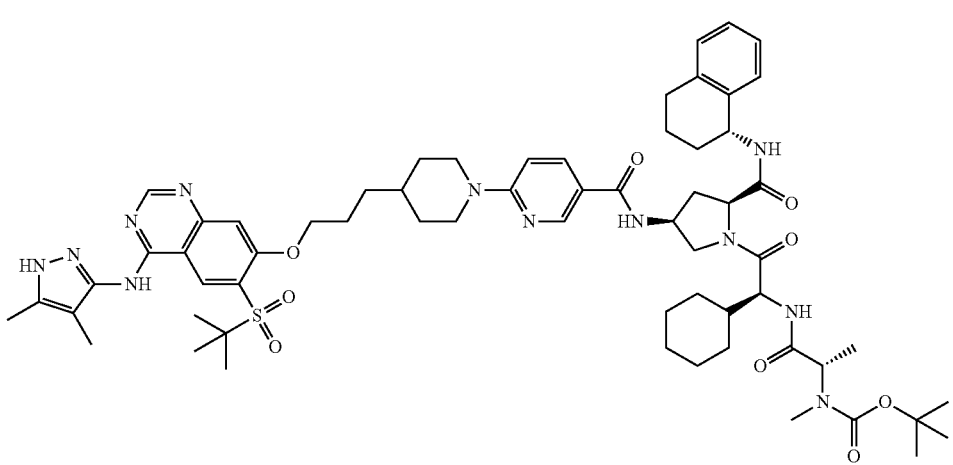<br>Tert-butyl ((S)-1-(((S)-2-((2S,4S)-4-(2-(4-(((6-(tert-butylsulfonyl)-4-((4,5-dimethyl-1H-pyrazol-3-yl)amino)quinazolin-7-yl)oxy)methyl)piperidin-1-yl)pyrimidine-5-carboxamido)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate | 95% | Method B 1.41 min | 1158.7 |

| Compound Name/Structure | Yield | LCMS RT | ES +ve |
|---|---|---|---|
| 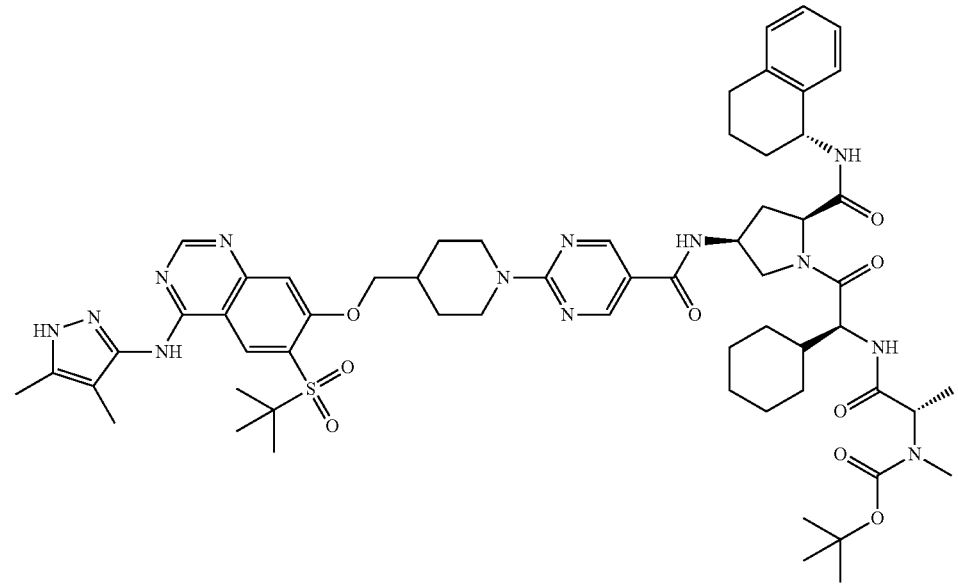 Tert-butyl ((S)-1-(((S)-2-((2S,4S)-4-(6-(4-(3-((6-(tert-butylsulfonyl)-4-((4,5-dimethyl-1H-pyrazol-3-yl)amino)quinazolin-7-yl)oxy)propyl)piperazin-1-yl)nicotinamido)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate | 11% | Method B 1.34 min | 1188.36 |
| 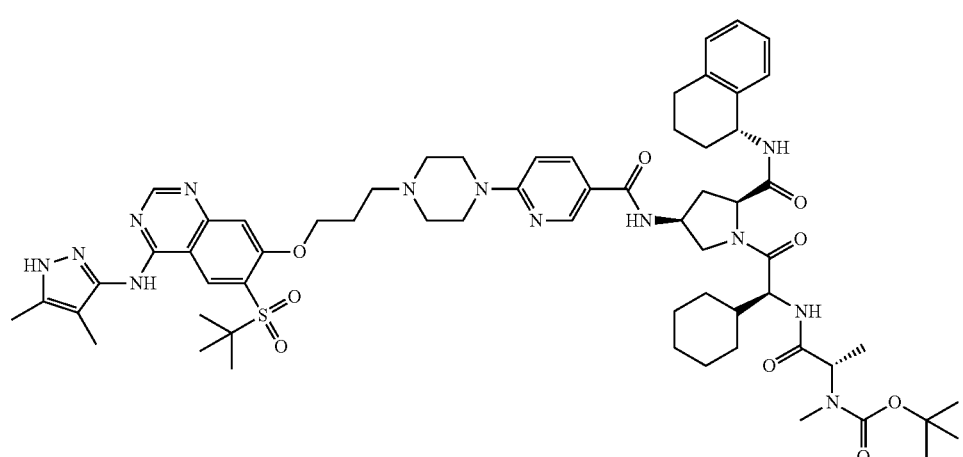 Tert-butyl ((S)-1-(((S)-2-((2S,4S)-4-(2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidine-5-carboxamido)-2-((3-methyl-1-phenyl-1H-pyrazol-5-yl)carbamoyl)pyrrolidin-1-yl)-1-cyclohexyl-2-oxoethyl)amino)-1-oxopropan-2-yl)(methyl)carbamate | 47% | Method B 1.22 min | 1201.32 |

| Compound Name/Structure | Yield | LCMS RT | ES +ve |
|---|---|---|---|
| 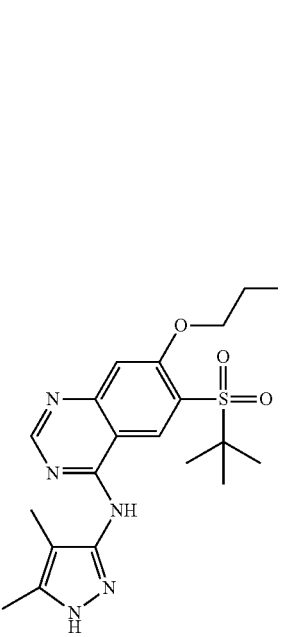<br>Tert-butyl ((S)-1-(((S)-2-((2S,4S)-4-(2-(4-(3-((6-(tert-butylsulfonyl)-4-((4,5-dimethyl-1H-pyrazol-3-yl)amino)quinazolin-7-yl)oxy)propyl)piperazin-1-yl)pyrimidine-5-carboxamido)-2-((3-methyl-1-phenyl-1H-pyrazol-5-yl)carbamoyl)pyrrolidin-1-yl)-1-cyclohexyl-2-oxoethyl)amino)-1-oxopropan-2-yl)(methyl)carbamate | 21% | Method B 1.50 min | 1215.20 |
| 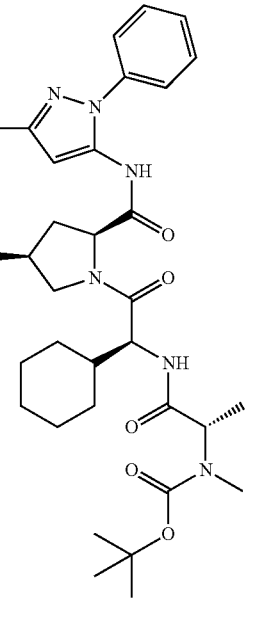<br>Tert-butyl ((S)-1-(((S)-1-((2S,4S)-4-(5-(4-(3-((6-(tert-butylsulfonyl)-4-((4,5-dimethyl-1H-pyrazol-3-yl)amino)quinazolin-7-yl)oxy)propyl)piperazin-1-yl)pyrazine-2-carboxamido)-2-((2,6-difluorophenyl)carbamoyl)pyrrolidin-1-yl)-3,3-dimethyl-1-oxobutan-2-yl)amino)-1-oxopropan-2-yl)(methyl)carbamate | | | |

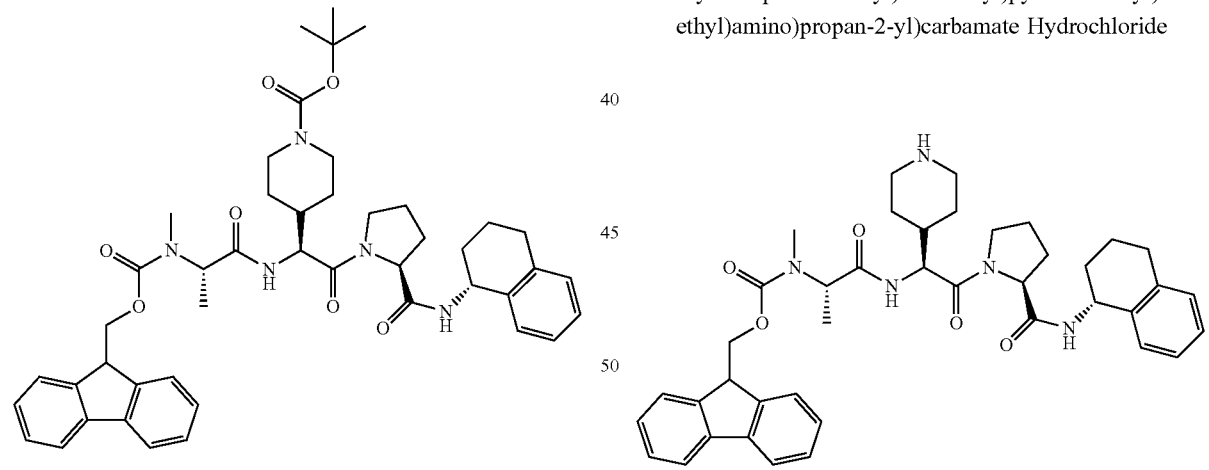

Tert-butyl 4-((S)-1-((S)-2-((((9H-fluoren-9-yl)methoxy)carbonyl)(methyl)amino)propanamido)-2-oxo-2-((S)-2-(((R)-1,2,3,4-tetrahydronaphthalen-1-yl)carbamoyl)pyrrolidin-1-yl)ethyl)piperidine-1-carboxylate A mixture of (S)-N-((R)-1,2,3,4-tetrahydronaphthalen-1-yl)pyrrolidine-2-carboxamide, Hydrochloride (68 mg, 0.24 mmol, obtained as described in patent WO 2006/017295 A2) and (S)-2-((S)-2-((((9H-fluoren-9-yl)methoxy)carbonyl)(methyl)amino)propanamido)-2-(1-(tert-butoxycarbonyl)piperidin-4-yl)acetic acid (137 mg, 0.24 mmol, obtained as described in patent WO 2008/134679 A1) in DMF (2 mL) was treated with DIPEA (0.085 mL, 0.48 mmol) followed by HATU (203 mg, 0.53 mmol). After 4 hr, the reaction was diluted with EtOAc (10 mL) and washed with water (2×10 mL) followed by brine (15 mL). The organic fraction was collected and concentrated in vacuo to obtain the title product (176 mg, 0.22 mmol, 92% yield). LCMS RT method B RT 1.47 min, ES+ve m/z 792

(9H-Fluoren-9-yl)methyl methyl((S)-1-oxo-1-(((S)-2-oxo-1-(piperidin-4-yl)-2-((S)-2-(((R)-1,2,3,4-tetrahydronaphthalen-1-yl)carbamoyl)pyrrolidin-1-yl)ethyl)amino)propan-2-yl)carbamate Hydrochloride Tert-butyl 4-((S)-1-((S)-2-((((9H-fluoren-9-yl)methoxy)carbonyl)(methyl)amino)propanamido)-2-oxo-2-((S)-2-(((R)-1,2,3,4-tetrahydronaphthalen-1-yl)carbamoyl)pyrrolidin-1-yl)ethyl)piperidine-1-carboxylate (176 mg, 0.22 mmol) was treated with 4M HCl in dioxane (1 mL, 4 mmol). After 3 hr the reaction mixture was concentrated in vacuo to afford the title compound (160 mg, 0.22 mmol, 91% yield). LCMS RT (Method B) RT 1.27 min, ES+ve m/z 692

(9H-Fluoren-9-yl)methyl ((S)-1-(((S)-1-(1-(2-(4-(2-
((6-(tert-butylsulfonyl)-4-((4,5-dimethyl-1H-pyra-
zol-3-yl)amino)quinazolin-7-yl)oxy)ethyl)piperazin-
1-yl)pyrimidine-5-carbonyl)piperidin-4-yl)-2-oxo-2-
((S)-2-(((R)-1,2,3,4-tetrahydronaphthalen-1-yl)
carbamoyl)pyrrolidin-1-yl)ethyl)amino)-1-
oxopropan-2-yl)(methyl)carbamate

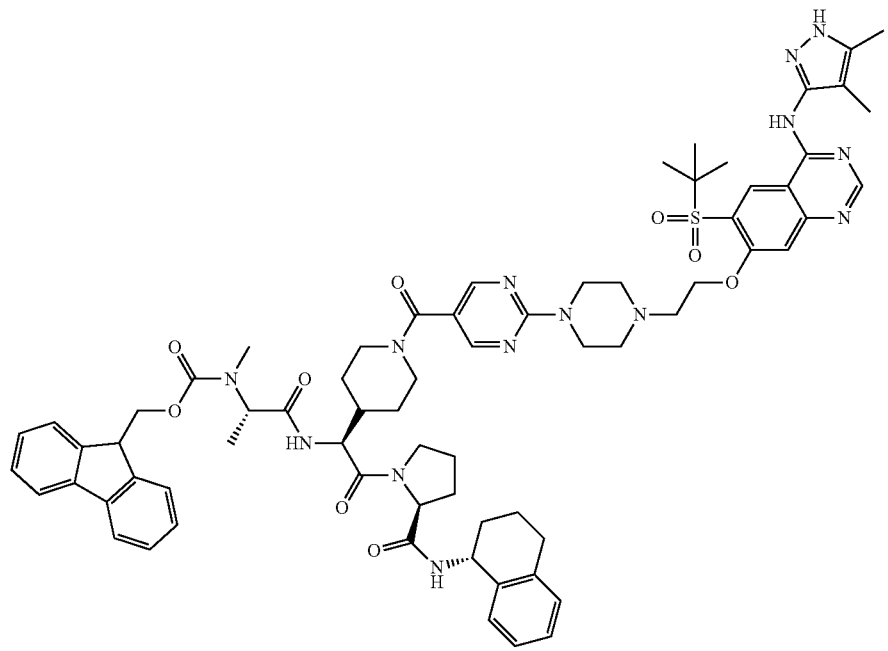 [SMILES: Cc1[nH]nc(Nc2ncnc3cc(OCCN4CCN(c5ncc(C(=O)N6CCC([C@H](NC(=O)[C@H](C)N(C)C(=O)OCC7c8ccccc8-c8ccccc87)C(=O)N7CCC[C@H]7C(=O)N[C@@H]7CCCc8ccccc87)CC6)cn5)CC4)c(S(=O)(=O)C(C)(C)C)cc23)c1C]

2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidine-5-carboxylic acid (126 mg, 0.21 mmol) and (9H-fluoren-9-yl)methyl methyl((S)-1-oxo-1-(((S)-2-oxo-1-(piperidin-4-yl)-2-((S)-2-(((R)-1,2,3,4-tetrahydronaphthalen-1-yl)carbamoyl)pyrrolidin-1-yl)ethyl)amino)propan-2-yl)carbamate, Hydrochloride (151 mg, 0.21 mmol) were dissolved in DMF (1 mL). and treated with DIPEA (0.144 mL, 0.83 mmol) and then with HATU (157 mg, 0.41 mmol). After 2 hr the crude product was purified by mass-directed automated preparative HPLC (ammonium bicarbonate modifier) to afford the title compound (40 mg, 0.031 mmol, 15% yield). LCMS Method B RT=1.29 min, ES+ve 642 ([M+2H]$^{2+}$).

(5S,8S,10aR)-methyl 5-((tert-butoxycarbonyl)amino)-3-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)-6-oxodecahydropyrrolo[1,2-a][1,5]diazocine-8-carboxylate

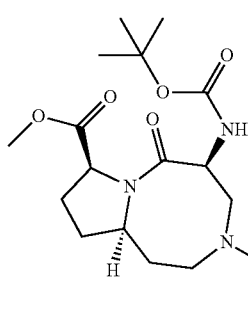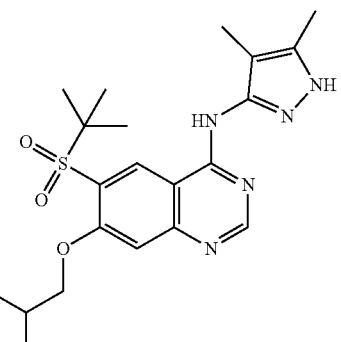

A mixture of (5S,8S,10aR)-methyl 5-((tert-butoxycarbonyl)amino)-6-oxodecahydropyrrolo[1,2-a][1,5]diazocine-8-carboxylate (183 mg, 0.54 mmol, obtained as described in the patent WO 2011/050068 A2) and 5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carboxylic acid (213 mg, 0.36 mmol) were dissolved in DMF (2 mL) and treated with DIPEA (0.25 mL, 1.43 mmol) followed by HATU (163 mg, 0.43 mmol). After 1 hr the crude reaction mixture was loaded directly onto a 60 g C18 column and purified using a 5-70% acetonitrile in water (ammonium bicarbonate modifier) to afford the title product (168 mg, 0.18 mmol, 51% yield) LCMS method B RT 1.08 min, ES+ve m/z 918.

(5S,8S,10aR)-Methyl 5-amino-3-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)-6-oxodecahydropyrrolo[1,2-a][1,5]diazocine-8-carboxylate

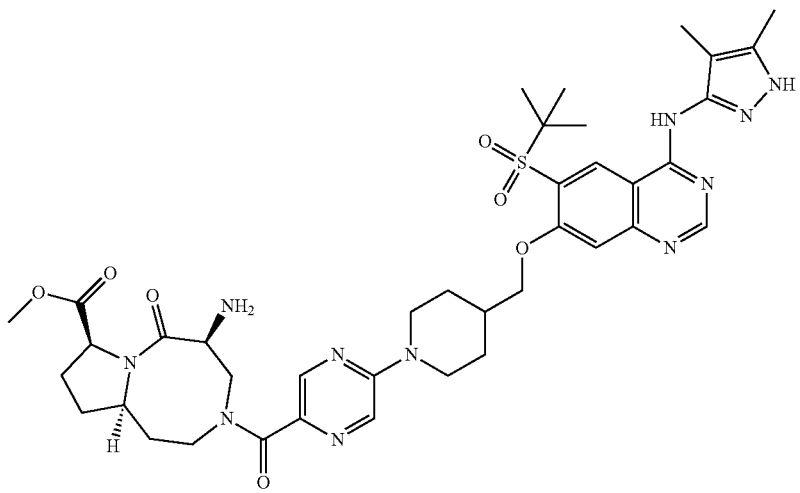

(5S,8S,10aR)-Methyl 5-((tert-butoxycarbonyl)amino)-3-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)-6-oxodecahydropyrrolo[1,2-a][1,5]diazocine-8-carboxylate was treated with trifluoroacetic acid (4 mL). After 1 hr the reaction mixture was concentrated in vacuo and the residue was dissolved in MeOH (5 mL) and eluted through a 1 g amino propyl cartridge with methanol to afford the title compound (220 mg, 0.27 mmol, 75% yield). LCMS method B RT 0.89 min, ES+ve m/z 818

(5S,13S,10aR)-5-((S)-2-((Tert-butoxycarbonyl)(methyl)amino)propanamido)-3-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)-6-oxodecahydropyrrolo[1,2-a][1,5]diazocine-8-carboxylic Acid

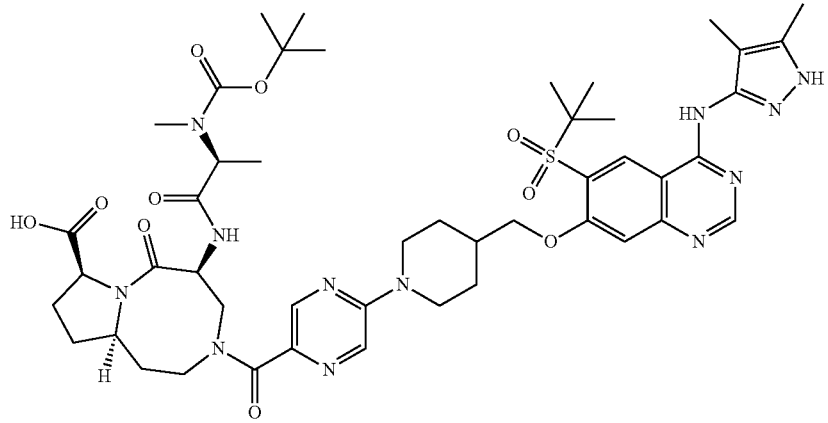 [SMILES: Cc1[nH]nc(Nc2ncnc3cc(OCC4CCN(c5cnc(C(=O)N6CC[C@H]7CC[C@@H](C(=O)O)N7C(=O)[C@@H](NC(=O)[C@H](C)N(C)C(=O)OC(C)(C)C)C6)cn5)CC4)c(S(=O)(=O)C(C)(C)C)cc23)c1C]

A mixture of (S)-2-((tert-butoxycarbonyl)(methyl)amino) propanoic acid (57.4 mg, 0.28 mmol) and (5S,8S,10aR)-methyl 5-amino-3-(5-(4-(((6-(tert-butylsulfonyl)-4-((4,5-dimethyl-1H-pyrazol-3-yl)amino)quinazolin-7-yl)oxy) methyl)piperidin-1-yl)pyrazine-2-carbonyl)-6-oxodecahydropyrrolo[1,2-a][1,5]diazocine-8-carboxylate (220 mg, 0.27 mmol) in DMF (1.35 mL) was treated with DIPEA (0.188 mL, 1.076 mmol) followed by HATU (112 mg, 0.30 mmol). After 4 hr 2M aqueous NaOH (3 mL, 6 mmol) was added. After a further 0.5 hr the reaction mixture was concentrated in vacuo, loaded on to a 60 g C18 column and purified using a 5-60% gradient using acetonitrile/water (ammonium bicarbonate modifier) to afford the title compound (105 mg, 0.11 mmol, 40% yield). LCMS RT method B RT 0.82 min, ES+ve m/z 989.

Tert-butyl ((S)-1-(((5S,8S,10aR)-8-(benzhydrylcarbamoyl)-3-(5-(4-(((6-(tert-butylsulfonyl)-4-((4,5-dimethyl-1H-pyrazol-3-yl)amino)quinazolin-7-yl) oxy)methyl)piperidin-1-yl)pyrazine-2-carbonyl)-6-oxodecahydropyrrolo[1,2-a][1,5]diazocin-5-yl) amino)-1-oxopropan-2-yl)(methyl)carbamate

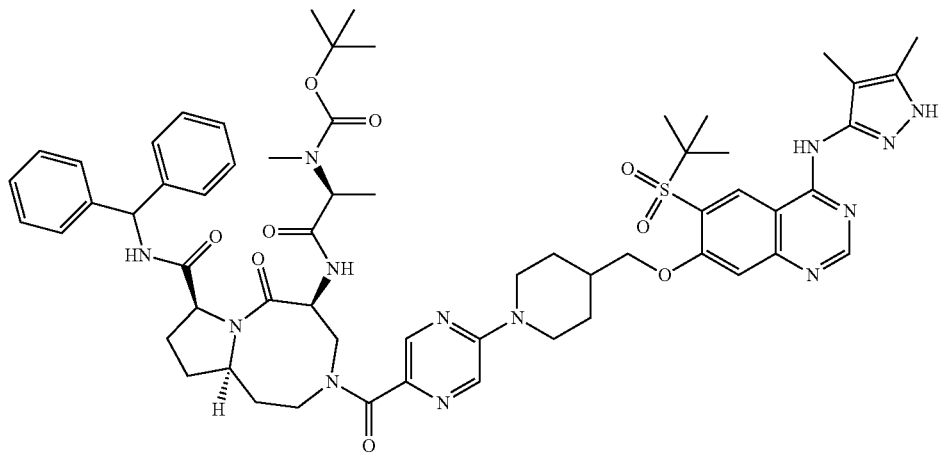 [SMILES: Cc1[nH]nc(Nc2ncnc3cc(OCC4CCN(c5cnc(C(=O)N6CC[C@H]7CC[C@@H](C(=O)NC(c8ccccc8)c8ccccc8)N7C(=O)[C@@H](NC(=O)[C@H](C)N(C)C(=O)OC(C)(C)C)C6)cn5)CC4)c(S(=O)(=O)C(C)(C)C)cc23)c1C]

A solution of (5S,8S,10aR)-5-((S)-2-((tert-butoxycarbonyl)(methyl)amino)propanamido)-3-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)-6-oxodecahydropyrrolo[1,2-a][1,5]diazocine-8-carboxylic acid (40 mg, 0.04 mmol) and diphenylmethanamine (8 μl, 0.044 mmol) in DMF (0.3 mL) was treated with DIPEA (0.021 mL, 0.12 mmol) followed by HATU (17 mg, 0.044 mmol). After 2 hr the crude product was purified by mass-directed automated preparative HPLC (ammonium bicarbonate modifier) to afford the title compound (24 mg, 0.021 mmol, 51 yield). LCMS method B RT 1.26 min, ES+ve m/z 1155.

Using a method analogous to that for tert-butyl ((S)-1-(((5S,8S,10aR)-8-(benzhydrylcarbamoyl)-3-(5-(4-(((6-(tert-butylsulfonyl)-4-((4,5-dimethyl-1H-pyrazol-3-yl)amino) quinazolin-7-yl)oxy)methyl)piperidin-1-yl)pyrazine-2-carbonyl)-6-oxodecahydropyrrolo[1,2-a][1,5]diazocin-5-yl) amino)-1-oxopropan-2-yl)(methyl)carbamate the following compound was prepared:

| Compound Name/Structure | Yield | LCMS RT | ES +ve |
|---|---|---|---|
| Tert-butyl ((S)-1-(((5S,8S,10aR)-3-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)-6-oxo-8-(((R)-1,2,3,4-tetrahydronaphthalen-1-yl)carbamoyl)decahydropyrrolo[1,2-a][1,5]diazocin-5-yl)amino)-1-oxopropan-2-yl)(methyl)carbamate | 32% | Method B 1.21 min | 1118.3 |

| Compound Name/Structure | Yield | LCMS RT | ES +ve |
|---|---|---|---|
| 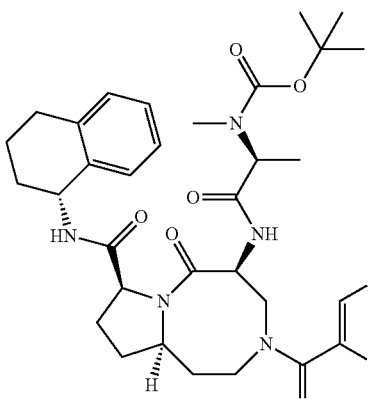 Tert-butyl ((S)-1-(((5S,8S,10aR)-3-(5-(4-(3-((6-(tert-butylsulfonyl)-4-((4,5-dimethyl-1H-pyrazol-3-yl)amino)quinazolin-7-yl)oxy)propyl)piperazin-1-yl)pyrazine-2-carbonyl)-6-oxo-8-(((R)-1,2,3,4-tetrahydronaphthalen-1-yl)carbamoyl)decahydropyrrolo[1,2-a][1,5]diazocin-5-yl)amino)-1-oxopropan-2-yl)(methyl)carbamate | 20% | Method B 1.17 min | 1147.4 |
| 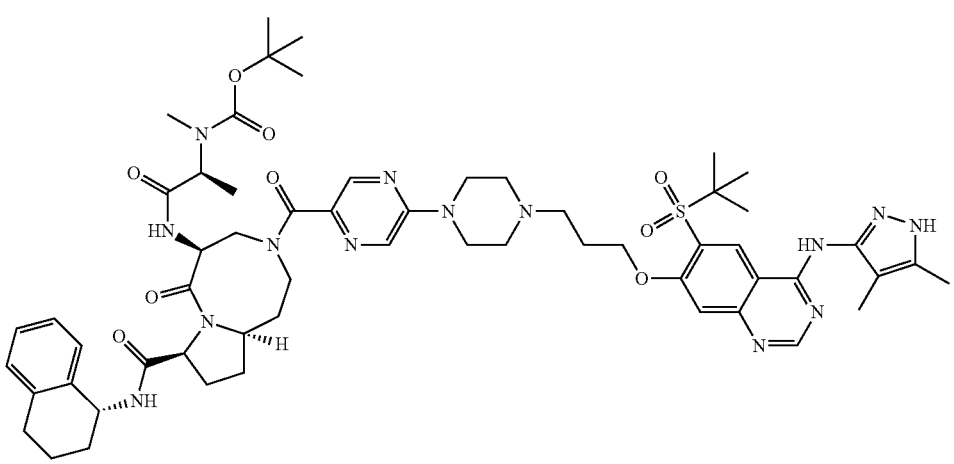 [SMILES: Cc1[nH]nc(Nc2ncnc3cc(OCCCN4CCN(c5cnc(C(=O)N6CC[C@H]7CC[C@@H](C(=O)N[C@@H]8CCCc9ccccc98)N7C(=O)[C@@H](NC(=O)[C@H](C)N(C)C(=O)OC(C)(C)C)C6)cn5)CC4)c(S(=O)(=O)C(C)(C)C)cc23)c1C] Tert-butyl ((S)-1-(((5S,8S,10aR)-3-(2-(4-(3-((6-(tert-butylsulfonyl)-4-((4,5-dimethyl-1H-pyrazol-3-yl)amino)quinazolin-7-yl)oxy)propyl)piperazin-1-yl)pyrimidine-5-carbonyl)-6-oxo-8-(((R)-1,2,3,4-tetrahydronaphthalen-1-yl)carbamoyl)decahydropyrrolo[1,2-a][1,5]diazocin-5-yl)amino)-1-oxopropan-2-yl)(methyl)carbamate | 19% | Method B 1.15 min | 573.5 (M + 2H)$^{2+}$ |

| Compound Name/Structure | Yield | LCMS RT | ES +ve |
|---|---|---|---|

Example 1

(S)-7-(2-(2-(2-(2-((4-(Benzo[d]thiazol-5-ylamino)-6-(tert-butylsulfonyl)quinolin-7-yl)oxy)ethoxy)ethoxy)ethoxy)ethoxy)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide, 2Hydrochloride

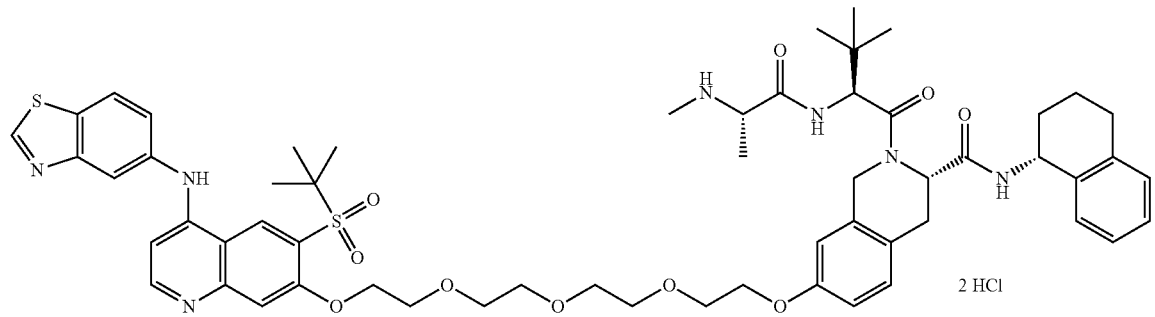 [SMILES: CN[C@@H](C)C(=O)N[C@H](C(=O)N1Cc2cc(OCCOCCOCCOCCOc3cc4nccc(Nc5ccc6scnc6c5)c4cc3S(=O)(=O)C(C)(C)C)ccc2C[C@H]1C(=O)N[C@@H]1CCCc2ccccc21)C(C)(C)C]

A solution of tert-butyl ((S)-1-(((S)-1-((S)-7-(2-(2-(2-(2-((4-(benzo[d]thiazol-5-ylamino)-6-(tert-butylsulfonyl)quinolin-7-yl)oxy)ethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (65 mg, 0.055 mmol) in THF (1.5 mL) was treated with hydrochloric acid (4M in 1,4-dioxane) (3 mL, 12 mmol) and allowed to stand overnight. The solution was evaporated to dryness and the residual product was subjected to purification by mass-directed automated preparative HPLC (ammonium bicarbonate modifier). The recovered material was dissolved in THF (1 mL), treated with 1M HCl in 1,4-dioxane (0.5 mL), evaporated and dried under vacuum to afford the title compound (45 mg, 0.039 mmol, 71% yield). LCMS RT=0.72 min, ES+ve 1093.

Example 2

(S)-7-(2-(2-(2-(2-((4-(Benzo[d]thiazol-5-ylamino)-6-(tert-butylsulfonyl)quinolin-7-yl)oxy)ethoxy)ethoxy)ethoxy)ethoxy)-2-((S)-3,3-dimethyl-2-((S)-2-(methylamino)propanamido)butanoyl)-N-((S)-1,2,3,4-tetrahydronaphthalen-1-yl)-1,2,3,4-tetrahydroisoquinoline-3-carboxamide, 2Hydrochloride

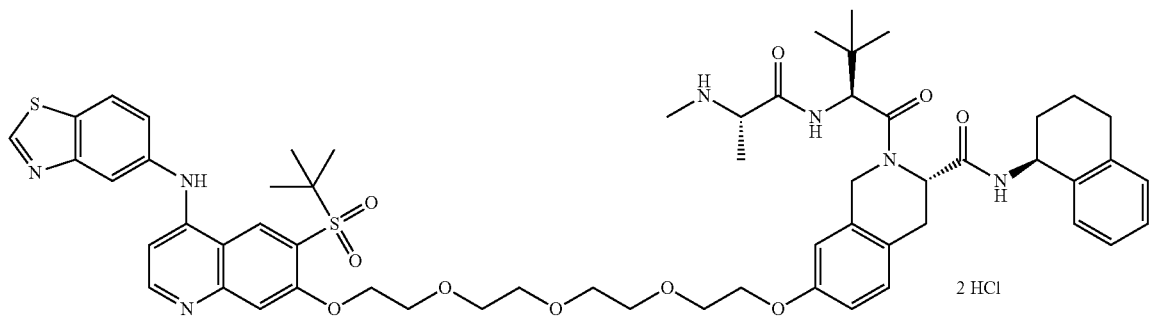 [SMILES: CN[C@@H](C)C(=O)N[C@H](C(=O)N1Cc2cc(OCCOCCOCCOCCOc3cc4nccc(Nc5ccc6scnc6c5)c4cc3S(=O)(=O)C(C)(C)C)ccc2C[C@H]1C(=O)N[C@H]1CCCc2ccccc21)C(C)(C)C]

The title compound was prepared in a method analogous to that for (S)-7-(2-(2-(2-(2-((4-(benzo[d]thiazol-5-ylamino)-6-(tert-butylsulfonyl)quinolin-7-yl)oxy)ethoxy)ethoxy)ethoxy)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide, 2Hydrochloride (Example 1) using (S)-1,2,3,4-tetrahydronaphthalen-1-amine in place of (R)-1,2,3,4-tetrahydronaphthalen-1-amine. LCMS RT=0.74 min, ES+ve 1093.

Example 3

(S)-7-(2-(2-(2-(2-((6-(Tert-butylsulfonyl)-4-((4,5-dimethyl-1H-pyrazol-3-yl)amino)quinazolin-7-yl)oxy)ethoxy)ethoxy)ethoxy)ethoxy)-2-((S)-3,3-dimethyl-2-((S)-2-(methylamino)propanamido)butanoyl)-N-(M-1,2,3,4-tetrahydronaphthalen-1-yl)-1,2,3,4-tetrahydroisoquinoline-3-carboxamide, 2Hydrochloride

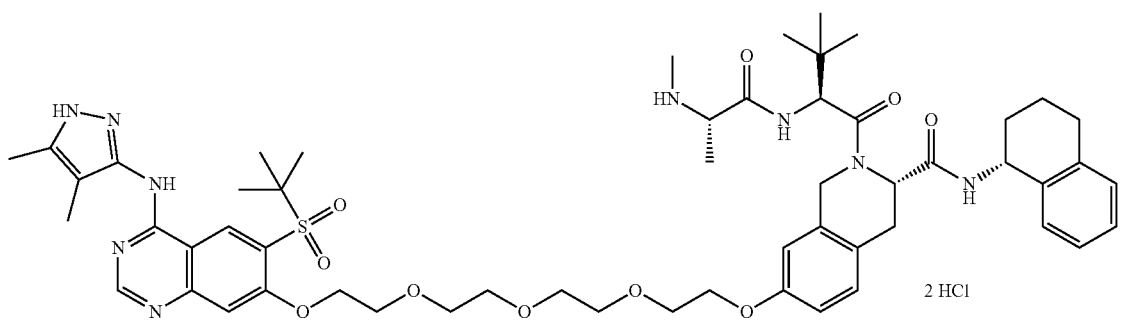 [SMILES: CN[C@@H](C)C(=O)N[C@H](C(=O)N1Cc2cc(OCCOCCOCCOCCOc3cc4ncnc(Nc5n[nH]c(C)c5C)c4cc3S(=O)(=O)C(C)(C)C)ccc2C[C@H]1C(=O)N[C@@H]1CCCc2ccccc21)C(C)(C)C]

A solution of tert-butyl ((S)-1-(((S)-1-((S)-7-(2-(2-(2-(2-((6-(tert-butylsulfonyl)-4-((4,5-dimethyl-1H-pyrazol-3-yl)amino)quinazolin-7-yl)oxy)ethoxy)ethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (380 mg, 0.33 mmol) in dichloromethane (5 mL) was treated with trifluoroacetic acid (5 mL) and stirred at ambient temperature for 30 minutes. The mixture was evaporated to dryness; the residue was then dissolved in 4 mL of THF and treated with 4M HCl in 1,4-dioxan (5 mL). After 18 hours the resulting suspension was diluted with diethyl ether (10 mL) and filtered. The filtered solid was washed with diethyl ether and dried under vacuum to afford the title compound (277 mg, 0.25 mmol, 75% yield). LCMS RT=1.17 min, ES+ve 1054.

The following compounds were prepared in a method analogous to that for (S)-7-(2-(2-(2-(2-((6-(tert-butylsulfonyl)-4-((4,5-dimethyl-1H-pyrazol-3-yl)amino)quinazolin-7-yl)oxy)ethoxy)ethoxy)ethoxy)ethoxy)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide, 2Hydrochloride:

| Compound Name/Structure | Yield | LCMS RT | ES +ve |
|---|---|---|---|
| Example 4<br>(2S,4S)-4-(14-((4-(benzo[d]thiazol-5-ylamino)-6-(tert-butylsulfonyl)quinolin-7-yl)oxy)-3,6,9,12-tetraoxatetradecanamido)-1-((S)-3,3-dimethyl-2-((S)-2-(methylamino)propanamido)butanoyl)-N-((R)-3-methylbutan-2-yl)pyrrolidine-2-carboxamide, 2 Hydrochloride | 78% | Method B 1.12 min | 1028 |
| Example 5<br>(2S,4S)-4-(14-(4-(benzo[d]thiazol-5-ylamino)-6-(tert-butylsulfonyl)quinolin-7-yl)oxy)-3,6,9,12-tetraoxatetradecanamido)-1-((S)-3,3-dimethyl-2-((S)-2-(methylamino)propanamido)butanoyl)-N-((R)-1,2,3,4-tetrahydronaphthalen-1-yl)pyrrolidine-2-carboxamide, 2 Hydrochloride | 90% | Method B 1.19 min | 1088 |
| Example 6<br>(2S,4S)-4-(14-((4-(benzo[d]thiazol-5-ylamino)-6-(tert-butylsulfonyl)quinolin-7-yl)oxy)-3,6,9,12-tetraoxatetradecanamido)-N-((R)-2,3-dihydro-1H-inden-1-yl)-1-((S)-3,3-dimethyl-2-((S)-2-(methylamino)propanamido)butanoyl)pyrrolidine-2-carboxamide, 2 Hydrochloride | 100% | Method B 1.15 min | 1074 |

| Compound Name/Structure | Yield | LCMS RT | ES +ve |
|---|---|---|---|

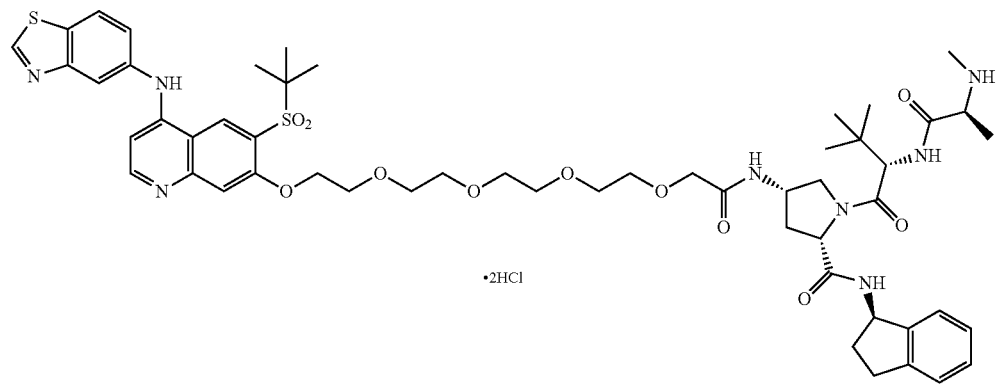 [SMILES: CN[C@@H](C)C(=O)N[C@H](C(=O)N1C[C@@H](NC(=O)COCCOCCOCCOCCOc2cc3nccc(Nc4ccc5scnc5c4)c3cc2S(=O)(=O)C(C)(C)C)C[C@H]1C(=O)N[C@@H]1CCc2ccccc21)C(C)(C)C]

Example 7
(2S,4S)-4-(14-((4-(benzo[d]thiazol-5-ylamino)-6-(tert-butylsulfonyl)quinolin-7-yl)oxy)-3,6,9,12-tetraoxatetradecanamido)-1-((S)-3,3-dimethyl-2-((S)-2-(methylamino)propanamido)butanoyl)-N-((R)-1-phenylpropyl)pyrrolidine-2-carboxamide, 2 Hydrochloride 100% | Method B 1.18 min | 1076

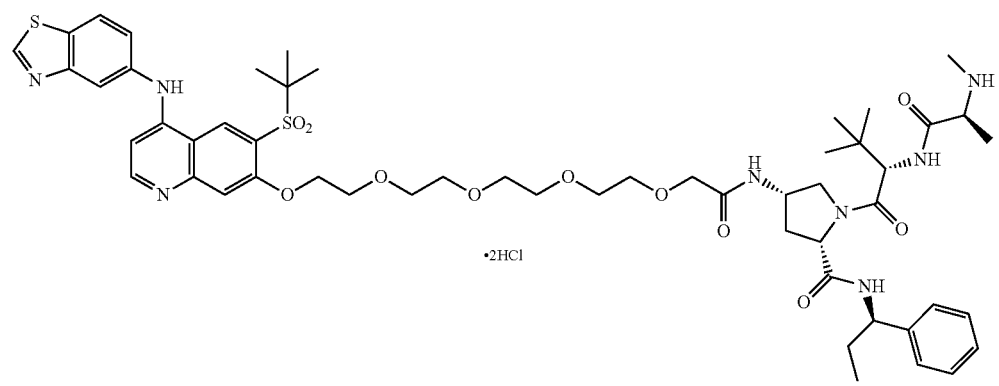 [SMILES: CC[C@@H](NC(=O)[C@@H]1C[C@H](NC(=O)COCCOCCOCCOCCOc2cc3nccc(Nc4ccc5scnc5c4)c3cc2S(=O)(=O)C(C)(C)C)CN1C(=O)[C@@H](NC(=O)[C@H](C)NC)C(C)(C)C)c1ccccc1]

Example 8
(2S,4S)-4-(14-((4-(benzo[d]thiazol-5-ylamino)-6-(tert-butylsulfonyl)quinolin-7-yl)oxy)-3,6,9,12-tetraoxatetradecanamido)-N-(2,6-difluorophenyl)-1-((S)-3,3-dimethyl-2-((S)-2-(methylamino)propanamido)butanoyl)pyrrolidine-2-carboxamide, 2 Hydrochloride 99% | Method B 1.09 min | 1069

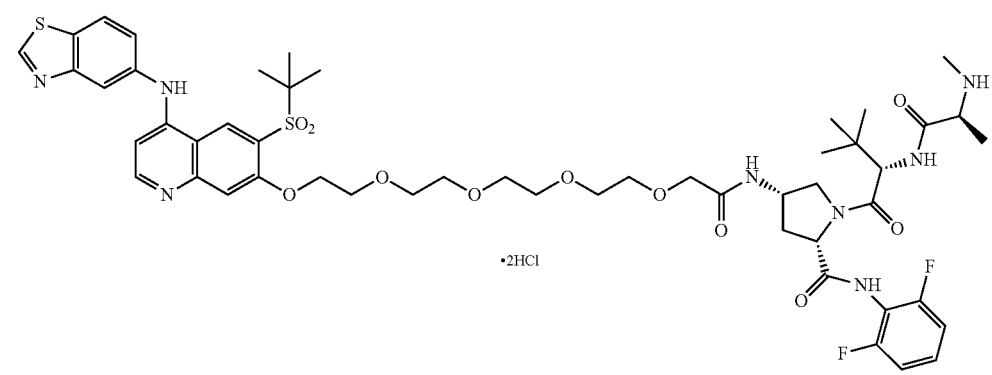 [SMILES: CN[C@@H](C)C(=O)N[C@H](C(=O)N1C[C@@H](NC(=O)COCCOCCOCCOCCOc2cc3nccc(Nc4ccc5scnc5c4)c3cc2S(=O)(=O)C(C)(C)C)C[C@H]1C(=O)Nc1c(F)cccc1F)C(C)(C)C]

Example 9

(2S,4S)-4-(2-(2-(2-(2-((6-(Tert-butylsulfonyl)-4-((5-fluoro-1H-indazol-3-yl)amino)quinolin-7-yl)oxy) ethoxy)ethoxy)ethoxy)ethoxy)-1-((S)-3,3-dimethyl-2-((S)-2-(methylamino)propanamido)butanoyl)-N-((R)-1,2,3,4-tetrahydronaphthalen-1-yl)pyrrolidine-2-carboxamide, 2 Hydrochloride

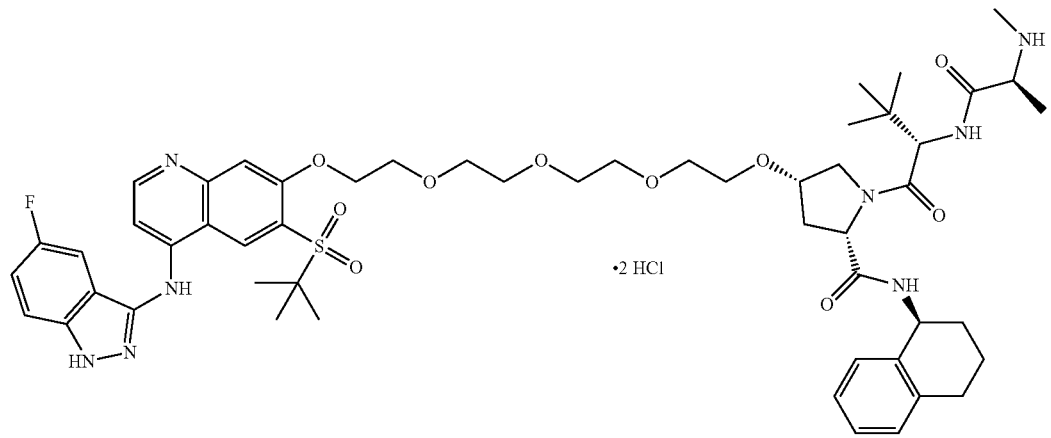 [SMILES: CN[C@@H](C)C(=O)N[C@H](C(=O)N1C[C@@H](OCCOCCOCCOCCOc2cc3nccc(Nc4n[nH]c5ccc(F)cc45)c3cc2S(=O)(=O)C(C)(C)C)C[C@H]1C(=O)N[C@H]1CCCc2ccccc21)C(C)(C)C]

A solution of tert-butyl ((S)-1-(((S)-1-((2S,4S)-4-(2-(2-(2-(2-((6-(tert-butylsulfonyl)-4-((5-fluoro-1H-indazol-3-yl)amino)quinolin-7-yl)ethoxy)ethoxy)ethoxy)ethoxy)-2-(((R)-1,2,3,4-tetrahydronaphthalen-1-yl)carbamoyl) pyrrolidin-1-yl)-3,3-dimethyl-1-oxobutan-2-yl)amino)-1-oxopropan-2-yl)(methyl)carbamate (68 mg, 0.06 mmol) in THF (0.5 mL) was treated with hydrochloric acid (4M in dioxan) (2 mL, 8 mmol). After 2 hours the mixture was evaporated to dryness to afford the title compound (57 mg, 0.052 mmol, 86% yield). This was repurified by mass-directed automated preparative HPLC (ammonium bicarbonate modifier) to afford the free base which was taken up in THF (3 mL) and treated with 4M HCl in dioxan (0.5 mL) and evaporated to dryness to afford the title compound (28 mg, 0.03 mmol, 42.2% yield). LCMS Method B RT=1.21 min, ES+ve 1031).

Example 10

(2S,4S)-4-(2-(2-(2-((6-(Tert-butylsulfonyl)-4-((5-fluoro-1H-indazol-3-yl)amino)quinolin-7-yl)oxy) ethoxy)ethoxy)ethoxy)-1-((S)-3,3-dimethyl-2-((S)-2-(methylamino)propanamido)butanoyl)-N-((R)-1,2,3,4-tetrahydronaphthalen-1-yl)pyrrolidine-2-carboxamide, 2 Hydrochloride

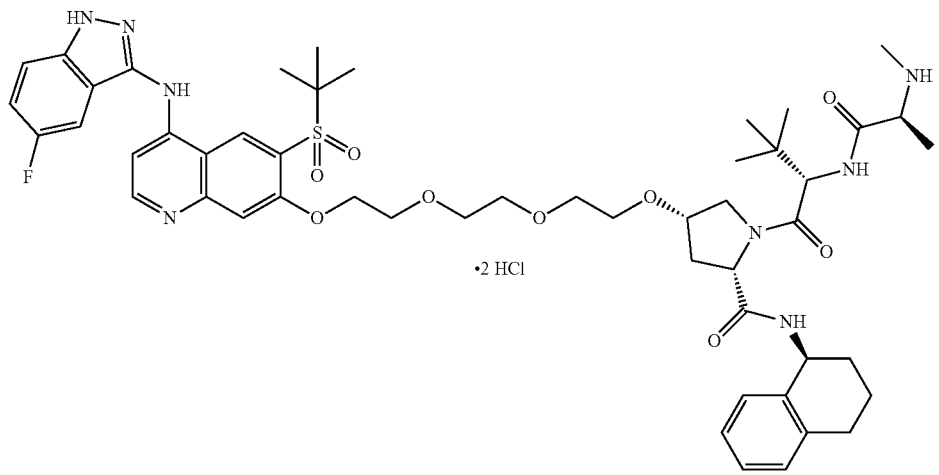 [SMILES: CN[C@@H](C)C(=O)N[C@H](C(=O)N1C[C@@H](OCCOCCOCCOc2cc3nccc(Nc4n[nH]c5ccc(F)cc45)c3cc2S(=O)(=O)C(C)(C)C)C[C@H]1C(=O)N[C@H]1CCCc2ccccc21)C(C)(C)C]

Using a method analogous to that for (2S,4S)-4-(2-(2-(2-(2-((6-(tert-butylsulfonyl)-4-((5-fluoro-1H-indazol-3-yl)amino)quinolin-7-yl)oxy)ethoxy)ethoxy)ethoxy)-1-((S)-3,3-dimethyl-2-((S)-2-(methylamino)propanamido)butanoyl)-N-((R)-1,2,3,4-tetrahydronaphthalen-1-yl)pyrrolidine-2-carboxamide, 2 hydrochloride (Example 4) using 2-(2-(2-(benzyloxy)ethoxy)ethoxy)ethyl 4-methylbenzenesulfonate in place of 1-phenyl-2,5,8,11-tetraoxatridecan-13-yl 4-methylbenzenesulfonate, to afford the title compound (70 mg, 0.07 mmol, 96% yield). LCMS Method B RT=1.18 min, ES+ve 987).

Example 11

5-(4-(2-((6-(Tert-butylsulfonyl)-4-((4,5-dimethyl-1H-pyrazol-3-yl)amino)quinazolin-7-yl)oxy)ethyl)piperazin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)pyrazine-2-carboxamide, 3 Hydrochloride

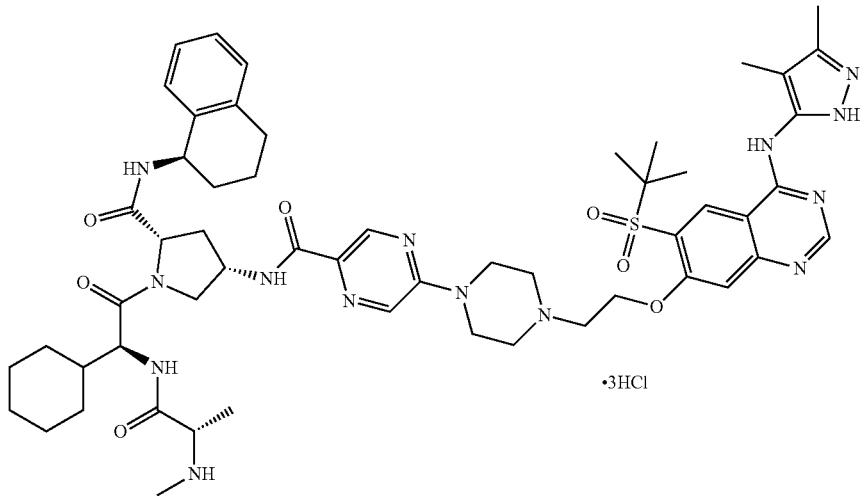 [SMILES: CN[C@@H](C)C(=O)N[C@H](C(=O)N1C[C@@H](NC(=O)c2cnc(N3CCN(CCOc4cc5ncnc(Nc6[nH]nc(C)c6C)c5cc4S(=O)(=O)C(C)(C)C)CC3)cn2)C[C@H]1C(=O)N[C@@H]1CCCc2ccccc21)C1CCCCC1]

A solution of tert-butyl ((S)-1-(((S)-2-((2S,4S)-4-(5-(4-(2-((6-(tert-butylsulfonyl)-4-((4,5-dimethyl-1H-pyrazol-3-yl)amino)quinazolin-7-yl)oxy)ethyl)piperazin-1-yl)pyrazine-2-carboxamido)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate (74 mg, 0.063 mmol) in DCM (2 mL) was treated with hydrochloric acid (4M in 1,4-dioxane) (0.9 mL, 3.6 mmol) and the mixture was stirred at ambient temperature for 1 h. The mixture was removed of solvent in vacuo to afford the title compound (70 mg, 0.06 mmol, 91% yield). LCMS Method B RT=1.12 min, ES+ve 1075.

The following compounds were prepared using a method analogous to that for 5-(4-(2-((6-(tert-butylsulfonyl)-4-((4,5-dimethyl-1H-pyrazol-3-yl)amino)quinazolin-7-yl)oxy)ethyl)piperazin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)pyrazine-2-carboxamide, 3 Hydrochloride:

| Compound Name/Structure | Yield | LCMS RT | ES +ve |
|---|---|---|---|
| Example 12<br>2-(4-(2-((6-(tert-butylsulfonyl)-4-((4,5-dimethyl-1H-pyrazol-3-yl)amino)quinazolin-7-yl)oxy)ethyl)piperazin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)pyrimidine-5-carboxamide hydrochloride | 100% | Method B 1.15 min | 1075.4 |

-continued

| Compound Name/Structure | Yield | LCMS RT | ES +ve |
|---|---|---|---|
| 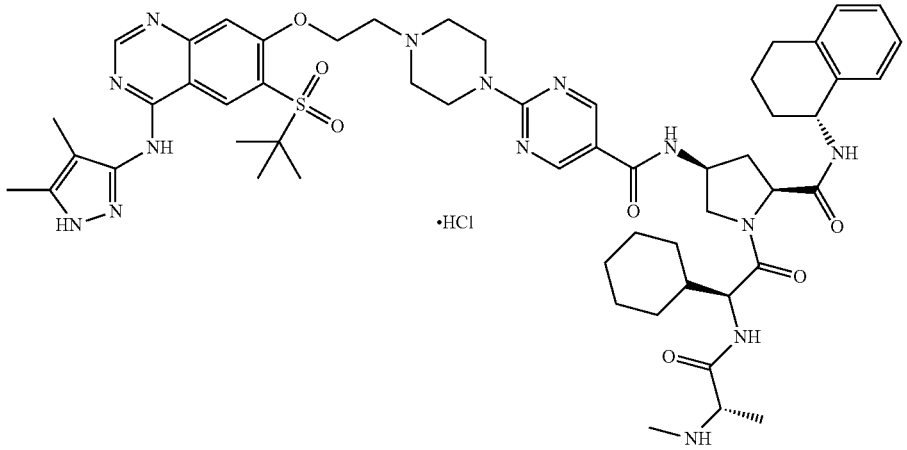 [SMILES: CN[C@@H](C)C(=O)N[C@H](C(=O)N1C[C@@H](NC(=O)c2cnc(N3CCN(CCOc4cc5ncnc(Nc6n[nH]c(C)c6C)c5cc4S(=O)(=O)C(C)(C)C)CC3)nc2)C[C@H]1C(=O)N[C@@H]1CCCc2ccccc21)C1CCCCC1 ; Cl]<br>Example 13<br>5-(4-(((6-(tert-butylsulfonyl)-4-((4,5-dimethyl-1H-pyrazol-3-yl)amino)quinazolin-7-yl)oxy)methyl)piperidin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)pyrazine-2-carboxamide | 98% | Method B 1.19 min | 1060.37 |
| 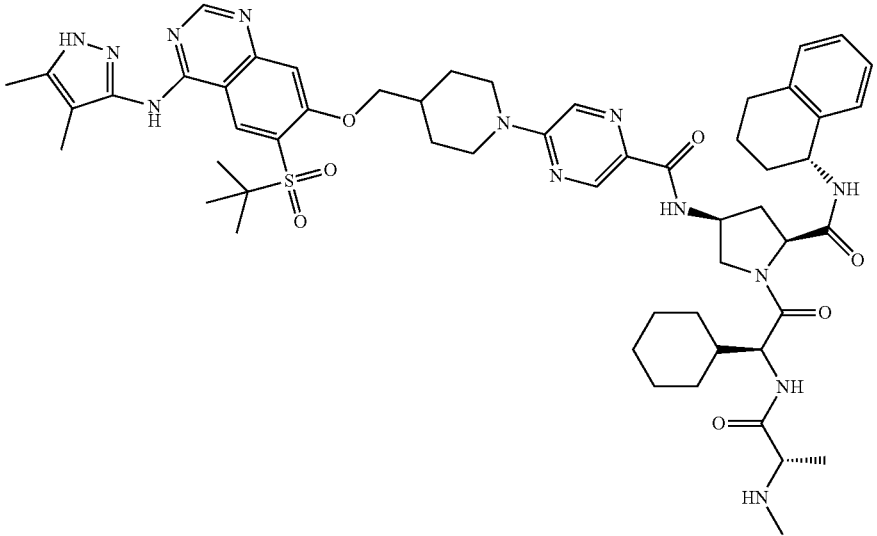 [SMILES: CN[C@@H](C)C(=O)N[C@H](C(=O)N1C[C@@H](NC(=O)c2cnc(N3CCC(COc4cc5ncnc(Nc6n[nH]c(C)c6C)c5cc4S(=O)(=O)C(C)(C)C)CC3)cn2)C[C@H]1C(=O)N[C@@H]1CCCc2ccccc21)C1CCCCC1]<br>Example 14<br>6-(4-(3-((6-(tert-butylsulfonyl)-4-((4,5-dimethyl-1H-pyrazol-3-yl)amino)quinazolin-7-yl)oxy)propyl)piperidin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)nicotinamide | 97% | Method B 1.28 min | 1087.4 |

| Compound Name/Structure | Yield | LCMS RT | ES +ve |
|---|---|---|---|
| Example 15<br>2-(4-(((6-(tert-butylsulfonyl)-4-((4,5-dimethyl-1H-pyrazol-3-yl)amino)quinazolin-7-yl)oxy)methyl)piperidin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)pyrimidine-5-carboxamide | 95% | Method B 1.23 min | 1060.4 |
| Example 16<br>6-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)nicotinamide | 94% | Method B 1.15 min | 1088.34 |

| Compound Name/Structure | Yield | LCMS RT | ES +ve |
|---|---|---|---|

Example 17

5-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)pyrazine-2-carboxamide 100%  Method B 1.15 min  1089.38

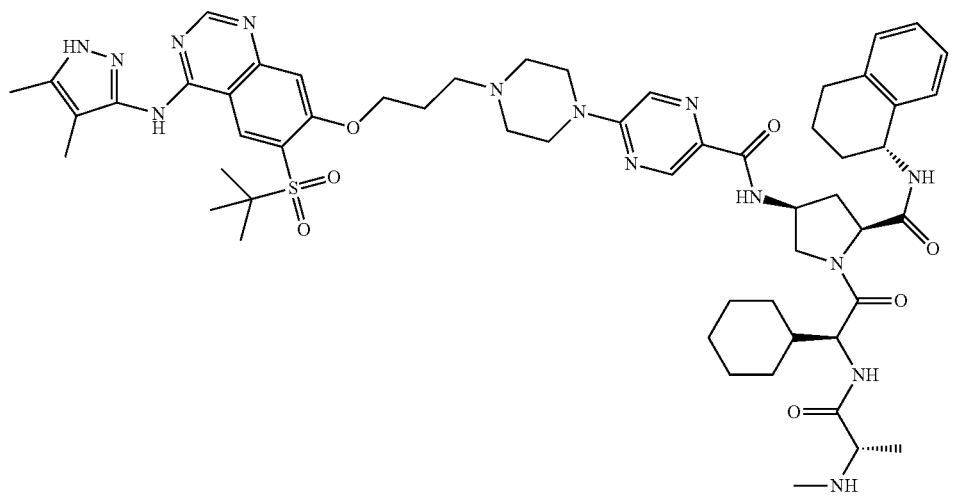 [SMILES: CN[C@@H](C)C(=O)N[C@H](C(=O)N1C[C@@H](NC(=O)c2cnc(N3CCN(CCCOc4cc5ncnc(Nc6n[nH]c(C)c6C)c5cc4S(=O)(=O)C(C)(C)C)CC3)cn2)C[C@H]1C(=O)N[C@@H]1CCCc2ccccc21)C1CCCCC1]

Example 18

2-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-1-((S)-2-cyclohexyl-2-((S)-2-(methylamino)propanamido)acetyl)-5-(((R)-1,2,3,4-tetrahydronaphthalen-1-yl)carbamoyl)pyrrolidin-3-yl)pyrimidine-5-carboxamide 100%  Method B 1.15 min  1064.41

| Compound Name/Structure | Yield | LCMS RT | ES +ve |
|---|---|---|---|

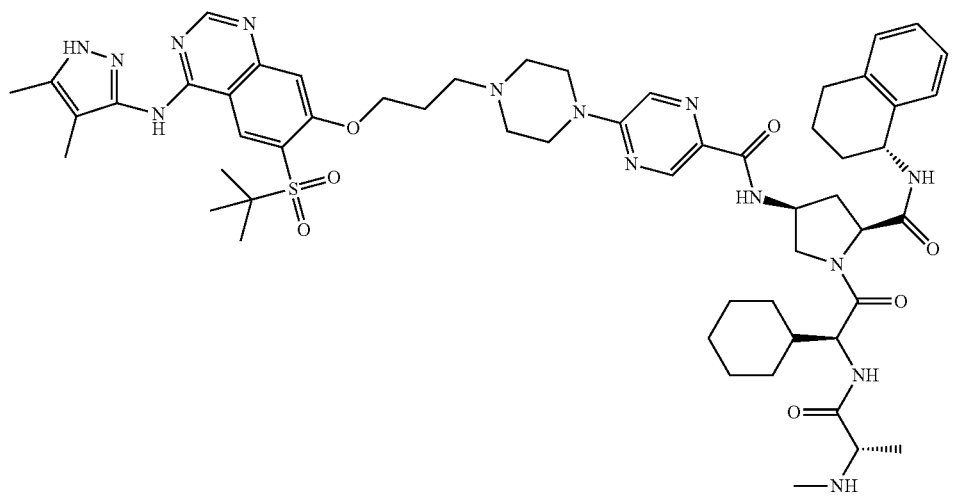 [SMILES: CN[C@@H](C)C(=O)N[C@H](C(=O)N1C[C@@H](NC(=O)c2cnc(N3CCN(CCCOc4cc5ncnc(Nc6n[nH]c(C)c6C)c5cc4S(=O)(=O)C(C)(C)C)CC3)cn2)C[C@H]1C(=O)N[C@@H]1CCCc2ccccc21)C1CCCCC1]

Example 19
5-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-1-((S)-3,3-dimethyl-2-((S)-2-(methylamino)propanamido)butanoyl)-5-(((R)-1,2,3,4-tetrahydronaphthalen-1-yl)carbamoyl)pyrrolidin-3-yl)pyrazine-2-carboxamide 10% | Method B 1.11 min | 1063.46

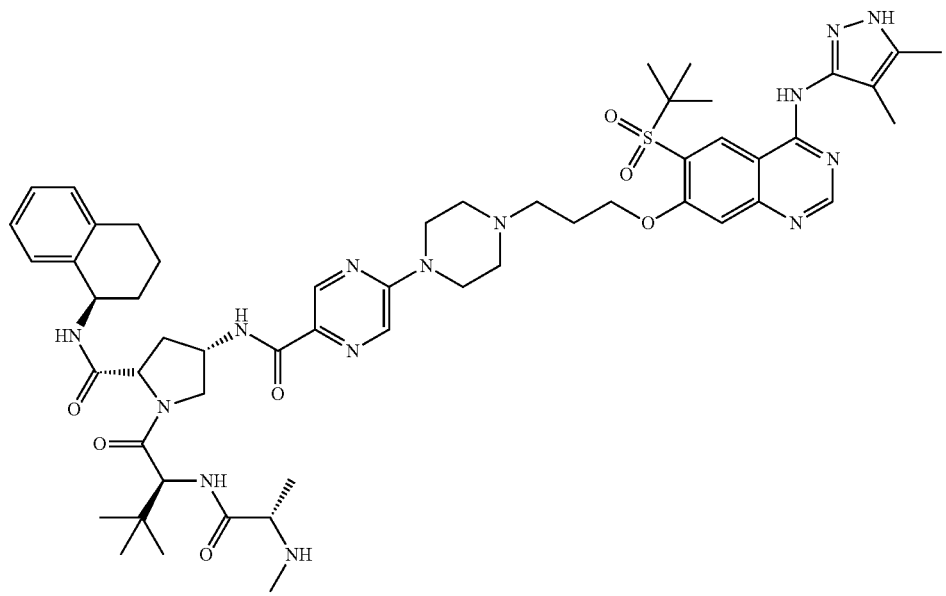

Example 20
(2S,4S)-4-((2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidin-5-yl)oxy)-1-((S)-3,3-dimethyl-2-((S)-2-(methylamino)propanamido)butanoyl)-N-((R)-1,2,3,4-tetrahydronaphthalen-1-yl)pyrrolidine-2-carboxamide, 4hydrochloride 99% | Method B 1.12 min | 1049.37

| Compound Name/Structure | Yield | LCMS RT | ES +ve |
|---|---|---|---|

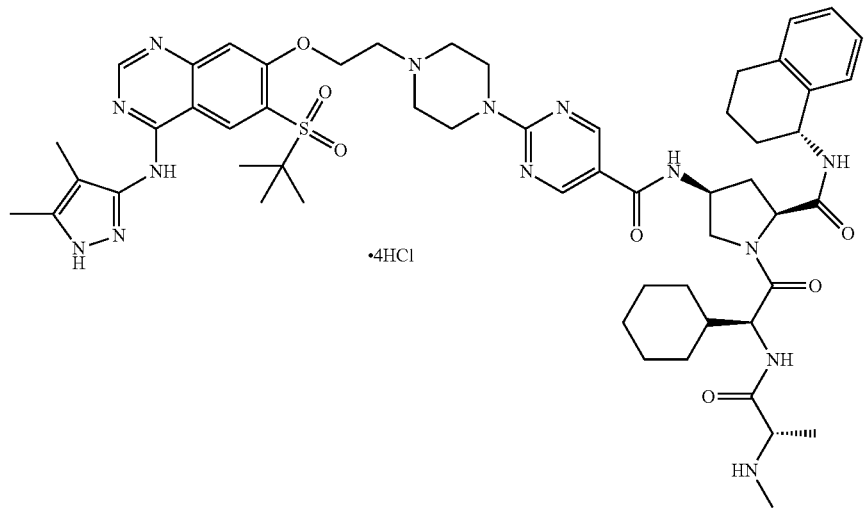 [SMILES: CN[C@@H](C)C(=O)N[C@H](C(=O)N1C[C@@H](NC(=O)c2cnc(N3CCN(CCOc4cc5ncnc(Nc6n[nH]c(C)c6C)c5cc4S(=O)(=O)C(C)(C)C)CC3)nc2)C[C@H]1C(=O)N[C@@H]1CCCc2ccccc21)C1CCCCC1]

Example 21
2-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-5-((2,6-difluorophenyl)carbamoyl)-1-((S)-3,3-dimethyl-2-((S)-2-(methylamino)propanamido)butanoyl)pyrrolidin-3-yl)pyrimidine-5-carboxamide 100% | Method B 1.02 min | 1045.35

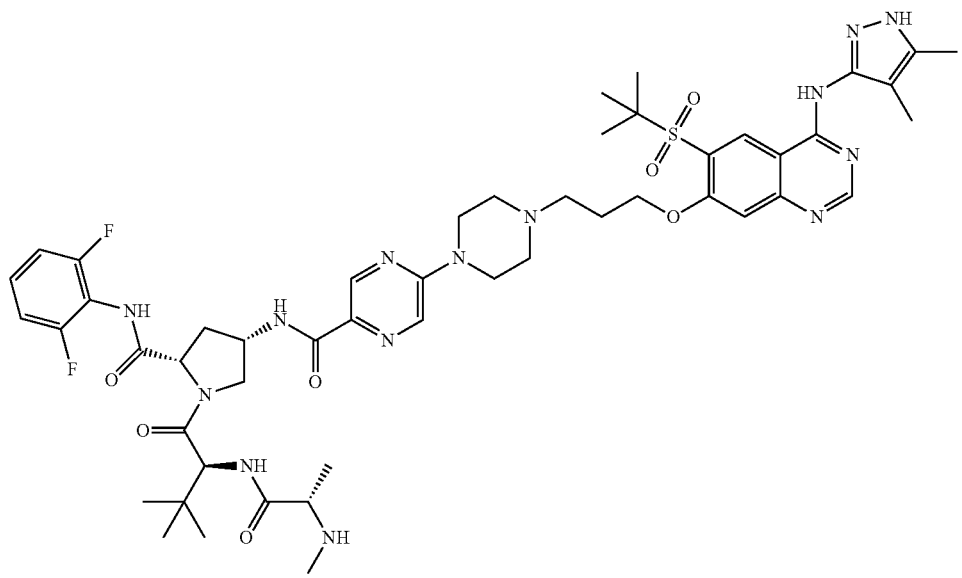 [SMILES: CN[C@@H](C)C(=O)N[C@H](C(=O)N1C[C@@H](NC(=O)c2cnc(N3CCN(CCCOc4cc5ncnc(Nc6n[nH]c(C)c6C)c5cc4S(=O)(=O)C(C)(C)C)CC3)cn2)C[C@H]1C(=O)Nc1c(F)cccc1F)C(C)(C)C]

Example 22
2-(4-(2-((6-(tert-butylsulfonyl)-4-((4,5-dimethyl-1H-pyrazol-3-yl)amino)quinazolin-7-yl)oxy)ethyl)piperazin-1-yl)-N-((3S,5S)-1-((S)-2-cyclohexyl-2-((S)-2-(methylamino)propanamido)acetyl)-5-((3-methyl-1-phenyl-1H-pyrazol-5-yl)carbamoyl)pyrrolidin-3-yl)pyrimidine-5-carboxamide 59% | Method B 1.03 min | 1101.3

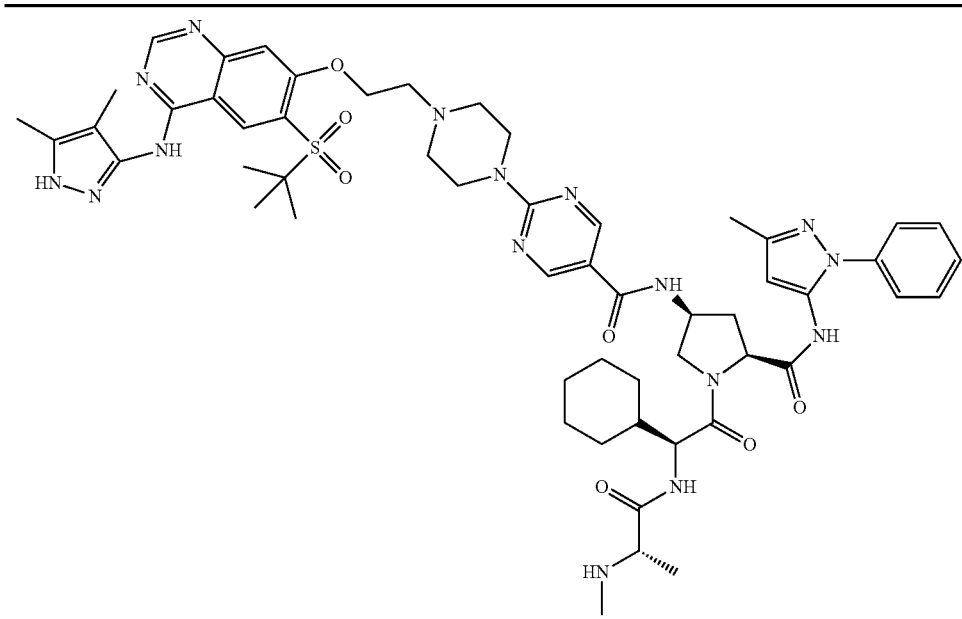
| Compound Name/Structure | Yield | LCMS RT | ES +ve |
|---|---|---|---|
| Example 23<br>2-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-1-((S)-2-cyclohexyl-2-((S)-2-(methylamino)propanamido)acetyl)-5-((3-methyl-1-phenyl-1H-pyrazol-5-yl)carbamoyl)pyrrolidin-3-yl)pyrimidine-5-carboxamide<br>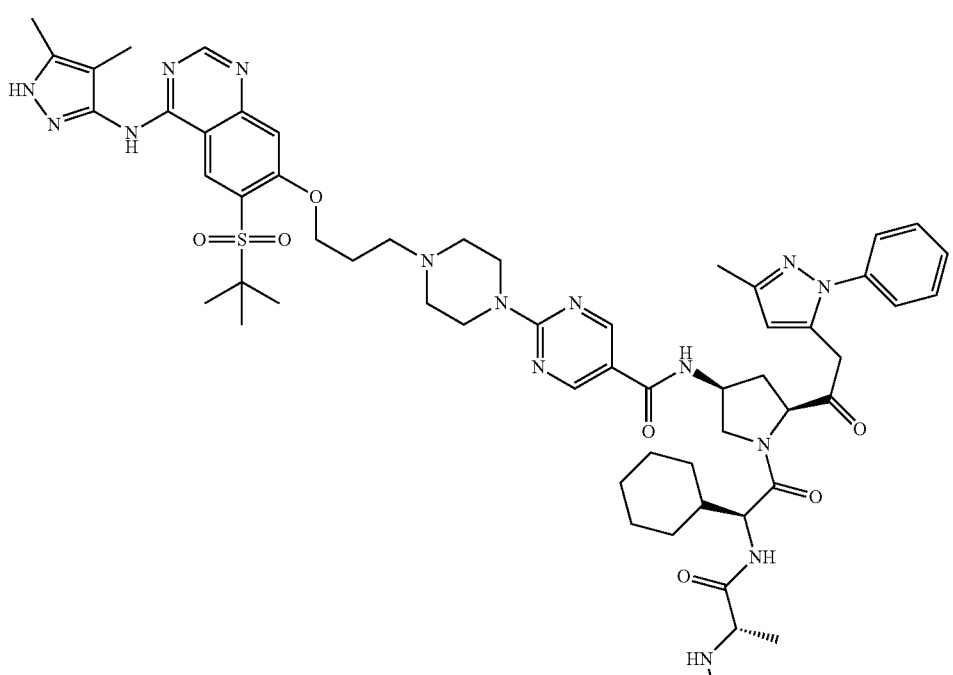 | 97% | Method B 1.04 min | 1115.4 |

Example 24

(S)-7-((6-(4-(((6-(Tert-butylsulfonyl)-4-((4,5-dimethyl-1H-pyrazol-3-yl)amino)quinazolin-7-yl)oxy)piperidin-1-yl)pyrimidin-4-yl)oxy)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide

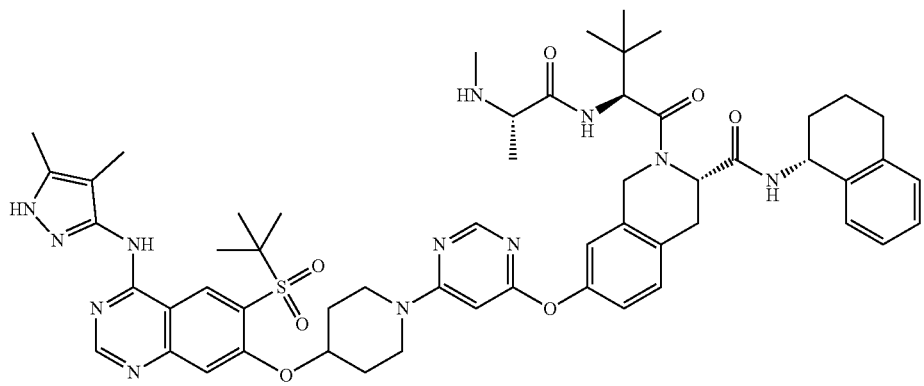 [SMILES: CN[C@@H](C)C(=O)N[C@H](C(=O)N1Cc2cc(Oc3cc(N4CCC(Oc5cc6ncnc(Nc7n[nH]c(C)c7C)c6cc5S(=O)(=O)C(C)(C)C)CC4)ncn3)ccc2C[C@H]1C(=O)N[C@@H]1CCCc2ccccc21)C(C)(C)C]

A solution of tert-butyl ((S)-1-(((S)-1-((S)-7-((6-(4-(((6-(tert-butylsulfonyl)-4-((4,5-dimethyl-1H-pyrazol-3-yl)amino)quinazolin-7-yl)oxy)piperidin-1-yl)pyrimidin-4-yl)oxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (70 mg, 0.061 mmol) in dichloromethane (3 mL) was treated with trifluoroacetic acid (1 mL) and the mixture stirred for 15 minutes. The mixture was evaporated to dryness, treated with DMSO (1.5 mL) and DIPEA (0.5 mL) and then the product was subjected to purification by mass-directed automated preparative HPLC (ammonium bicarbonate modifier) to afford the title compound (46 mg, 0.04 mmol, 72% yield). LCMS RT=1.23 min, ES+ve 1055.

Example 25

(S)-7-((6-(4-(((6-(Tert-butylsulfonyl)-4-((4,5-dimethyl-1H-pyrazol-3-yl)amino)quinazolin-7-yl)oxy)methyl)piperidin-1-yl)pyrimidin-4-yl)oxy)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide The following compound was made using a method analogous to that for (S)-7-((6-(4-(((6-(tert-butylsulfonyl)-4-((4,5-dimethyl-1H-pyrazol-3-yl)amino)quinazolin-7-yl)oxy)piperidin-1-yl)pyrimidin-4-yl)oxy)-2-((S)-3,3-dimethyl-2-((S)-2-(methylamino)propanamido)butanoyl)-N-((R)-1,2,3,4-tetrahydronaphthalen-1-yl)-1,2,3,4-tetrahydroisoquinoline-3-carboxamide:

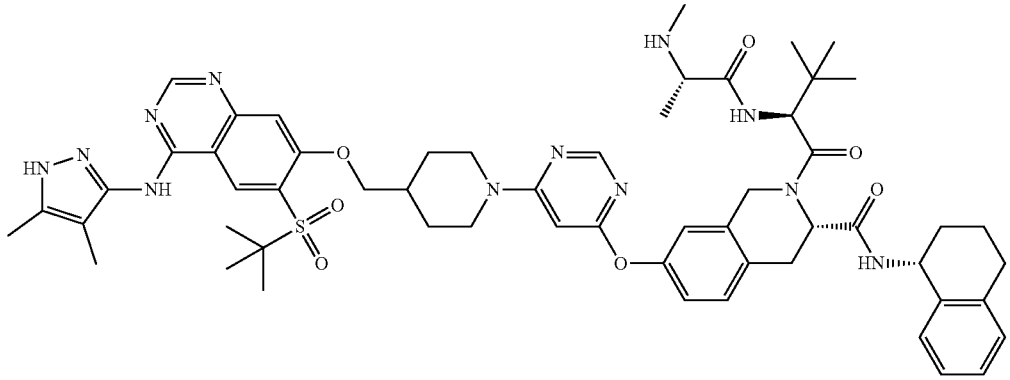 [SMILES: CN[C@@H](C)C(=O)N[C@H](C(=O)N1Cc2cc(Oc3cc(N4CCC(COc5cc6ncnc(Nc7n[nH]c(C)c7C)c6cc5S(=O)(=O)C(C)(C)C)CC4)ncn3)ccc2C[C@H]1C(=O)N[C@@H]1CCCc2ccccc21)C(C)(C)C]

74% yield. LCMS RT=1.26 min, ES+ve 1069.

Example 26

(2S,4S)-4-((2-(4-(((6-(Tert-butylsulfonyl)-4-((4,5-dimethyl-1H-pyrazol-3-yl)amino)quinazolin-7-yl)oxy)methyl)piperidin-1-yl)pyrimidin-5-yl)oxy)-1-((S)-2-cyclohexyl-2-((S)-2-(methylamino)propanamido)acetyl)-N-((R)-1,2,3,4-tetrahydronaphthalen-1-yl)pyrrolidine-2-carboxamide, 4Hydrochloride

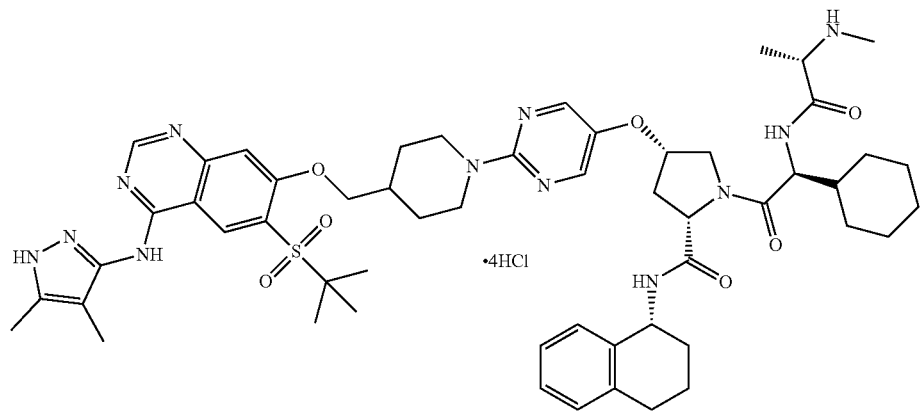 [SMILES: CN[C@@H](C)C(=O)N[C@H](C(=O)N1C[C@@H](Oc2cnc(N3CCC(COc4cc5ncnc(Nc6n[nH]c(C)c6C)c5cc4S(=O)(=O)C(C)(C)C)CC3)nc2)C[C@H]1C(=O)N[C@@H]1CCCc2ccccc21)C1CCCCC1]

A solution of tert-butyl ((S)-1-(((S)-2-((2S,4S)-4-((2-(4-(((6-(tert-butylsulfonyl)-4-((4,5-dimethyl-1H-pyrazol-3-yl)amino)quinazolin-7-yl)oxy)methyl)piperidin-1-yl)pyrimidin-5-yl)oxy)-2-(((R)-1,2,3,4-tetrahydronaphthalen-1-yl)carbamoyl)pyrrolidin-1-yl)-1-cyclohexyl-2-oxoethyl)amino)-1-oxopropan-2-yl)(methyl)carbamate (58 mg, 0.051 mmol) in THF (2 mL) was treated with hydrochloric acid (4 M in dioxane) (2 mL, 8 mmol) and the mixture was stirred at ambient temperature for 2 hours. The mixture was evaporated to dryness to afford the title compound (56 mg, 0.05 mmol, 93% yield). LCMS Method B RT=1.27 min, ES+ve 1033.

The following compounds were prepared in an analogous manner to (2S,4S)-4-((2-(4-(((6-(Tert-butylsulfonyl)-4-((4,5-dimethyl-1H-pyrazol-3-yl)amino)quinazolin-7-yl)oxy)methyl)piperidin-1-yl)pyrimidin-5-yl)oxy)-1-((S)-2-cyclohexyl-2-((S)-2-(methylamino)propanamido)acetyl)-N-((R)-1,2,3,4-tetrahydronaphthalen-1-yl)pyrrolidine-2-carboxamide, 4Hydrochloride using the appropriate amine starting material:

| Compound Name/Structure | Yield | LCMS RT | ES +ve |
|---|---|---|---|
| Example 27<br>(2S,4S)-4-((2-(4-((6-(tert-butylsulfonyl)-4-((4,5-dimethyl-1H-pyrazol-3-yl)amino)quinazolin-7-yl)oxy)piperidin-1-yl)pyrimidin-5-yl)oxy)-1-((S)-2-cyclohexyl-2-((S)-2-(methylamino)propanamido)acetyl)-N-((R)-1,2,3,4-tetrahydronaphthalen-1-yl)pyrrolidine-2-carboxamide, 4Hydrochloride | 93% | Method B 1.25 min | 1019 |

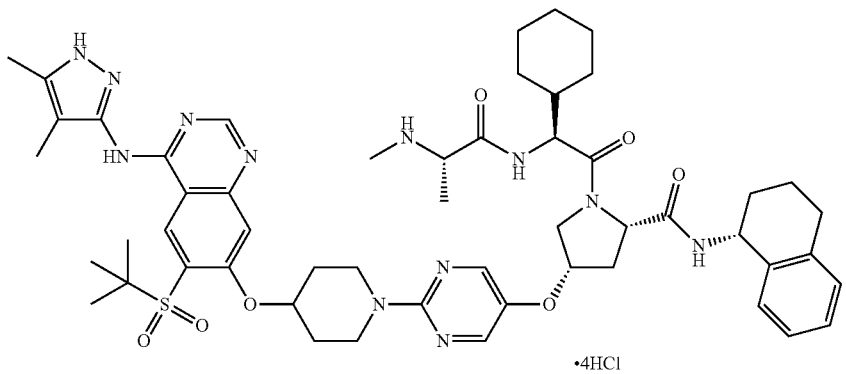 [SMILES: CN[C@@H](C)C(=O)N[C@H](C(=O)N1C[C@@H](Oc2cnc(N3CCC(Oc4cc5ncnc(Nc6n[nH]c(C)c6C)c5cc4S(=O)(=O)C(C)(C)C)CC3)nc2)C[C@H]1C(=O)N[C@@H]1CCCc2ccccc21)C1CCCCC1]

| Compound Name/Structure | Yield | LCMS RT | ES +ve |
|---|---|---|---|
| Example 28<br>(2S,4S)-4-((2-(4-(2-(((6-(tert-butylsulfonyl)-4-((4,5-dimethyl-1H-pyrazol-3-yl)amino)quinazolin-7-yl)oxy)ethyl)piperazin-1-yl)pyrimidin-5-yl)oxy)-1-((S)-2-cyclohexyl-2-((S)-2-(methylamino)propanamido)acetyl)-N-((R)-1,2,3,4-tetrahydronaphthalen-1-yl)pyrrolidine-2-carboxamide, 4Hydrochloride | 94% | Method B 1.20 min | 1048 |
| Example 29<br>(2S,4S)-4-((2-(4-(2-(((6-(tert-butylsulfonyl)-4-((4,5-dimethyl-1H-pyrazol-3-yl)amino)quinazolin-7-yl)oxy)ethyl)piperidin-1-yl)pyrimidin-5-yl)oxy)-1-((S)-2-cyclohexyl-2-((S)-2-(methylamino)propanamido)acetyl)-N-((R)-1,2,3,4-tetrahydronaphthalen-1-yl)pyrrolidine-2-carboxamide, 4Hydrochloride | 96% | Method B 1.30 min | 1047 |
| Example 30<br>(2S,4S)-4-((2-(4-(3-(((6-(tert-butylsulfonyl)-4-((4,5-dimethyl-1H-pyrazol-3-yl)amino)quinazolin-7-yl)oxy)propyl)piperidin-1-yl)pyrimidin-5-yl)oxy)-1-((S)-2-cyclohexyl-2-((S)-2-(methylamino)propanamido)acetyl)-N-((R)-1,2,3,4-tetrahydronaphthalen-1-yl)pyrrolidine-2-carboxamide, 4Hydrochloride | 91% | Method B 1.34 min | 1061 |

| Compound Name/Structure | Yield | LCMS RT | ES +ve |
|---|---|---|---|
| Example 31<br>(2S,4S)-4-((2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidin-5-yl)oxy)-1-((S)-3,3-dimethyl-2-((S)-2-(methylamino)propanamido)butanoyl)-N-((R)-1,2,3,4-tetrahydronaphthalen-1-yl)pyrrolidine-2-carboxamide hydrochloride | 77% | Method B 1.11 min | 1022.4 |
| Example 32<br>(2S,4S)-4-((2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidin-5-yl)oxy)-N-(2,6-difluorophenyl)-1-((S)-3,3-dimethyl-2-((S)-2-(methylamino)propanamido)butanoyl)pyrrolidine-2-carboxamide hydrochloride | 20% | Method B 1.04 min | 1004 |
| Example 33<br>2-(4-(2-((6-(Tert-butylsulfonyl)-4-((4,5-dimethyl-1H-pyrazol-3-yl)amino)quinazolin-7-yl)oxy)ethyl)piperazin-1-yl)-N-((3S,5S)-5-((2,6-difluorophenyl)carbamoyl)-1-((S)-3,3-dimethyl-2-((S)-2-(methylamino)propanamido)butanoyl)pyrrolidin-3-yl)pyrimidine-5-carboxamide | 38% | Method B 1.02 min | 1031.49 |

| Compound Name/Structure | Yield | LCMS RT | ES +ve |
|---|---|---|---|
| Example 34<br>5-(4-(3-((6-(Tert-butylsulfonyl)-4-((4,5-dimethyl-1H-pyrazol-3-yl)amino)quinazolin-7-yl)oxy)propyl)piperazin-1-yl)-N-((3S,5S)-5-((2,6-difluorophenyl)carbamoyl)-1-((S)-3,3-dimethyl-2-((S)-2-(methylamino)propanamido)butanoyl)pyrrolidin-3-yl)pyrazine-2-carboxamide | 26% | Method B 1.00 min | 1045.32 |

Example 35

(S)-1-((S)-2-(1-(2-(4-(2-((6-(Tert-butylsulfonyl)-4-((4,5-dimethyl-1H-pyrazol-3-yl)amino)quinazolin-7-yl)oxy)ethyl)piperazin-1-yl)pyrimidine-5-carbonyl)piperidin-4-yl)-2-((S)-2-(methylamino)propanamido)acetyl)-N-((R)-1,2,3,4-tetrahydronaphthalen-1-yl)pyrrolidine-2-carboxamide

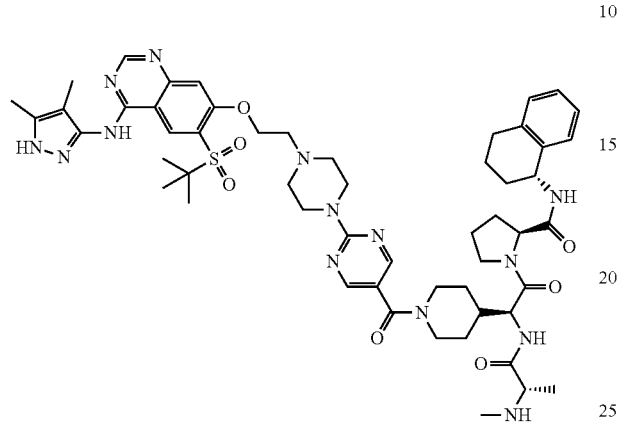

(9H-Fluoren-9-yl)methyl ((S)-1-(((S)-1-(1-(2-(4-(2-((6-(tert-butylsulfonyl)-4-((4,5-dimethyl-1H-pyrazol-3-yl)amino)quinazolin-7-yl)oxy)ethyl)piperazin-1-yl)pyrimidine-5-carbonyl)piperidin-4-yl)-2-oxo-2-((S)-2-(((R)-1,2,3,4-tetrahydronaphthalen-1-yl)carbamoyl)pyrrolidin-1-yl)ethyl)amino)-1-oxopropan-2-yl)(methyl)carbamate (40 mg, 0.031 mmol) was dissolved in tetrahydrofuran (2 mL) and treated with piperidine (3 mL, 30 mmol). After 1 hr, the reaction was concentrated in vacuo and purified by mass-directed automated preparative HPLC (ammonium bicarbonate modifier) to afford the title compound (26 mg, 0.024 mmol, 12% yield). LCMS Method B RT=0.98 min, ES+ve 1061.

| Compound Name/Structure | Yield | LCMS RT (mins) | ES +ve |
|---|---|---|---|
| Example 36<br>(S)-1-((S)-2-(1-(2-(4-(3-((6-(tert-butylsulfonyl)-4-((4,5-dimethyl-1H-pyrazol-3-yl)amino)quinazolin-7-yl)oxy)propyl)piperazin-1-yl)pyrimidine-5-carbonyl)piperidin-4-yl)-2-((S)-2-(methylamino)propanamido)acetyl)-N-((R)-1,2,3,4-tetrahydronaphthalen-1-yl)pyrrolidine-2-carboxamide<br>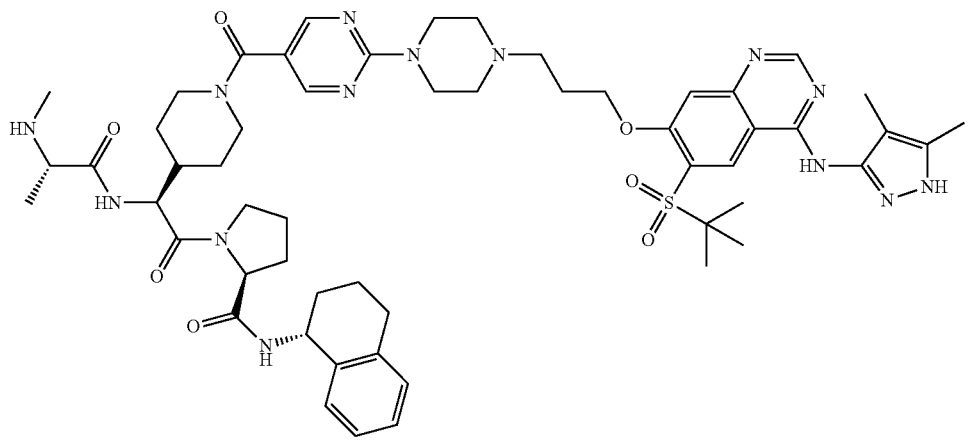 [SMILES: CN[C@@H](C)C(=O)N[C@H](C(=O)N1CCC[C@H]1C(=O)N[C@@H]1CCCc2ccccc21)C1CCN(C(=O)c2cnc(N3CCN(CCCOc4cc5ncnc(Nc6n[nH]c(C)c6C)c5cc4S(=O)(=O)C(C)(C)C)CC3)nc2)CC1] | 11% | Method B 1.00 min | 1075.35 |

Example 37

(5S,8S,10aR)-N-Benzhydryl-3-(5-(4-(((6-(tert-butyl-sulfonyl)-4-((4,5-dimethyl-1H-pyrazol-3-yl)amino)quinazolin-7-yl)oxy)methyl)piperidin-1-yl)pyrazine-2-carbonyl)-5-((S)-2-(methylamino)propanamido)-6-oxodecahydropyrrolo[1,2-a][1,5]diazocine-8-carboxamide

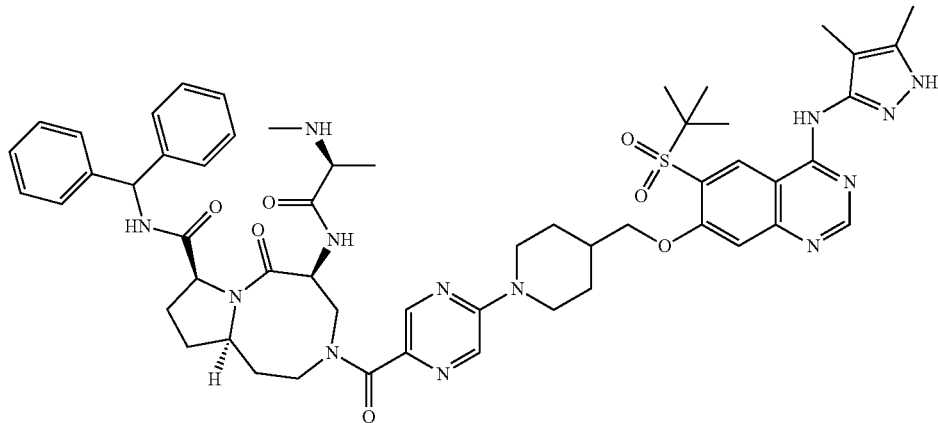 [SMILES: CN[C@@H](C)C(=O)N[C@H]1CN(C(=O)c2cnc(N3CCC(COc4cc5ncnc(Nc6n[nH]c(C)c6C)c5cc4S(=O)(=O)C(C)(C)C)CC3)cn2)CC[C@H]2CC[C@@H](C(=O)NC(c3ccccc3)c3ccccc3)N2C1=O]

Tert-butyl ((S)-1-(((5S,8S,10aR)-8-(benzhydrylcarbamoyl)-3-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)-6-oxodecahydropyrrolo[1,2-a][1,5]diazocin-5-yl)amino)-1-oxopropan-2-yl)(methyl)carbamate (24 mg, 0.021 mmol) was treated with trifluoroacetic acid (1 mL). After 1 hr the reaction mixture was concentrated in vacuo and the residue dissolved in methanol (5 mL) and passed through a 500 mg amino propyl cartridge eluting with methanol. The resultant product-containing fraction was evaporated to dryness to obtain the title compound (20 mg, 0.019 mmol, 47% yield). LCMS Method B RT 1.09 min, ES+ve m/z 1055

The following compound was prepared in a method analogous to that for (5S,8S,10aR)-N-benzhydryl-3-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)-5-((S)-2-(methylamino)propanamido)-6-oxodecahydropyrrolo[1,2-a][1,5]diazocine-8-carboxamide:

| Compound Name/Structure | Yield | LCMS RT | ES +ve |
|---|---|---|---|
| Example 38<br>(5S,8S,10aR)-3-(5-(4-(((6-(tert-butylsulfonyl)-4-((4,5-dimethyl-1H-pyrazol-3-yl)amino)quinazolin-7-yl)oxy)methyl)piperidin-1-yl)pyrazine-2-carbonyl)-5-((S)-2-(methylamino)propanamido)-6-oxo-N-((R)-1,2,3,4-tetrahydronaphthalen-1-yl)decahydropyrrolo[1,2-a][1,5]diazocine-8-carboxamide | 98% | Method B 1.04 min | 1019.34 |

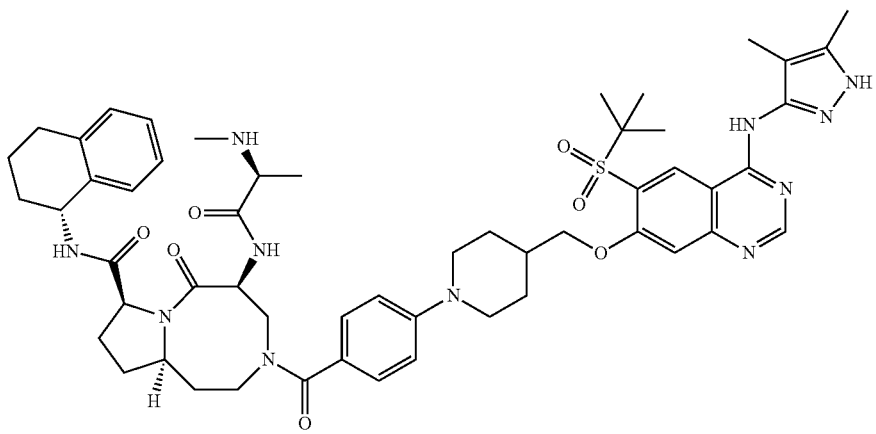 [SMILES: CN[C@@H](C)C(=O)N[C@H]1CN(C(=O)c2ccc(N3CCC(COc4cc5ncnc(Nc6n[nH]c(C)c6C)c5cc4S(=O)(=O)C(C)(C)C)CC3)cc2)CC[C@H]2CC[C@@H](C(=O)N[C@@H]3CCCc4ccccc43)N2C1=O]

-continued

| Compound Name/Structure | Yield | LCMS RT | ES +ve |
|---|---|---|---|
| Example 39<br>(5S,8S,10aR)-3-(5-(4-(3-((6-(tert-butylsulfonyl)-4-((4,5-dimethyl-1H-pyrazol-3-yl)amino)quinazolin-7-yl)oxy)propyl)piperazin-1-yl)pyrazine-2-carbonyl)-5-((S)-2-(methylamino)propanamido)-6-oxo-N-((R)-1,2,3,4-tetrahydronaphthalen-1-yl)decahydropyrrolo[1,2-a][1,5]diazocine-8-carboxamide<br>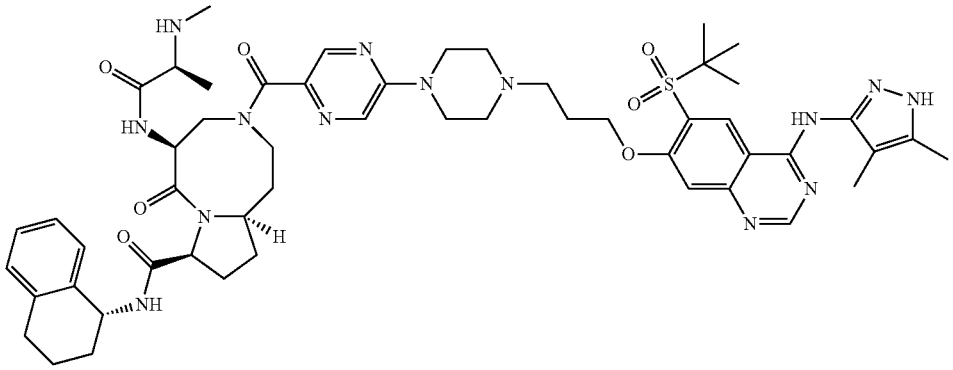 [SMILES: CN[C@@H](C)C(=O)N[C@H]1CN(C(=O)c2cnc(N3CCN(CCCOc4cc5ncnc(Nc6n[nH]c(C)c6C)c5cc4S(=O)(=O)C(C)(C)C)CC3)cn2)CC[C@H]2CC[C@@H](C(=O)N[C@@H]3CCCc4ccccc43)N2C1=O] | 99% | Method B 1.00 min | 1047.52 |
| Example 40<br>(5S,8S,10aR)-3-(2-(4-(3-((6-(tert-butylsulfonyl)-4-((4,5-dimethyl-1H-pyrazol-3-yl)amino)quinazolin-7-yl)oxy)propyl)piperazin-1-yl)pyimidine-5-carbonyl)-5-((S)-2-(methylamino)propanamido)-6-oxo-N-((R)-1,2,3,4-tetrahydronaphthalen-1-yl)decahydropyrrolo[1,2-a][1,5]diazocine-8-carboxamide<br>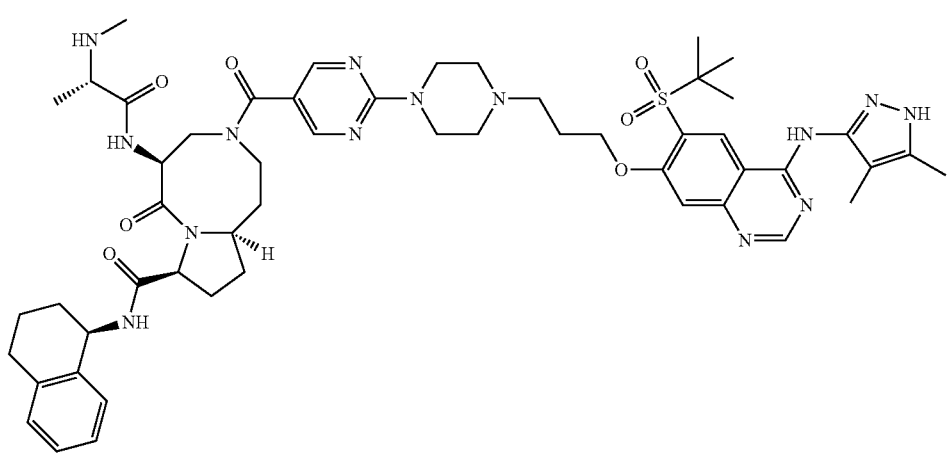 [SMILES: CN[C@@H](C)C(=O)N[C@H]1CN(C(=O)c2cnc(N3CCN(CCCOc4cc5ncnc(Nc6n[nH]c(C)c6C)c5cc4S(=O)(=O)C(C)(C)C)CC3)nc2)CC[C@H]2CC[C@@H](C(=O)N[C@@H]3CCCc4ccccc43)N2C1=O] | 99% | Method B 1.01 min | 1045.36 |

Western Blot Quantification of RIP2 Levels in THP1 Cells

Compounds were tested in THP1 cells (acute myeloid leukaemia—BioCat 106491) and the effect on RIP2 protein levels were assessed by Western blotting. For each sample $7.5 \times 10^6$ cells were resuspended in media containing the indicated concentrations of PROTAC and incubated 37° C. and 5% $CO_2$ overnight. The following day, cells were harvested, and the total amount of protein was quantified using the Pierce™ BCA Protein Assay kit (Thermo Scientific, 23227). 25 µg of total protein were separated on a polyacrylamide Bis-Tris gel at constant voltage and further transferred onto PVDF membranes (Millipore, IPFL00010). Membranes were blocked against non-specific binding with Odyssey blocking buffer (Licor, 927-40000) for 1 hour at room temperature, then incubated with the primary antibodies rabbit anti-RIPK2 (Cell Signaling, 4142) overnight at 4° C. Next day the mouse anti-actin (Sigma, A2228) at a 1:20 000 dilution was added and the membranes were further incubated for 2 hours at room temperature.

Membranes were washed 3 times with PBS+0.1% Tween 20 then incubated with donkey anti-mouse 800CW (Licor, 926-32212) and donkey anti-mouse IRdye 680RD (Licor, 926-68072) diluted 1:5 000 in Odyssey blocking buffer+ 0.1% Tween 20+0.01% SDS, 1 hour at room temperature, followed by washing in PBS+0.1% Tween 20. The infrared signal was detected using an Odyssey scanner (Licor Biosciences) and densitometry was performed using the Odyssey 2.1 Analyser software (Licor Biosciences).

RIPK2 degradation was expressed relative to the DMSO only treated sample. Compounds displayed >80% degradation of RIP2 at concentrations <1 uM.

The invention claimed is:
1. A compound which is 5-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-5-((2,6-difluorophenyl)carbamoyl)-1-((S)-3,3-dimethyl-2-((S)-2-(methylamino)propanamido)butanoyl)pyrrolidin-3-yl)pyrazine-2-carboxamide:

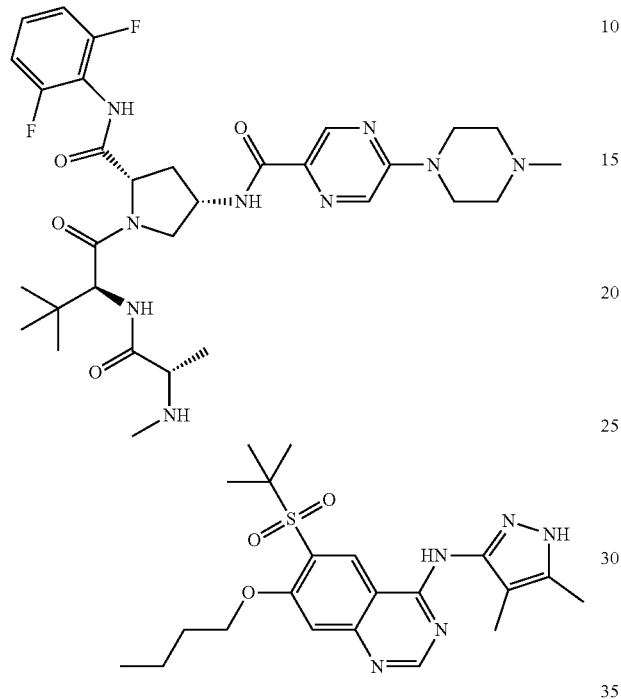

or a pharmaceutically acceptable salt thereof.

2. A compound according to claim 1 which is 5-(4-(3-((6-(tert-butylsulfonyl)-4-((4,5-dimethyl-1H-pyrazol-3-yl)amino)quinazolin-7-yl)oxy)propyl)piperazin-1-yl)-N-((3S,5S)-5-((2,6-difluorophenyl)carbamoyl)-1-((S)-3,3-dimethyl-2-((S)-2-(methylamino)propanamido)butanoyl)pyrrolidin-3-yl)pyrazine-2-carboxamide:

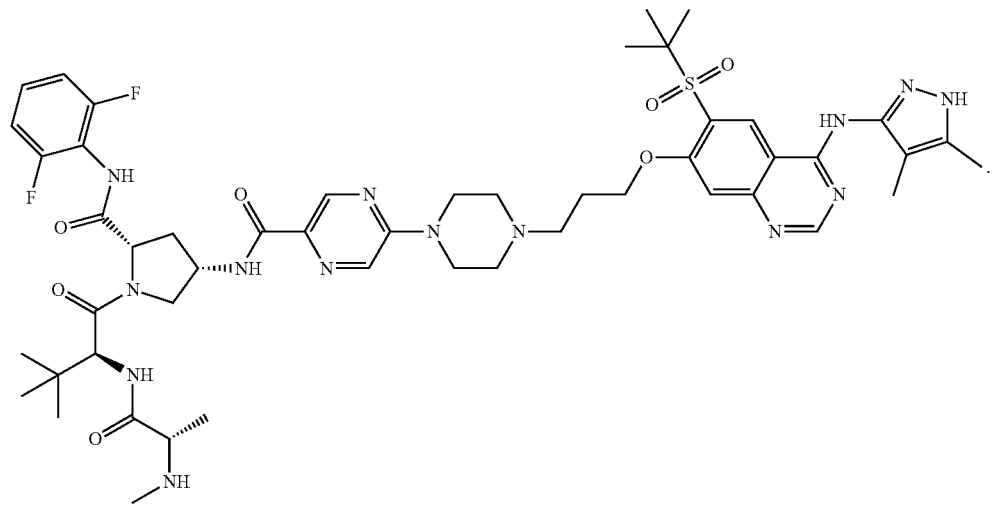 [SMILES: CN[C@@H](C)C(=O)N[C@H](C(=O)N1C[C@@H](NC(=O)c2cnc(N3CCN(CCCOc4cc5ncnc(Nc6n[nH]c(C)c6C)c5cc4S(=O)(=O)C(C)(C)C)CC3)cn2)C[C@H]1C(=O)Nc1c(F)cccc1F)C(C)(C)C]

3. A pharmaceutical composition comprising a compound according to claim 1 or a pharmaceutically acceptable salt thereof and one or more of pharmaceutically acceptable carriers, diluents and excipients.

4. A combination comprising a compound of according to claim 1, or a pharmaceutically acceptable salt thereof and at least one further therapeutic agent.

5. A pharmaceutical composition comprising a compound according to claim 2 and one or more of pharmaceutically acceptable carriers, diluents and excipients.

6. A combination comprising a compound of according to claim 2 and at least one further therapeutic agent.

* * * * *